US009822401B2

(12) United States Patent
Oberstrass

(10) Patent No.: US 9,822,401 B2
(45) Date of Patent: Nov. 21, 2017

(54) METHODS AND SYSTEMS FOR NUCLEIC ACID AMPLIFICATION

(71) Applicant: GenapSys, Inc., Redwood City, CA (US)

(72) Inventor: Florian Oberstrass, Menlo Park, CA (US)

(73) Assignee: GENAPSYS, INC., Redwood City, CA (US)

( * ) Notice: Subject to any disclaimer, the term of this patent is extended or adjusted under 35 U.S.C. 154(b) by 276 days.

(21) Appl. No.: 14/688,764

(22) Filed: Apr. 16, 2015

(65) Prior Publication Data

US 2015/0344943 A1 Dec. 3, 2015

Related U.S. Application Data

(60) Provisional application No. 62/025,626, filed on Jul. 17, 2014, provisional application No. 61/981,435, filed on Apr. 18, 2014.

(51) Int. Cl.
*C12Q 1/68* (2006.01)
(52) U.S. Cl.
CPC .................................. *C12Q 1/6848* (2013.01)
(58) Field of Classification Search
None
See application file for complete search history.

(56) References Cited

U.S. PATENT DOCUMENTS

| | | | |
|---|---|---|---|
| 2,014,761 A | 9/1935 | Faust | |
| 4,072,576 A | 2/1978 | Arwin et al. | |
| 5,602,042 A | 2/1997 | Farber | |
| 5,612,181 A | 3/1997 | Fourmentin-Guilbert | |
| 5,795,782 A | 8/1998 | Church et al. | |
| 5,834,197 A | 11/1998 | Parton | |
| 6,046,097 A | 4/2000 | Hsieh et al. | |
| 6,087,095 A | 7/2000 | Rosenthal et al. | |
| 6,210,891 B1 | 4/2001 | Nyren et al. | |
| 6,327,410 B1 | 12/2001 | Walt et al. | |
| 6,632,655 B1 | 10/2003 | Mehta et al. | |
| 6,833,246 B2 | 12/2004 | Balasubramanian | |
| 6,953,958 B2 | 10/2005 | Baxter et al. | |
| 7,081,192 B1 | 7/2006 | Wang et al. | |
| 7,223,540 B2 | 5/2007 | Pourmand et al. | |
| 7,242,241 B2 | 7/2007 | Toumazou et al. | |
| 7,270,981 B2 | 9/2007 | Armes et al. | |
| 7,282,370 B2 | 10/2007 | Bridgham et al. | |
| 7,291,496 B2 | 11/2007 | Holm-Kennedy | |
| 7,312,085 B2 | 12/2007 | Chou et al. | |
| 7,317,216 B2 | 1/2008 | Holm-Kennedy | |
| 7,323,305 B2 | 1/2008 | Leamon et al. | |
| 7,361,466 B2 | 4/2008 | Korlach et al. | |
| 7,399,590 B2 | 7/2008 | Piepenburg et al. | |
| 7,435,561 B2 | 10/2008 | Piepenburg et al. | |
| 7,485,428 B2 | 2/2009 | Armes et al. | |
| 7,615,382 B2 | 11/2009 | Wang et al. | |
| 7,645,596 B2 | 1/2010 | Williams et al. | |
| 7,649,358 B2 | 1/2010 | Toumazou et al. | |
| 7,666,598 B2 | 2/2010 | Piepenburg et al. | |
| 7,682,837 B2 | 3/2010 | Jain et al. | |
| 7,686,929 B2 | 3/2010 | Toumazou et al. | |
| 7,692,219 B1 | 4/2010 | Holm-Kennedy | |
| 7,695,907 B2 | 4/2010 | Miyahara et al. | |
| 7,763,427 B2 | 7/2010 | Piepenburg et al. | |
| 7,824,890 B2 | 11/2010 | Hoser et al. | |
| 7,875,440 B2 | 1/2011 | Williams et al. | |
| 7,888,013 B2 | 2/2011 | Miyahara et al. | |
| 7,932,034 B2 | 4/2011 | Esfandyarpour et al. | |
| 7,948,015 B2 | 5/2011 | Rothberg et al. | |
| 8,030,000 B2 | 10/2011 | Piepenburg et al. | |
| 8,062,848 B2 | 11/2011 | Goldstein et al. | |
| 8,062,850 B2 | 11/2011 | Piepenburg et al. | |
| 8,071,308 B2 | 12/2011 | Piepenburg et al. | |
| 8,114,591 B2 | 2/2012 | Toumazou et al. | |
| 8,128,796 B2 | 3/2012 | Ishige et al. | |
| 8,129,118 B2 | 3/2012 | Weindel et al. | |
| 8,137,569 B2 | 3/2012 | Harnack et al. | |
| 8,152,991 B2 | 4/2012 | Briman et al. | |
| 8,154,093 B2 | 4/2012 | Bradley et al. | |
| 8,173,401 B2 | 5/2012 | Chang et al. | |
| 8,179,296 B2 | 5/2012 | Kelly et al. | |
| 8,257,925 B2 | 9/2012 | Brown et al. | |
| 8,301,394 B2 | 10/2012 | Chen et al. | |
| 8,426,134 B2 | 4/2013 | Piepenburg et al. | |
| 8,460,875 B2 | 6/2013 | Armes et al. | |
| 8,518,670 B2 | 8/2013 | Goldstein et al. | |
| 8,574,846 B2 | 11/2013 | Piepenburg et al. | |
| 8,580,507 B2 | 11/2013 | Piepenburg et al. | |
| 8,585,973 B2 | 11/2013 | Esfandyarpour | |
| 8,637,253 B2 | 1/2014 | Piepenburg et al. | |

(Continued)

FOREIGN PATENT DOCUMENTS

| | | |
|---|---|---|
| CN | 1337580 A | 2/2002 |
| CN | 101120098 A | 2/2008 |

(Continued)

OTHER PUBLICATIONS

Notice of allowance dated Mar. 28, 2016 for U.S. Appl. No. 13/481,858.
Co-pending U.S. Appl. No. 14/835,070, filed Aug. 25, 2015.
Co-pending U.S. Appl. No. 14/859,725, filed Sep. 21, 2015.
Edman; et al., "Electric field directed nucleic acid hybridization on microchips.", Dec. 15, 1997, 25(24), 4907-14.
"Notice of allowance dated Aug. 25, 2015 for U.S. Appl. No. 14/596,111."

(Continued)

*Primary Examiner* — David Thomas

(74) *Attorney, Agent, or Firm* — Wilson Sonsini Goodrich & Rosati

(57) ABSTRACT

The disclosure provides methods and systems for nucleic acid amplification including isothermal nucleic acid amplification.

41 Claims, 12 Drawing Sheets

(56) References Cited

U.S. PATENT DOCUMENTS

| | | |
|---|---|---|
| 8,673,560 B2 | 3/2014 | Leamon et al. |
| 8,969,002 B2 | 3/2015 | Esfandyarpour et al. |
| 9,150,915 B2 | 10/2015 | Esfandyarpour et al. |
| 9,184,099 B2 | 11/2015 | Baghbani-Parizi et al. |
| 9,187,783 B2 | 11/2015 | Esfandyarpour et al. |
| 9,274,077 B2 | 3/2016 | Esfandyarpour et al. |
| 2002/0132245 A1 | 9/2002 | Boles et al. |
| 2002/0148739 A2 | 10/2002 | Liamos et al. |
| 2003/0209432 A1 | 11/2003 | Choong et al. |
| 2004/0014201 A1 | 1/2004 | Kim et al. |
| 2004/0033492 A1 | 2/2004 | Chen |
| 2004/0197793 A1 | 10/2004 | Hassibi et al. |
| 2005/0009022 A1 | 1/2005 | Weiner et al. |
| 2005/0019784 A1 | 1/2005 | Su et al. |
| 2005/0032076 A1 | 2/2005 | Williams et al. |
| 2006/0008824 A1 | 1/2006 | Ronaghi et al. |
| 2006/0105373 A1 | 5/2006 | Pourmand et al. |
| 2006/0222569 A1 | 10/2006 | Barten et al. |
| 2007/0132043 A1 | 6/2007 | Bradley et al. |
| 2007/0184463 A1 | 8/2007 | Molho et al. |
| 2007/0275375 A1 | 11/2007 | Van Eijk et al. |
| 2008/0009420 A1 | 1/2008 | Schroth et al. |
| 2008/0032295 A1 | 2/2008 | Toumazou et al. |
| 2008/0161200 A1 | 7/2008 | Yu et al. |
| 2008/0166727 A1 | 7/2008 | Esfandyarpour et al. |
| 2008/0171325 A1 | 7/2008 | Brown et al. |
| 2008/0176817 A1 | 7/2008 | Zhou et al. |
| 2008/0187915 A1 | 8/2008 | Polonsky et al. |
| 2008/0241841 A1 | 10/2008 | Murakawa et al. |
| 2008/0286762 A1 | 11/2008 | Miyahara et al. |
| 2008/0302732 A1 | 12/2008 | Soh et al. |
| 2008/0318243 A1 | 12/2008 | Haga et al. |
| 2009/0005259 A1 | 1/2009 | Drmanac |
| 2009/0026082 A1 | 1/2009 | Rothberg et al. |
| 2009/0029385 A1 | 1/2009 | Christians et al. |
| 2009/0032401 A1 | 2/2009 | Ronaghi et al. |
| 2009/0048124 A1 | 2/2009 | Leamon et al. |
| 2009/0127589 A1 | 5/2009 | Rothberg et al. |
| 2009/0166221 A1 | 7/2009 | Ishige et al. |
| 2009/0170716 A1 | 7/2009 | Su et al. |
| 2009/0170724 A1 | 7/2009 | Balasubramanian et al. |
| 2009/0181385 A1 | 7/2009 | McKernan et al. |
| 2009/0191594 A1 | 7/2009 | Ohashi |
| 2010/0035252 A1 | 2/2010 | Rothberg et al. |
| 2010/0072080 A1 | 3/2010 | Karhanek et al. |
| 2010/0078325 A1 | 4/2010 | Oliver |
| 2010/0112588 A1 | 5/2010 | Farinas et al. |
| 2010/0137143 A1 | 6/2010 | Rothberg et al. |
| 2010/0151479 A1 | 6/2010 | Toumazou et al. |
| 2010/0159461 A1 | 6/2010 | Toumazou et al. |
| 2010/0163414 A1 | 7/2010 | Gillies et al. |
| 2010/0167938 A1 | 7/2010 | Su et al. |
| 2010/0188073 A1 | 7/2010 | Rothberg et al. |
| 2010/0197507 A1 | 8/2010 | Rothberg et al. |
| 2010/0209922 A1 | 8/2010 | Williams et al. |
| 2010/0255595 A1 | 10/2010 | Toumazou et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0317531 A1 | 12/2010 | Balasubramanian et al. |
| 2010/0330570 A1 | 12/2010 | Vander Horn et al. |
| 2011/0039266 A1 | 2/2011 | Williams et al. |
| 2011/0117026 A1 | 5/2011 | Tseng et al. |
| 2011/0118139 A1 | 5/2011 | Mehta et al. |
| 2011/0123991 A1 | 5/2011 | Hoser |
| 2011/0159481 A1 | 6/2011 | Liu et al. |
| 2011/0171655 A1 | 7/2011 | Esfandyarpour et al. |
| 2011/0177498 A1 | 7/2011 | Clarke et al. |
| 2011/0183321 A1 | 7/2011 | Williams et al. |
| 2011/0195253 A1 | 8/2011 | Hinz et al. |
| 2011/0195459 A1 | 8/2011 | Hinz et al. |
| 2011/0201057 A1 | 8/2011 | Carr et al. |
| 2011/0201506 A1 | 8/2011 | Hinz et al. |
| 2011/0217697 A1 | 9/2011 | Rothberg et al. |
| 2011/0230375 A1 | 9/2011 | Rothberg et al. |
| 2011/0241081 A1 | 10/2011 | Rothberg et al. |
| 2011/0247933 A1 | 10/2011 | Rothberg et al. |
| 2011/0248319 A1 | 10/2011 | Rothberg et al. |
| 2011/0248320 A1 | 10/2011 | Rothberg et al. |
| 2011/0259745 A1 | 10/2011 | Dehlinger et al. |
| 2011/0263463 A1 | 10/2011 | Rothberg et al. |
| 2011/0287432 A1 | 11/2011 | Wong et al. |
| 2011/0287945 A1 | 11/2011 | Rothberg et al. |
| 2011/0294115 A1 | 12/2011 | Williams et al. |
| 2011/0311979 A1 | 12/2011 | Brown et al. |
| 2012/0013392 A1 | 1/2012 | Rothberg et al. |
| 2012/0021918 A1 | 1/2012 | Bashir et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0061255 A1 | 3/2012 | Rothberg et al. |
| 2012/0061256 A1 | 3/2012 | Rothberg et al. |
| 2012/0061733 A1 | 3/2012 | Rothberg et al. |
| 2012/0065093 A1 | 3/2012 | Rothberg et al. |
| 2012/0071363 A1 | 3/2012 | Rothberg et al. |
| 2012/0085660 A1 | 4/2012 | Rothberg et al. |
| 2012/0088682 A1 | 4/2012 | Rothberg et al. |
| 2012/0094871 A1 | 4/2012 | Hinz et al. |
| 2012/0129173 A1 | 5/2012 | Piepenburg et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0135893 A1 | 5/2012 | Drmanac et al. |
| 2012/0138460 A1 | 6/2012 | Baghbani-Parizi et al. |
| 2012/0156728 A1 | 6/2012 | Li et al. |
| 2012/0157322 A1 | 6/2012 | Myllykangas et al. |
| 2012/0173159 A1 | 7/2012 | Davey et al. |
| 2012/0175252 A1 | 7/2012 | Toumazou et al. |
| 2012/0222496 A1 | 9/2012 | Mamigonians |
| 2012/0258456 A1 | 10/2012 | Armes et al. |
| 2012/0258499 A1 | 10/2012 | Piepenburg et al. |
| 2012/0264617 A1 | 10/2012 | Pettit |
| 2012/0295819 A1 | 11/2012 | Leamon et al. |
| 2012/0302454 A1 | 11/2012 | Esfandyarpour |
| 2012/0322113 A1 | 12/2012 | Erlander et al. |
| 2013/0005613 A1 | 1/2013 | Leamon et al. |
| 2013/0023011 A1 | 1/2013 | Leamon et al. |
| 2013/0034880 A1 | 2/2013 | Oldham |
| 2013/0059290 A1 | 3/2013 | Armes |
| 2013/0059762 A1 | 3/2013 | Leamon et al. |
| 2013/0090860 A1 | 4/2013 | Sikora et al. |
| 2013/0096013 A1 | 4/2013 | Esfandyarpour et al. |
| 2013/0109577 A1 | 5/2013 | Korlach et al. |
| 2013/0203634 A1 | 8/2013 | Jovanovich et al. |
| 2013/0225421 A1 | 8/2013 | Li et al. |
| 2013/0231254 A1 | 9/2013 | Kawashima et al. |
| 2013/0281307 A1 | 10/2013 | Li et al. |
| 2014/0045701 A1 | 2/2014 | Esfandyarpour et al. |
| 2014/0057339 A1 | 2/2014 | Esfandyarpour et al. |
| 2014/0073531 A1 | 3/2014 | Esfandyarpour |
| 2014/0099674 A1 | 4/2014 | Piepenburg et al. |
| 2014/0235457 A1 | 8/2014 | Esfandyarpour et al. |
| 2014/0329699 A1 | 11/2014 | Esfandyarpour |
| 2015/0148264 A1 | 5/2015 | Esfandyarpour et al. |
| 2015/0368707 A1 | 12/2015 | Esfandyarpour et al. |
| 2015/0376692 A1 | 12/2015 | Esfandyarpour et al. |
| 2016/0076097 A1 | 3/2016 | Esfandyarpour et al. |
| 2016/0077049 A1 | 3/2016 | Baghbani-Parizi et al. |
| 2016/0273032 A1 | 9/2016 | Esfandyarpour et al. |
| 2016/0340721 A1 | 11/2016 | Esfandyarpour |
| 2017/0073750 A1 | 3/2017 | Esfandyarpour et al. |

FOREIGN PATENT DOCUMENTS

| | | |
|---|---|---|
| CN | 101848757 A | 9/2010 |
| CN | 102980922 A | 3/2013 |
| EP | 0676623 A2 | 10/1995 |
| EP | 1499738 B1 | 7/2008 |

(56) References Cited

FOREIGN PATENT DOCUMENTS

| EP | 1992706 A2 | 11/2008 |
|---|---|---|
| EP | 2290096 A2 | 3/2011 |
| EP | 2336361 A2 | 6/2011 |
| EP | 2428588 A2 | 3/2012 |
| EP | 2287341 B1 | 2/2013 |
| EP | 1759012 B1 | 5/2013 |
| EP | 2660336 A1 | 11/2013 |
| JP | 2006512583 A | 4/2006 |
| JP | 2008525822 A | 7/2008 |
| JP | 2010517040 A | 5/2010 |
| JP | 2010517041 A | 5/2010 |
| JP | 2010518401 A | 5/2010 |
| WO | WO-0118246 A1 | 3/2001 |
| WO | WO-0137958 A2 | 5/2001 |
| WO | WO-0142508 A2 | 6/2001 |
| WO | WO-0227909 A2 | 4/2002 |
| WO | WO-02061146 A1 | 8/2002 |
| WO | WO-2005008450 A2 | 1/2005 |
| WO | WO-2005108612 A2 | 11/2005 |
| WO | WO-2005121363 A2 | 12/2005 |
| WO | WO-2007041619 A2 | 4/2007 |
| WO | WO-2007098049 A2 | 8/2007 |
| WO | WO-2008076406 A2 | 6/2008 |
| WO | WO-2009012112 A1 | 1/2009 |
| WO | WO-2009052348 A2 | 4/2009 |
| WO | WO-2009074926 A1 | 6/2009 |
| WO | WO-2009122159 A2 | 10/2009 |
| WO | WO-2009150467 A1 | 12/2009 |
| WO | WO-2010008480 A2 | 1/2010 |
| WO | WO-2010026488 A2 | 3/2010 |
| WO | WO-2010037085 A1 | 4/2010 |
| WO | WO-2010041231 A2 | 4/2010 |
| WO | WO-2010047804 A1 | 4/2010 |
| WO | WO-2010075188 A2 | 7/2010 |
| WO | WO-2010138187 A1 | 12/2010 |
| WO | WO-2010141940 A1 | 12/2010 |
| WO | WO-2011106556 A2 | 9/2011 |
| WO | WO-2012047889 A2 | 4/2012 |
| WO | WO-2012166742 A2 | 12/2012 |
| WO | WO-2013082619 A1 | 6/2013 |
| WO | WO-2013188582 A1 | 12/2013 |
| WO | WO-2014012107 A2 | 1/2014 |
| WO | WO-2014043143 A1 | 3/2014 |

OTHER PUBLICATIONS

"Notice of allowance dated Sep. 1, 2015 for U.S. Appl. No. 14/596,111."
"Office action dated Oct. 7, 2015 for U.S. Appl. No. 13/838,816."
Sosnowski; et al., "Rapid determination of single base mismatch mutations in DNA hybrids by direct electric field control.", Feb. 18, 1997, 94(4), 1119-23.
Zhang; et al., "Dielectrophoresis for manipulation of micro/nano particles in microfluidic systems.", Jan. 2010, 396(1), 401-20.
Cagnin, et al. Overview of electrochemical DNA biosensors: new approaches to detect the expression of life. Sensors (Basel). 2009;9(4):3122-48. doi: 10.3390/s90403122. Epub Apr. 24, 2009.
Daniels, et al. Label-Free Impedance Biosensors: Opportunities and Challenges. Electroanalysis. May 16, 2007;19(12):1239-1257.
Daniels, et al. Simultaneous Measurement of Nonlinearity and Electrochemical Impedance for Protein Sensing Using Two-Tone Excitation. 30th Annual International IEEE EMBS Conference. Vancouver, British Columbia, Canada, Aug. 20-24, 2008. 5753-5756.
Esfandyarpour, et al. 3D modeling of impedance spectroscopy for protein detection in nanoneedle biosensors. Proceedings of the COMSOL Conference 2007, Boston.
Esfandyarpour, et al. A Novel Nanoneedle Biosensor for DNA Sequencing (abstract). Dec. 31, 2008. Available at http://www.nsti.org/Nanotech2008/showabstract.html?absno=1522.
European search report and search opinion dated Jan. 5, 2015 for EP Application No. 12792216.9.

European search report and search opinion dated Mar. 12, 2014 for EP Application No. 11831452.5.
Finn, et al. Efficient incorporation of positively charged 2', 3'-dideoxynucleoside-5'-triphosphates by DNA polymerases and their application in 'direct-load' DNA sequencing. Nucleic Acids Res. Aug. 15, 2003;31(16):4769-78.
Hollis, et al. Structure of the gene 2.5 protein, a single-stranded DNA binding protein encoded by bacteriophage T7. Proc Natl Acad Sci U S A. Aug. 14, 2001;98(17):9557-62. Epub Jul. 31, 2001.
International search report and written opinion dated Feb. 26, 2013 for PCT/US2012/039880.
International search report and written opinion dated Mar. 19, 2013 for PCT/US2012/067645.
International search report and written opinion dated Apr. 13, 2012 for PCT/US2011/054769.
International search report and written opinion dated Aug. 21, 2014 for PCT Application No. PCT/US2014/027544.
Javanmard, et al. A microfluidic platform for electrical detection of DNA hybridization. Sens Actuators B Chem. May 20, 2011;154(1):22-27. Epub Mar. 30, 2010.
Kitano, et al. Molecular structure of RNA polymerase and its complex with DNA. J Biochem. Jan. 1969;65(1):1-16.
Lee, et al. Ion-sensitive field-effect transistor for biological sensing. Sensors (Basel). 2009;9(9):7111-31. doi: 10.3390/s90907111. Epub Sep. 7, 2009.
Manickam, et al. A CMOS Electrochemical Impedance Spectroscopy (EIS) Biosensor Array. IEEE Trans Biomed Circuits Syst. Dec. 2010;4(6):379-90. doi: 10.1109/TBCAS.2010.2081669.
Margulies, et al. Genome sequencing in microfabricated high-density picolitre reactors. Nature. Sep. 15, 2005;437(7057):376-80. Epub Jul. 31, 2005.
"Notice of allowance dated Jun. 3, 2015 for U.S. Appl. No. 14/596,111."
Notice of allowance dated Nov. 21, 2014 for U.S. Appl. No. 13/632,513.
Office action dated Jan. 28, 2014 for U.S. Appl. No. 13/838,816.
Office action dated Jan. 29, 2014 for U.S. Appl. No. 13/481,858.
Office action dated Jan. 30, 2015 for U.S. Appl. No. 13/481,858.
Office action dated Apr. 9, 2015 for U.S. Appl. No. 14/596,111.
Office action dated May 1, 2015 for U.A. Appl. No. 13/824,129.
Office action dated Jul. 18, 2013 for U.S. Appl. No. 13/481,858.
Office action dated Jul. 23, 2014 for U.S. Appl. No. 13/824,129.
Office action dated Jul. 25, 2014 for U.S. Appl. No. 13/481,858.
Office action dated Sep. 2, 2014 for U.S. Appl. No. 13/632,513.
Office action dated Nov. 5, 2013 for U.S. Appl. No. 13/632,513.
Office action dated Dec. 19, 2014 for U.S. Appl. No. 13/838,816.
Piepenburg, et al. DNA detection using recombination proteins. PLoS Biol. Jul. 2006;4(7):e204.
Ren, et al. Rapid and sensitive detection of hepatitis B virus 1762T/1764A double mutation from hepatocellular carcinomas using LNA-mediated PCR clamping and hybridization probes. Journal of Virological Methods. 2009; 158:24-29.
Sabounchi, et al. Sample concentration and impedance detection on a microfluidic polymer chip. Biomed Microdevices. Oct. 2008;10(5):661-70. doi: 10.1007/s10544-008-9177-4.
Senapati, et al. A nonamembrane-based nucleic acid sensing platform for portable diagnostics. Topics in Current Chemistry. 2011; 304:153-169.
U.S. Appl. No. 13/397,581, filed Feb. 15, 2012.
U.S. Appl. No. 13/824,129, filed Mar. 15, 2013.
U.S. Appl. No. 13/838,816, filed Mar. 15, 2013.
U.S. Appl. No. 14/119,859, filed Nov. 22, 2013.
U.S. Appl. No. 14/361,902, filed May 30, 2014.
U.S. Appl. No. 14/596,111, filed Jan. 13, 2015.
Voelkerding, et al. Next generation sequencing: from basic research to diagnostics. Clin. Chem. 2009; 55(4):641-658.
Andreotti, et al. Immunoassay of infectious agents. Biotechniques. Oct. 2003;35(4):850-9.
Bell, et al. Detection of Bacillus anthracis DNA by LightCycler PCR. J Clin Microbiol. Aug. 2002;40(8):2897-902.
Boo, et al. Electrochemical nanoneedle biosensor based on multiwall carbon nanotube. Anal Chem. Jan. 15, 2006;78(2):617-20.

(56) References Cited

OTHER PUBLICATIONS

Esfandyarpour, et al. 3D Modeling of Impedance Spectroscopy for Protein Detection in Nanoneedle Biosensors. Proceedings of the International COMSOL Conference 2007, Boston, MA, USA, pp. 169-173 (Oct. 4-6, 2007).
Esfandyarpour, et al. Geometrical Optimization of Pyrophosphate Concentration in Thermosequencing Platform for DNA Sequencing. Proceedings of the COMSOL Conf. 2007, Boston.
Gao, et al. Silicon nanowire arrays for label-free detection of DNA. Anal Chem. May 1, 2007;79(9):3291-7. Epub Apr. 4, 2007.
Guiducci, et al. A Biosensor for Direct Detection of DNA Sequences Based on Capacitance Measurements. ESSDERC 2002, pp. 479-482.
Javanmard, et al. Electrical Detection of Proteins and DNA Using Bioactivated Microfluidic Channels: Theoretical and Experimental Considerations. J Vac Sci Technol B Microelectron Nanometer Struct Process Meas Phenom. Nov. 2009;27(6):3099-3103.
Notice of Allowance dated May 12, 2017 for U.S. Appl. No. 14/653,230.
Office Action dated Feb. 14, 2017 for U.S. Appl. No. 14/653,230.
Office Action dated Apr. 5, 2017 for U.S. Appl. No. 14/859,725.
Office Action dated Apr. 24, 2017 for U.S. Appl. No. 14/119,859.
Patolsky, et al. Electrical detection of single viruses. Proc Natl Acad Sci U S A. Sep. 28, 2004;101(39):14017-22. Epub Sep. 13, 2004.
Patolsky, et al. Fabrication of silicon nanowire devices for ultrasensitive, label-free, real-time detection of biological and chemical species. Nat Protoc. 2006;1(4):1711-24.
Roosen-Runge, et al. Protein diffusion in crowded electrolyte solutions. Biochim Biophys Acta. Jan. 2010;1804(1):68-75. doi: 10.1016/j.bbapap.2009.07.003. Epub Jul. 17, 2009.
Safir, et al. Fabrication of an insulated probe on a self-assembled metallic nanowire for electrochemical probing in cells. IEEE 2006, pp. 898-900.
Yazdanpanah, et al. Selective self-assembly at room temperature of individual freestanding Ag2Ga alloy nanoneedles. J. Appl. Phys. 98, pp. 073510-073517 (2005).
Zheng, et al. Multiplexed electrical detection of cancer markers with nanowire sensor arrays. Nat Biotechnol. Oct. 2005;23(10):1294-301. Epub Sep. 18, 2005.
Didion; et al., "Invaders: Recognition of Double-Stranded DNA by Using Duplexes Modified with Interstrand Zippers of 2'-O-(Pyren-1-yl)methyl-ribonucleotides.", doi: 10.1002/cbic.201300414. Epub Aug. 23, 2013., Sep. 2, 2013, 14(13), 1534-1538.
International search report and written opinion dated Oct. 26, 2015 for PCT/US2015/026135.
Brouns; et al., "Small CRISPR RNAs guide antiviral defence in prokaryotes.", Aug. 15, 2008, 321(5891), 960-4.
Carte; et al., "Cas6 is an endoribonuclease that generates guide RNAs for invader defence in prokaryotes.", Dec. 15, 2008, 22(24), 3489-96.
Cho; et al., "Bis-aptazyme sensors for hepatitis C virus replicase and helicase without blank signal.", Nov. 27, 2005, 33(20), e177.
Co-pending U.S. Appl. No. 14/653,230, filed Jun. 17, 2015.
Dimov; et al., "Stand-alone self-powered integrated microfluidic blood analysis system (SIMBAS).", Mar. 7, 2011, 11(5), 845-50.
Ellington; et al., "In vitro selection of RNA molecules that bind specific ligands.", Aug. 30, 1990, 346(6287), 818-22.

"European search report and search opinion dated Jul. 13, 2015 for EP Application No. 12852490.7."
Gardeniers; et al., "Silicon micromachined hollow microneedles for transdermal liquid transport.", 2003, 12(6), 855-862.
Haurwitz; et al., "Sequence- and structure-specific RNA processing by a CRISPR endonuclease.", Sep. 10, 2010, 329(5997), 1355-8.
Kaushik; et al., "Lack of pain associated with microfabricated microneedles.", Feb. 2001, 92(2), 502-4.
Kim; et al., "Replication of DNA microarrays prepared by in situ oligonucleotide polymerization and mechanical transfer.", Oct. 1, 2007, 79(19), 7267-74.
Kunin; et al., "Evolutionary conservation of sequence and secondary structures in CRISPR repeats.", 2007, 8(4), R61.
Kurosaki; et al., "Rapid and simple detection of Ebola virus by reverse transcription-loop-mediated isothermal amplification.", Apr. 2007, 141(1), 78-83.
Lin; et al., "Replication of DNA microarrays from zip code masters.", Mar. 15, 2006, 128(10), 3268-72.
Liu; et al., "Immobilization of DNA onto poly(dimethylsiloxane) surfaces and application to a microelectrochemical enzyme-amplified DNA hybridization assay.", Jul. 6, 2004, 20(14), 5905-10.
Makarova; et al., "A putative RNA-interference-based immune system in prokaryotes: computational analysis of the predicted enzymatic machinery, functional analogies with eukaryotic RNAi, and hypothetical mechanisms of action.", Mar. 16, 2006, 1:7, 26 pages.
"Notice of allowance dated Jul. 1, 2015 for U.S. Appl. No. 13/824,129."
"Notice of allowance dated Jul. 13, 2015 for U.S. Appl. No. 14/596,111."
Notomi; et al., "Loop-mediated isothermal amplification of DNA.", Jun. 15, 2000, 28(12), E63.
Sivamani; et al., "Microneedles and transdermal applications.", Jan. 2007, 4(1), 19-25.
Terns; et al., "CRISPR-based adaptive immune systems.", Jun. 2011, 14(3), 321-7.
Van; Der Oost et al., "CRISPR-based adaptive and heritable immunity in prokaryotes.", Aug. 2009, 34(8), 401-7.
Wang; et al., "Interaction of the Cas6 riboendonuclease with CRISPR RNAs: recognition and cleavage.", Feb. 9, 2011, 19(2), 257-64.
Co-pending U.S. Appl. No. 15/183,406, filed Jun. 15, 2016.
Notice of allowance dated Dec. 15, 2015 for U.S. Appl. No. 13/838,816.
Office action dated Dec. 17, 2015 for U.S. Appl. No. 13/481,858.
Office action dated Dec. 17, 2015 for U.S. Appl. No. 14/835,070.
Notice of allowance dated Dec. 3, 2015 for U.S. Appl. No. 13/838,816.
Office action dated Apr. 6, 2016 for U.S. Appl. No. 14/835,070.
Notice of allowance dated May 19, 2016 for U.S. Appl. No. 13/481,858.
Co-penidng U.S. Appl. No. 15/655,616, filed Jul. 20, 2017.
Notice of Allowance dated Jul. 31, 2017 for U.S. Appl. No. 14/119,859.
Notice of Allowance dated Sep. 8, 2017 for U.S. Appl. No. 14/653,230.
Office Action dated Sep. 1, 2017 for U.S. Appl. No. 14/361,902.
Rothberg, et al. An integrated semiconductor device enabling non-optical genome sequencing. Nature. Jul. 20, 2011; 475(7356); pp. 348-52. With Supplementary Information, 25 pages.

FIG. 5
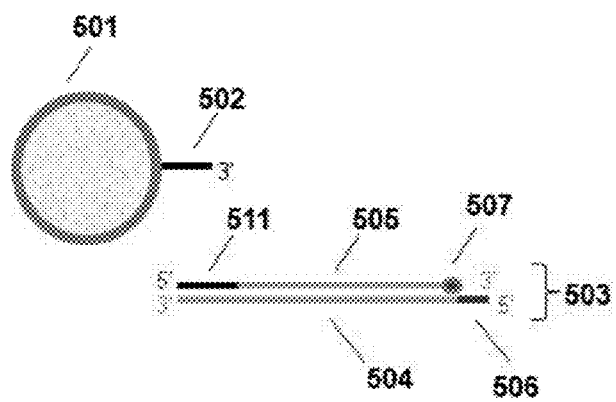
500 — Support 501 coupled to primer 502 and double-stranded nucleic acid 503 comprising template nucleic acid 504 and complementary nucleic acid 505
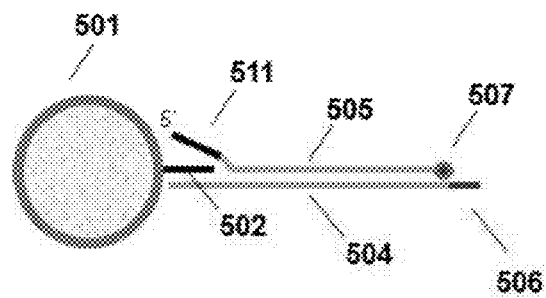
510 — Primer 502 invasion
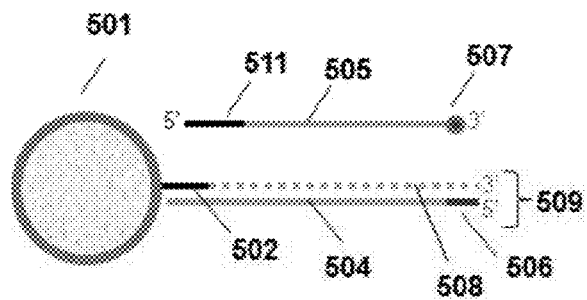
520 — Primer 502 extension and release of complementary nucleic acid 505

FIG. 7
700 Support 701 coupled to primer 702, double-stranded nucleic acid 703 comprising template nucleic acid 704 and complementary nucleic acid 705, and oligonucleotide 712
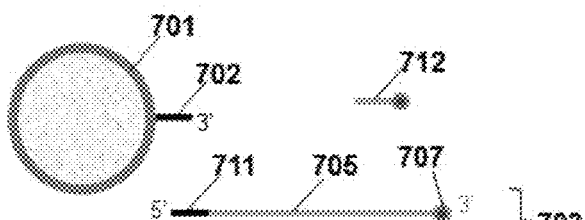
710 Oligonucleotide 712 invasion and partial denaturation of double-stranded molecule 703
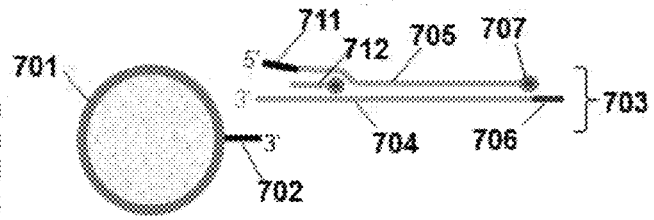
720 Primer 702 coupling
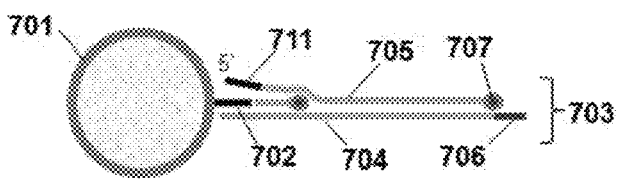
730 Primer 702 extension and release of complementary nucleic acid 705
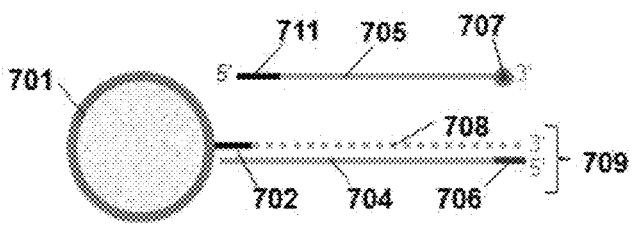
740
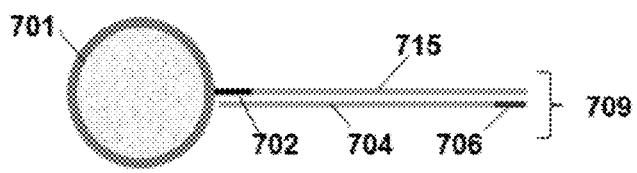

FIG. 10
A
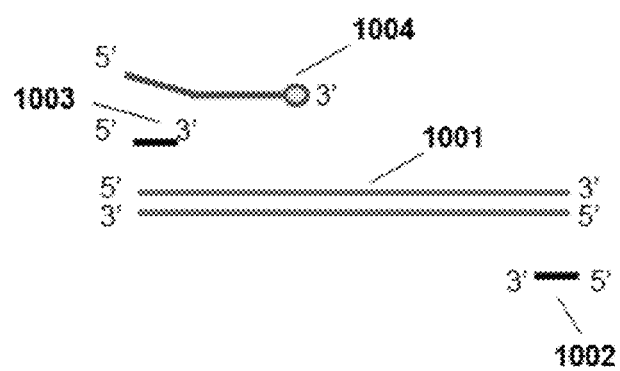
B
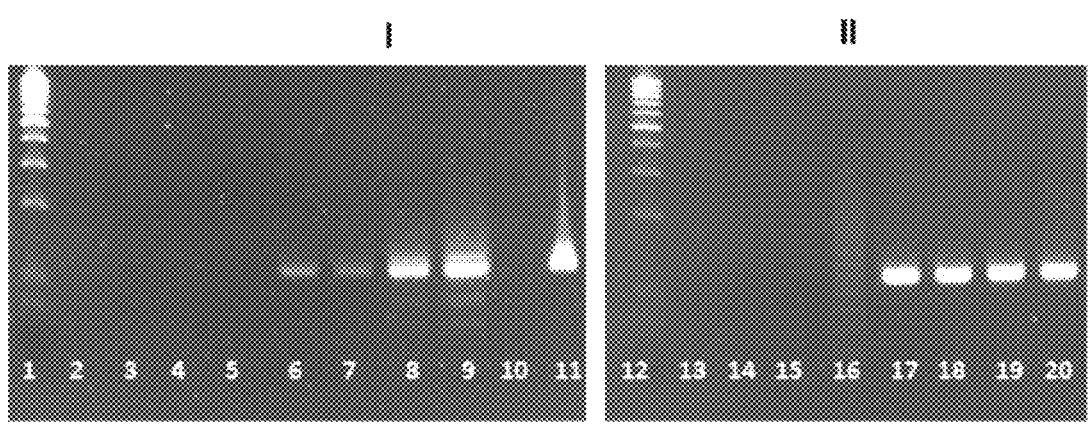

```
                           SEQUENCE LISTING

<160> NUMBER OF SEQ ID NOS: 14

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccatctcatc cc                                                         12

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccatctcatc cct                                                        13

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccatctcatc cctg                                                       14

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccatctcatc cctgc                                                      15

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 5
cctatcccct gt                                                               12

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cctatcccct gtgtg                                                            15

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cctatcccct gtgtgcct                                                         18

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cctaatctta gcgccttggc agtctcagag accactaact gcgtatcaac c                    51

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cctaatctta cttggcagtc tcagagacca ctaactgcgt atcaacc                         47

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctcattggat cgccttggca gtctcagaga ccactaactg cgtatcaac                       49

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
cattggatcg tgccttggca gtctcagaga ccactaactg cgtatcaac            49

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cactattgtc tcgtgtctcc gactcagtga cctgcctcaa cctcctgtc            49

<210> SEQ ID NO 13
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
cctatcccct gtgtgccttg gcagtctcag agaccactaa ctgcgtatca acccaaccaa    60 cccctttaa aattttttcc ccccaaaaaa ctgagtcgga gacacgcagg gatgagatgg    120

<210> SEQ ID NO 14
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
ccatctcatc cctgcgtgtc tccgactcag tgacctgcct caacctcctg tcaatgctgg    60
cggcggctct ggtggtggtt ctggtggcgg ctctgagggt tgatacgcag ttagtggtct   120
ctgagactgc caaggcacac aggggatagg                                   150
```

METHODS AND SYSTEMS FOR NUCLEIC ACID AMPLIFICATION

CROSS-REFERENCE

This application claims priority to U.S. Provisional Patent Application No. 61/981,435 filed on Apr. 18, 2014 and U.S. Provisional Patent Application No. 62/025,626 filed on Jul. 17, 2014, which applications are incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on May 4, 2015, is named 42808726201SL.txt and is 3,830 bytes in size.

BACKGROUND

The goal to elucidate the entire human genome has created interest in technologies for rapid deoxyribonucleic acid (DNA) and other nucleic acid sequencing, both for small and large scale applications. Important parameters for nucleic acid sequencing include sequencing speed, length of sequence that can be read during a single sequencing run, and amount of nucleic acid template required to generate sequencing information. Large scale genome projects are currently too expensive to realistically be carried out for a large number of subjects (e.g., patients). Furthermore, as knowledge of the genetic basis for human diseases increases, there will be an ever-increasing need for accurate, high-throughput DNA sequencing that is affordable for clinical applications. Practical methods for determining the base pair sequences of single molecules of nucleic acids, preferably with high speed and long read lengths, may provide the necessary measurement capability.

Nucleic acid sequencing and other diagnostic technologies can rely heavily on amplification of individual nucleic acid molecules. For example, nucleic acid sequencing may rely on amplification of a nucleic acid prior to sequencing, in order to generate a sufficient amount of the nucleic acid for sequencing. In some cases, amplification methods suitable for segregating the amplification of a nucleic acid in a sample from the amplification of other nucleic acids in the sample may be desirable, including cases where multiple nucleic acids are sequenced simultaneously. Such amplification methods include, for example, clonal amplification. Moreover, isothermal amplification methods may also be desirable in order to avoid the need for thermal cycling equipment and/or the need to subject a sample to varied temperature conditions that can result in increased times necessary for completing nucleic acid amplification.

SUMMARY

Recognized herein is the need for improved methods of nucleic acid amplification.

An aspect of the disclosure provides a method for amplifying a nucleic acid sample that comprises providing a support comprising a first primer and a second primer and coupling the first primer to a first single-stranded nucleic acid molecule that is derived from the nucleic acid sample. Next, a first primer extension reaction can be performed using the first primer to generate a first double-stranded nucleic acid molecule comprising the first single-stranded nucleic acid molecule and a second single-stranded nucleic acid molecule that is complementary to at least a portion of the first single-stranded nucleic acid molecule. The first double-stranded nucleic acid molecule can then be at least partially denatured by binding an invader species to at least a portion of the first or second single-stranded nucleic acid molecule. The invader species can be different from the second primer and binding of the invader species to at least a portion of the first or second single-stranded nucleic acid can expose a segment of the first single-stranded nucleic acid molecule that is complementary to the second primer. Next, the second primer can be coupled to the segment of the first single-stranded nucleic acid molecule. A second primer extension reaction can be performed using the second primer to generate a second double-stranded nucleic acid molecule comprising the first single-stranded nucleic acid molecule and a third single-stranded nucleic acid molecule that is complementary to at least a portion of the first single-stranded nucleic acid molecule. The second primer extension reaction can separate the second single-stranded nucleic acid molecule from the first single-stranded nucleic acid molecule.

In some embodiments, the support can be a bead, an array pixel, a sensor, a particle, or an electrode. Moreover, in some embodiments, the first primer and/or the second primer can have a length of at most 30 nucleotides, at most 20 nucleotides, or at most 10 nucleotides. The first primer can be the same as the second primer or the first primer can be different from the second primer. In some examples, the invader species may be an oligonucleotide that has a length of at least 30 nucleotides, has a length of at least 40 nucleotides, or a length of at least 50 nucleotides. The invader species can be different from the first primer or can be the same as the first primer.

Additionally, non-limiting examples of an invader species include an oligonucleotide, a primer, a nucleic acid comprising a locked nucleic acid (LNA), a nucleic acid comprising a peptide nucleic acid (PNA), and a sequence-specific single-stranded nucleic acid binding protein. In some embodiments, the invader species can be an oligonucleotide that cannot be extended via the incorporation of additional nucleotides. Extension of an oligonucleotide, for example, can be blocked via a dideoxynucleotide (ddNTP).

In some cases, an invader species can be an oligonucleotide that is bound to at least a portion of the first or second single-stranded nucleic acid molecule with the aid of a recombinase. Non-limiting examples of recombinases include Cre recombinase, Hin recombinase, RecA recombinase, RAD51 recombinase, Tre recombinase, FLP recombinase, UvsX recombinase, DMC1 recombinase, variants thereof, modified products thereof, homologues thereof, derivatives thereof, and combinations thereof. In addition, the first and/or second primer extension reaction can be completed with the aid of a strand-displacing polymerase. Non-limiting examples of strand-displacing polymerases include Bsu polymerase I, Large Fragment (*Bacillus subtilits*), Bst polymerase, PolI polymerase, phi 29 polymerase, Large Fragment (*Bacillus stearothermophilus*), *Staphylococcus aureus* polymerase, Klenow Fragment (3'→5' exo-), variants thereof, modified products thereof, homologues thereof, derivatives thereof, and combinations thereof.

Moreover, the nucleic acid sample can be amplified isothermally and/or clonally amplified. Examples of a nucleic acid sample include deoxyribonucleic acid (DNA) or ribonucleic acid (RNA). In some embodiments, nucleic acid may not be released from the support during execution of the method. Furthermore, the first primer can be coupled to the first single-stranded nucleic acid molecule by annealing the first primer to the first single-stranded nucleic acid molecule.

The binding of the invader species can be completed with the aid of energy transfer. Energy may be transferred, for example, from a form of thermal energy and/or from a form of chemical energy. Chemical energy can be provided, for example, by adenosine triphosphate (ATP).

Further, a third primer can be coupled to the second single-stranded nucleic acid molecule and a third primer extension reaction can be performed using the third primer to generate a third double-stranded nucleic acid molecule that comprises the second single-stranded nucleic acid molecule and a fourth single-stranded nucleic acid molecule that is complementary to at least a portion of the second single-stranded nucleic acid molecule. The third primer can have, for example, a length of at most 30 nucleotides, at most 20 nucleotides, or at most 10 nucleotides. In some embodiments, the number of molecules of the third primer can be greater than the number of molecules of the first primer and the number of molecules of the second primer. In some embodiments, the third primer can be in solution or the support may comprise the third primer.

In some embodiments, the first single-stranded nucleic acid molecule can be coupled to the support via coupling of the first single-stranded nucleic acid molecule to a fourth primer that is coupled to the support. In some cases, the first single-stranded nucleic acid molecule can be coupled to the fourth primer via a covalent bond.

Additionally the method may comprise binding the invader species to at least a portion of the first single-stranded nucleic acid molecule and binding another invader species to at least a portion of the second single-stranded nucleic acid molecule. The binding of the other invader species can expose a segment of the second single-stranded nucleic acid that is complementary to the third primer. The third primer can be coupled to the second single-stranded nucleic acid molecule by coupling the third primer to the segment of the second single-stranded nucleic acid. In some embodiments, the other invader species can be the same as the third primer. In some embodiments, the other invader species can be different from the third primer. In some embodiments, the binding of the invader species and the other invader species can be completed with the aid of energy transfer. Energy may be transferred, for example, from a form of thermal energy and/or a form of chemical energy. In some embodiments, the invader species can be a first oligonucleotide and the other invader species can be a second oligonucleotide. In some examples, the first oligonucleotide and the second oligonucleotide cannot be extended via the incorporation of additional nucleotides. In some embodiments, the second primer extension reaction and the third primer extension reaction can be completed with the aid of a strand-displacing polymerase.

In some embodiments, a method for nucleic acid amplification or a portion a method for nucleic acid amplification (e.g., one or more denaturation phases, one or more primer coupling phases, one or more primer extension reactions, etc.) may be repeated for one or more cycles. In some cases, a method for nucleic acid amplification or a portion of a method for nucleic acid amplification (e.g., one or more denaturation phases, one or more primer coupling phases, one or more primer extension reactions, etc.) may be repeated for one or more cycles for each double-stranded nucleic acid molecule that is generated in the previous cycle. In some embodiments, a method for nucleic acid amplification or a portion a method for nucleic acid amplification (e.g., one or more denaturation phases, one or more primer coupling phases, one or more primer extension reactions, etc.) may be completed in at most 15 minutes, in at most 1 minute, or in at most 1 second. Moreover, in some cases, the first single-stranded nucleic acid molecule may be derived from a double-stranded nucleic acid molecule that is derived from the nucleic acid sample. In some cases, the first primer may be directly attached to the support. In some cases, the first primer can be coupled to the support via a linker attached to the support.

An additional aspect of the disclosure provides a method for amplifying a nucleic acid sample. A support comprising a first primer may be provided in addition to a first double-stranded nucleic acid molecule derived from the nucleic acid sample. The first double-stranded nucleic acid molecule may comprise a first single-stranded nucleic acid molecule and a second single-stranded nucleic acid molecule that is at least partially complementary to the first single-stranded nucleic acid molecule. The first double-stranded nucleic acid molecule may be at least partially denatured by binding a first invader species free from the support to at least a portion of the first or second single-stranded nucleic acid molecule, which binding exposes a segment of the first single-stranded nucleic acid molecule that is complementary to the first primer. The first primer may be coupled to the segment of the first single-stranded nucleic acid molecule and a first primer extension reaction may be performed, using the first primer, to generate a second double-stranded nucleic acid molecule. The second double-stranded nucleic acid molecule may comprise the first single-stranded nucleic acid molecule and a third single-stranded nucleic acid molecule that is complementary to at least a portion of the first single-stranded nucleic acid molecule. Moreover, the first primer extension reaction can separate the second single-stranded nucleic acid molecule from the first single-stranded nucleic acid molecule. In some cases, the first double-stranded nucleic acid molecule may be provided and denatured via the invader species in solution. In some cases, the first primer cannot function as an invader species.

In some cases, the method may further comprise at least partially denaturing the second double-stranded nucleic acid molecule by binding a second invader species free from the support to at least a portion of the first or third single-stranded nucleic acid molecule. The binding of the second invader species can expose a segment of the first single-stranded nucleic acid molecule that is complementary to a second primer. In some cases, the second primer can be provided and coupled to the segment of the first single-stranded nucleic acid molecule. A second primer extension reaction can be performed using the second primer to generate a second double-stranded nucleic acid molecule comprising the first single-stranded nucleic acid molecule and a fourth single-stranded nucleic acid molecule that is complementary to at least a portion of the first single-stranded nucleic acid molecule. Moreover, the second primer extension reaction can separate the third single-stranded nucleic acid molecule from the first single-stranded nucleic acid molecule. Furthermore, one or more steps of the method may be repeated to generate one or more additional double-stranded nucleic acid molecules coupled to the support.

In some cases, the first invader species and the second invader species may be the same invader species or, in other cases, may be different invader species. In some cases, the first primer and the second primer may have the same nucleic acid sequence or, in other cases, may have different nucleic acid sequences. In some cases, the first invader species and/or the second invader species may be for example, an oligonucleotide, a nucleic acid comprising a locked nucleic acid (LNA), a nucleic acid comprising a peptide nucleic acid (PNA), or a sequence-specific single-stranded nucleic acid binding protein. In some cases, at least one of the first invader species and second invader species may be an oligonucleotide that cannot be extended in a primer extension reaction. In some cases, the support may be, for example, a bead, an array pixel, a sensor, a particle, or an electrode. In some cases, the first primer may be directly attached to the support. In some cases, the first primer may be coupled to the support via a linker attached to the support. In some cases, the second single-stranded nucleic acid molecule may be blocked such that it cannot serve as a template in a primer extension reaction.

Furthermore, the first double-stranded nucleic acid molecule may be provided by subjecting a parent double-stranded nucleic acid molecule that is derived from the nucleic acid sample to one or more cycles of a nucleic acid amplification reaction. The first double-stranded nucleic acid molecule may be an amplicon of the parent double-stranded nucleic acid molecule generated during the one or more cycles of the nucleic acid amplification reaction. In some cases, the one or more cycles of the nucleic acid amplification reaction are completed with the aid of a second invader species. In some cases, the first invader species and the second invader species are the same invader species or, in other cases, are different invader species. In some cases, at least one of the first invader species and second invader species is an oligonucleotide that cannot be extended in a primer extension reaction. In some cases, the nucleic acid amplification reaction may be completed in solution and may be completed with the use of a solution-phase primer that is of the same sequence of the first primer.

In some cases, the first primer extension reaction may be completed with the aid of a strand-displacing polymerase. The strand-displacing polymerase may be, for example, Bsu polymerase I, Large Fragment (*Bacillus subtilits*), Bst polymerase, PolI polymerase, phi 29 polymerase, Large Fragment (*Bacillus stearothermophilus*), *Staphylococcus aureus* polymerase, Klenow Fragment (3'→5' exo-), a variant thereof, a modified product thereof, a homologue thereof, a derivative thereof, or a combination thereof.

In some cases, the first invader species may be an oligonucleotide that is bound to at least a portion of the first or second single-stranded nucleic acid molecule with the aid of a recombinase. The recombinase may be, for example, Cre recombinase, Hin recombinase, RecA recombinase, RAD51 recombinase, Tre recombinase, FLP recombinase, UvsX recombinase, DMC1 recombinase, a variant thereof, a modified product thereof, a homologue thereof, a derivative thereof, or a combination thereof. In some cases, the binding of the first invader species may be completed with the aid of energy transfer. Energy may be transferred, for example, from a form of chemical energy (e.g., provided by adenosine triphosphate (ATP)) and/or may be transferred from a form of thermal energy. In some cases, the nucleic acid sample may be amplified isothermally.

An additional aspect of the disclosure provides a method for amplifying a nucleic acid sample. A support comprising a first primer, a second primer separate from the first primer, and a first double-stranded nucleic acid molecule derived from the nucleic acid sample may be provided. The first double-stranded nucleic acid molecule may comprise a first single-stranded nucleic acid molecule and a second single-stranded nucleic acid molecule that is at least partially complementary to the first single-stranded nucleic acid molecule. The second-single-stranded nucleic acid molecule may also comprise a nucleic acid sequence that is at least partially complementary to the first primer. The first double-stranded nucleic acid molecule may be at least partially denatured by binding a first invader species free from the support to at least a portion of the first or second single-stranded nucleic acid molecule, which binding exposes a segment of the first single-stranded nucleic acid molecule that is complementary to the second primer. The second primer can be coupled to the segment of the first single-stranded nucleic acid molecule and a first primer extension reaction can be performed using the second primer to generate a second double-stranded nucleic acid molecule. The second double-stranded molecule may comprise the first single-stranded nucleic acid molecule and a third single-stranded nucleic acid molecule that is complementary to at least a portion of the first single-stranded nucleic acid molecule. Moreover, the first primer extension reaction can separate the second single-stranded nucleic acid molecule from the first single-stranded nucleic acid molecule. The first primer can be coupled to the separated second-single stranded molecule and a second primer extension reaction can be performed, using the first primer, to generate a third double-stranded nucleic acid molecule comprising the second single-stranded nucleic acid molecule and a fourth single-stranded nucleic acid molecule. In some cases, the first primer and/or the second primer cannot function may not be capable of functioning as an invader species. In some cases, the first primer can be directly attached to the support. In some cases, the first primer can be coupled to the support via a linker attached to the support.

In some cases, the third double-stranded nucleic acid molecule may be at least partially denatured by binding a second invader species free from the support to at least a portion of the second or fourth single-stranded nucleic acid molecule, which binding exposes a segment of the second single-stranded nucleic acid molecule that is complementary to a third primer. The third primer may be provided and coupled to the segment of the second single-stranded nucleic acid molecule. A third primer extension reaction may be performed, using the third primer, to generate a fourth double-stranded nucleic acid molecule comprising the second single-stranded nucleic acid molecule and a fifth single-stranded nucleic acid molecule that is complementary to at least a portion of the second single-stranded nucleic acid molecule. The third primer extension reaction can separate the fourth single-stranded nucleic acid molecule from the second single-stranded nucleic acid molecule. Furthermore, one or more steps of the method may be repeated to generate one or more additional double-stranded nucleic acid molecules coupled to the support. In some cases, the first double-stranded nucleic acid molecule and/or second primer may be provided in solution. Moreover, the denaturing of the first double-stranded nucleic acid molecule via the first invader species and/or the coupling of the second primer to the denatured first double-stranded nucleic acid molecule may also be completed in solution.

In some cases, the first and second primer may have the same nucleic acid sequence, or, in other cases, the first and second primer may have different nucleic acid sequences. In some cases, the second primer may be provided in solution (e.g., free from the support) or may be provided coupled to the support. In some cases, the first primer and the third primer may have the same nucleic acid sequence or, in other cases, the first primer and the third primer may have different nucleic acid sequences. In some cases, the first invader species and the second invader species may be the same invader species or, in other cases, the first invader species and the second invader species may be the same invader species. In some cases, the first invader species and/or the second invader species may be, for example, an oligonucleotide, a nucleic acid comprising a locked nucleic acid (LNA), a nucleic acid comprising a peptide nucleic acid (PNA), or a sequence-specific single-stranded nucleic acid binding protein. In some cases, at least one of the first invader species or the second invader species is an oligonucleotide that cannot be extended in a primer extension reaction. Moreover, the support may be, for example, a bead, an array pixel, a sensor, a particle, or an electrode.

Additionally, the first double-stranded nucleic acid molecule may be provided by subjecting a parent double-stranded nucleic acid molecule that is derived from the nucleic acid sample to one or more cycles of a nucleic acid amplification reaction. The first double-stranded nucleic acid molecule can be an amplicon of the parent double-stranded nucleic acid molecule generated during the one or more cycles of the nucleic acid amplification reaction. In some cases, the one or more cycles of the nucleic acid amplification reaction are completed with the aid of a second invader species. In some cases, the first invader species and the second invader species are the same invader species or, in other cases, the first invader species and the second invader species are different invader species. In some cases, at least one of the first invader species and the second invader species may be an oligonucleotide that cannot be extended in a primer extension reaction. In some cases, the nucleic acid amplification reaction may be completed in solution and, in some cases, may be completed with the use of a solution-phase primer.

Moreover, the first primer extension reaction can be completed with the aid of a strand-displacing polymerase. The strand-displacing polymerase may be, for example, Bsu polymerase I, Large Fragment (*Bacillus subtilits*), Bst polymerase, PolI polymerase, phi 29 polymerase, Large Fragment (*Bacillus stearothermophilus*), *Staphylococcus aureus* polymerase, Klenow Fragment (3'→5' exo-), a variant thereof, a modified product thereof, a homologue thereof, a derivative thereof, or a combination thereof.

In some cases, the first invader species can be an oligonucleotide that is bound to at least a portion of the first or second single-stranded nucleic acid molecule with the aid of a recombinase. The recombinase may be, for example, Cre recombinase, Hin recombinase, RecA recombinase, RAD51 recombinase, Tre recombinase, FLP recombinase, UvsX recombinase, DMC1 recombinase, a variant thereof, a modified product thereof, a homologue thereof, a derivative thereof, or a combination thereof. In some cases, the binding of the first invader species can be completed with the aid of energy transfer. Energy may be transferred from a form of chemical energy (e.g., provided by adenosine triphosphate (ATP)) and/or may be transferred from a form of thermal energy. In some cases, the nucleic acid sample may be amplified isothermally.

An additional aspect of the disclosure provides a method for amplifying a nucleic acid sample. A support comprising a first primer may be provided along with a second primer. The first primer can be coupled to a first single-stranded nucleic acid molecule that is derived from the nucleic acid sample. A first primer extension reaction, using the first primer, can be performed to generate a first double-stranded nucleic acid molecule comprising the first single-stranded nucleic acid molecule and a second single-stranded nucleic acid molecule that is complementary to at least a portion of the first single-stranded nucleic acid molecule. The first double-stranded nucleic acid molecule can be at least partially denatured by binding an invader species free from the support to at least a portion of the first or second single-stranded nucleic acid molecule, which binding exposes a segment of the first or second single-stranded nucleic acid molecule that is complementary to the second primer. The second primer can be coupled to the segment of the first or second single-stranded nucleic acid molecule and a second primer extension reaction can be performed, using the second primer, to generate a second double-stranded nucleic acid molecule. The second double-stranded nucleic acid molecule may comprise the first or second single-stranded nucleic acid molecule and a third single-stranded nucleic acid molecule that is complementary to at least a portion of the first or second single-stranded nucleic acid molecule. Moreover, the second primer extension reaction can separate the first single-stranded nucleic acid molecule from the second single-stranded nucleic acid molecule.

In some cases, the second primer may be provided free from the support or, in other cases, the second primer may be provided coupled to the support. In some cases, the first and second primers may have the same nucleic acid sequence or, in other cases, the first and second primers may have different nucleic acid sequences. In some cases, the first primer and the invader species may be different or may be the same. In some cases, the first primer may not be capable of functioning as an invader species. In some cases, the first primer can be directly attached to the support. In some cases, the first primer can be coupled to the support via a linker attached to the support.

In some cases, the binding of the invader species to the at least a portion of first or second single-stranded nucleic acid molecule can expose a segment of the first single-stranded nucleic acid molecule that is complementary to the second primer. In such cases, the second primer can be coupled to the segment of the first single-stranded nucleic acid molecule and the second primer extension reaction can be performed, using the second primer, to generate the second double-stranded nucleic acid molecule that comprises the first single-stranded nucleic acid molecule and the third single-stranded nucleic acid molecule that is complementary to at least a portion of the first single-stranded nucleic acid molecule. A third primer can be coupled to the separated second single-stranded nucleic acid molecule and a third primer extension reaction can be performed, using the third primer, to generate a third double-stranded nucleic acid molecule. The third double-stranded nucleic acid molecule may comprise the second single-stranded nucleic acid molecule and a fourth single-stranded nucleic acid molecule that is complementary to at least a portion of the second single-stranded nucleic acid molecule. In some cases, the third primer may be free from the support or, in other cases, the third primer may be coupled to the support. In some cases, the first and the third primer may have the same nucleic acid sequence or, in other cases, the first primer and the third primer may have different nucleic acid sequences.

In some cases, the binding of the invader species to the at least a portion of first or second single-stranded nucleic acid molecule can expose a segment of the second single-stranded nucleic acid molecule that is complementary to the second primer. In such cases, the second primer can be coupled to the segment of the second single-stranded nucleic acid molecule and the second primer extension reaction can be performed, using the second primer, to generate the second double-stranded nucleic acid molecule comprising the second single-stranded nucleic acid molecule and the third single-stranded nucleic acid molecule that is complementary to at least a portion of the second single-stranded nucleic acid molecule. A third primer can be coupled to the first single-stranded nucleic acid molecule and a third primer extension reaction can be performed, using the third primer, to generate a third double-stranded nucleic acid molecule comprising the first single-stranded nucleic acid molecule and a fourth single-stranded nucleic acid molecule that is complementary to at least a portion of the first single-stranded nucleic acid molecule. In some cases, the third primer may be free from the support or, in other cases, the third primer may be coupled to the support. In some cases, the first and the third primer may have the same nucleic acid sequence or, in other cases, the first primer and the third primer may have different nucleic acid sequences.

Furthermore, one or more steps of the method may be repeated for one or more cycles for each molecule of the double-stranded nucleic acid molecule that is generated in the previous cycle. In some cases, the invader species may be, for example, an oligonucleotide, a nucleic acid comprising a locked nucleic acid (LNA), a nucleic acid comprising a peptide nucleic acid (PNA), or a sequence-specific single-stranded nucleic acid binding protein. In some cases, the invader species may be an oligonucleotide that cannot be extended in a primer extension reaction.

In some cases, the support may be, for example, a bead, an array pixel, a sensor, a particle, or an electrode. In some cases, the first single-stranded nucleic acid molecule may be derived from a double-stranded nucleic acid molecule that is derived from the nucleic acid sample. In some cases, the first primer extension reaction may be completed with the aid of a strand-displacing polymerase. The strand-displacing polymerase may be, for example, Bsu polymerase I, Large Fragment (*Bacillus subtilits*), Bst polymerase, PolI polymerase, phi 29 polymerase, Large Fragment (*Bacillus stearothermophilus*), *Staphylococcus aureus* polymerase, Klenow Fragment (3'→5' exo-), a variant thereof, a modified product thereof, a homologue thereof, a derivative thereof, or a combination thereof.

In some cases, the invader species may be an oligonucleotide that is bound to at least a portion of the first or second single-stranded nucleic acid molecule with the aid of a recombinase. The recombinase may be, for example, Cre recombinase, Hin recombinase, RecA recombinase, RAD51 recombinase, Tre recombinase, FLP recombinase, UvsX recombinase, DMC1 recombinase, a variant thereof, a modified product thereof, a homologue thereof, a derivative thereof, or a combination thereof. In some cases, the binding of the invader species can be completed with the aid of energy transfer. Energy may be transferred from a form of chemical energy (e.g., provided by adenosine triphosphate (ATP)) and/or a form of thermal energy. In some cases, the nucleic acid sample is amplified isothermally.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." and "FIGS." herein), of which:

FIG. 5 is a schematic that illustrates an example primer coupling phase;

FIG. 7 is a schematic that illustrates an example primer coupling phase and method of nucleic acid amplification;

FIG. 10 (panel A) schematically depicts various components in a reaction mixture described in Example 1. FIG. 10 (panel B) depicts photographs of gels as described in Example 1.

FIG. 12 (panel B) depicts a photograph of a gel as described in Example 3.

DETAILED DESCRIPTION

Figure 1:
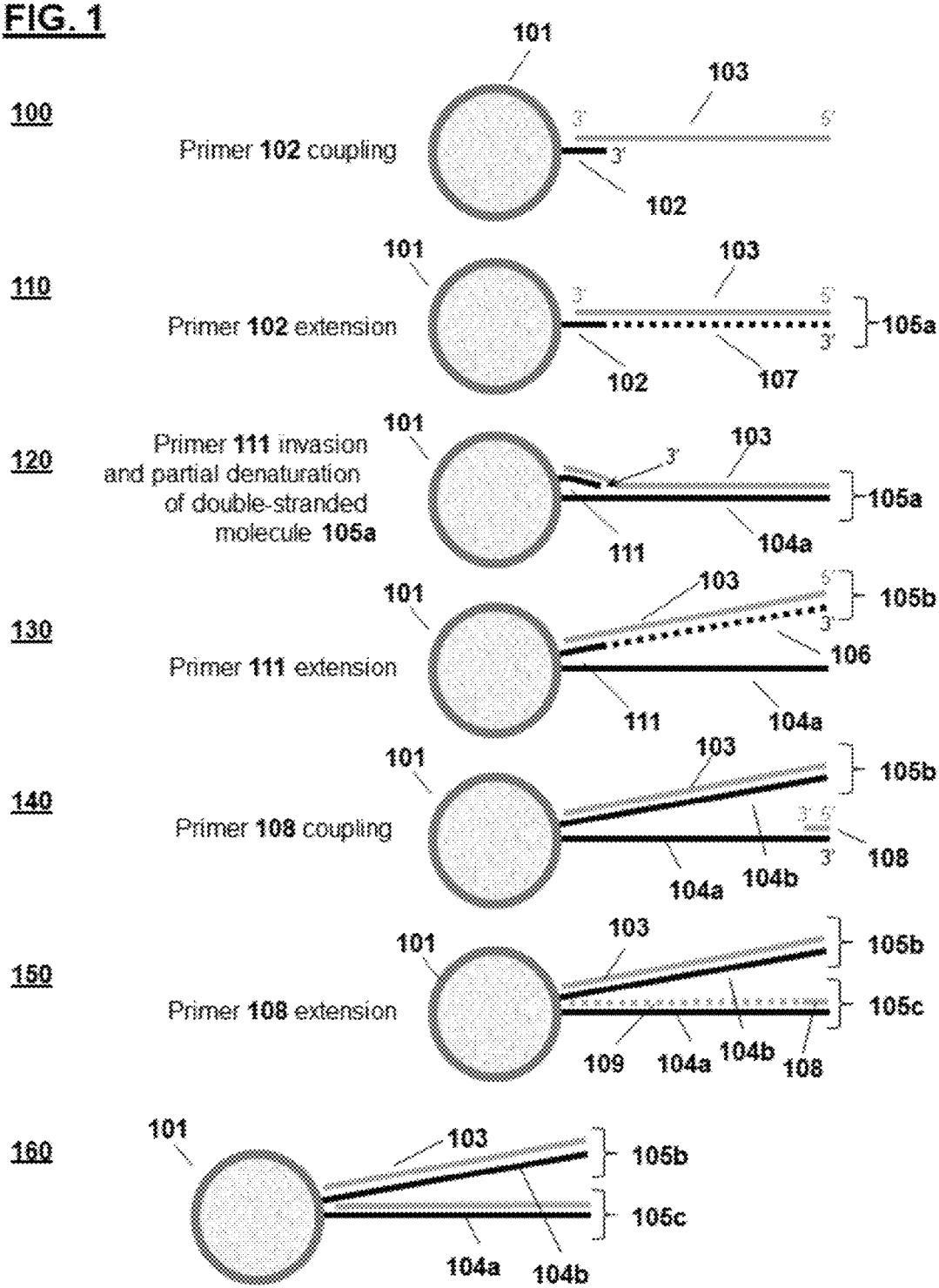
FIG. 1 is a schematic that illustrates an example method for nucleic acid amplification.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nucleotide," as used herein, generally refers to an organic molecule that serves as the monomer, or subunit, of a nucleic acid molecule, such as a deoxyribonucleic (DNA) molecule or ribonucleic acid (RNA) molecule. In some embodiments, a nucleotide may also be a peptide nucleic acid (PNA) nucleotide or a locked nucleic acid (LNA) nucleotide.

The term "primer," as used herein, generally refers to a strand of nucleic acid that serves as a starting point for nucleic acid synthesis, such as polymerase chain reaction (PCR). In an example, during replication of a DNA sample, an enzyme that catalyzes replication starts replication at the 3'-end of a primer attached to the DNA sample and copies the opposite strand.

The term "polymerase," as used herein, generally refers to an enzyme (e.g., cellular or viral enzyme) that synthesizes nucleic acid molecules (e.g., DNA) from their nucleotide building blocks. Examples of polymerases include DNA polymerases and RNA polymerases.

The present disclosure provides methods and systems for nucleic acid amplification. Such methods and systems for nucleic acid amplification may be used in a variety of applications including, for example, nucleic acid sequencing and the detection of biological species. In some cases, nucleic acid amplification and nucleic acid sequencing and/or the detection of a biological species may be performed by an integrated system. The integrated system may comprise, for example, an amplification module and a sequencing/detection module. Nucleic acid amplification can be performed in the amplification module and nucleic acid sequencing and/or the detection of a biological species can be performed in the sequencing/detection module. In other cases, an integrated system may comprise a single amplification and sequencing/detection module. Nucleic acid amplification, nucleic acid sequencing, and/or the detection of a biological species may be performed in the single module.

Moreover, an integrated system may be capable of sensing various biological species or biological and/or chemical reactions. For instance, the integrated system may sense nucleic acids, proteins, antigens and/or antibodies. In some cases, the integrated system can include one or more individual sensors. Where the integrated system comprises a plurality of individual sensors, the individual sensors of the plurality may be arranged in a sensor array. In some cases, an integrated system may be as described in PCT Patent Application No. PCT/US2011/054769, PCT Patent Application No. PCT/US2012/039880, PCT Patent Application No. PCT/US2012/067645, and U.S. patent application Ser. No. 13/481,858, each of which is entirely incorporated herein by reference.

Methods for Nucleic Acid Amplification

An aspect of the present disclosure provides methods for nucleic acid amplification. In some cases, methods for nucleic acid amplification described herein may be useful for confined amplification of nucleic acids. Amplification of a nucleic acid can be achieved in isolation from the amplification of other nucleic acids. Moreover, methods described herein can combine surface tethering of species useful in nucleic acid amplification reactions (e.g., primers, template nucleic acids/oligonucleotides, etc.), asymmetric amplification methods, and/or oligonucleotide invasion (including primer invasion), a concept described elsewhere herein. Furthermore, methods for amplification may be executed isothermally and/or in parallel for different nucleic acids.

In an aspect, the present disclosure provides a method for amplifying a nucleic acid sample, comprising providing a support comprising a first primer and a second primer, and coupling the first primer to a first single-stranded nucleic acid molecule that is derived from the nucleic acid sample. The first single-stranded nucleic acid molecule can be derived from the nucleic acid sample using an enzyme that separates complementary strands of the nucleic acid sample, for example. Next, a first primer extension reaction can be performed using the first primer to generate a first double-stranded nucleic acid molecule comprising the first single-stranded nucleic acid molecule and a second single-stranded nucleic acid molecule that is complementary to at least a portion of the first single-stranded nucleic acid molecule. The first double-stranded nucleic acid molecule can then be at least partially, substantially, or fully denatured by binding the second primer to at least a portion of the first or second single-stranded nucleic acid molecule. Next, a second primer extension reaction can be performed using the second primer to generate a second double-stranded nucleic acid molecule comprising the first single-stranded nucleic acid molecule and a third single-stranded nucleic acid molecule that is complementary to at least a portion of the first single-stranded nucleic acid molecule. The second primer extension reaction can separate the second single-stranded nucleic acid molecule from the first single-stranded nucleic acid molecule.

In another aspect, the present disclosure provides a method for amplifying a nucleic acid sample, comprising providing a support comprising a first primer and a second primer and coupling the first primer to a first single-stranded nucleic acid molecule that is derived from the nucleic acid sample. Next, a first primer extension reaction can be performed using the first primer to generate a first double-stranded nucleic acid molecule comprising the first single-stranded nucleic acid molecule and a second single-stranded nucleic acid molecule that is complementary to at least a portion of the first single-stranded nucleic acid molecule. The first double-stranded nucleic acid molecule can be at least partially, substantially, or fully denatured by binding an invader species to at least a portion of the first or second single-stranded nucleic acid molecule. In some examples, the invader species is a nucleic acid molecule. The invader species can be different from the first primer and/or the second primer. The binding can expose a segment of the first single-stranded nucleic acid molecule that is complementary to the second primer. Next, the second primer can be coupled to the segment of the first single-stranded nucleic acid molecule, and a second primer extension reaction can be performed using the second primer to generate a second double-stranded nucleic acid molecule comprising the first single-stranded nucleic acid molecule and a third single-stranded nucleic acid molecule that is complementary to at least a portion of the first single-stranded nucleic acid molecule. The second primer extension reaction can separate the second single-stranded nucleic acid molecule from the first single-stranded nucleic acid molecule.

In some embodiments, a method for nucleic acid amplification comprises coupling a third primer to the second single-stranded nucleic acid molecule and performing a third primer extension reaction using the third primer to generate a third double-stranded nucleic acid molecule comprising the second single-stranded nucleic acid molecule and a fourth single-stranded nucleic acid molecule that is complementary to at least a portion of the second single-stranded nucleic acid molecule.

An additional aspect of the disclosure provides a method for amplifying a nucleic acid sample. A support comprising a first primer and a first double-stranded nucleic acid molecule derived from the nucleic acid sample may be provided, where the first double-stranded nucleic acid molecule comprises a first single-stranded nucleic acid molecule and a second single-stranded nucleic acid molecule that is at least partially complementary to said first single-stranded nucleic acid molecule. The first double-stranded nucleic acid molecule may be at least partially denatured by binding a first invader species free from the support to at least a portion of the first or second single-stranded nucleic acid molecule, where the binding of the first invader species exposes a segment of the first single-stranded nucleic acid molecule that is complementary to the first primer. The first primer can be coupled to the segment of the first single-stranded nucleic acid molecule and first primer extension reaction can be performed using the first primer. The first primer extension reaction can generate a second double-stranded nucleic acid molecule comprising the first single-stranded nucleic acid molecule and a third single-stranded nucleic acid molecule that is complementary to at least a portion of the first single-stranded nucleic acid molecule and can separate the second single-stranded nucleic acid molecule from the first single-stranded nucleic acid molecule. In some embodiments, the binding of the first invader species, the denaturing of the first double-stranded nucleic acid molecule, and the first primer extension reaction via the first primer occur in solution. In some embodiments, the first double-stranded nucleic acid molecule is provided by subjecting a parent double-stranded nucleic acid molecule that is derived from the nucleic acid sample to one or more cycles of a nucleic acid amplification reaction, such that the first double-stranded nucleic acid molecule is an amplicon of the parent double-stranded nucleic acid molecule generated during the one or more cycles of the nucleic acid amplification reaction.

In some embodiments, the second double-stranded nucleic acid molecule can be at least partially denatured by binding a second invader species free from the support to at least a portion of the first or third single-stranded nucleic acid molecule, where the binding of the second invader species exposes a segment of the first single-stranded nucleic acid molecule that is complementary to a second primer. In some embodiments, the second primer can be provided and coupled to the segment of the first single-stranded nucleic acid molecule. A second primer extension reaction can be performed using the second primer that generates a second double-stranded nucleic acid molecule comprising the first single-stranded nucleic acid molecule and a fourth single-stranded nucleic acid molecule that is complementary to at least a portion of the first single-stranded nucleic acid molecule. The second primer extension reaction can also separate the third single-stranded nucleic acid molecule from the first single-stranded nucleic acid molecule. In some embodiments, one or more steps of the method may be repeated to generate additional double-stranded nucleic acid molecules coupled to the support.

An additional aspect of the disclosure provides a method for amplifying a nucleic acid sample. A support comprising a first primer and a second primer may be separately provided along with a first double-stranded nucleic acid molecule comprising a first single-stranded nucleic acid molecule and a second single-stranded nucleic acid molecule that is at least partially complementary to said first single-stranded nucleic acid molecule. The double-stranded nucleic acid molecule may be derived from the nucleic acid sample the second-single-stranded nucleic acid molecule comprises a sequence a least partially complementary to the first primer. The first double-stranded nucleic acid molecule can be at least partially denatured by binding a first invader species free from said support to at least a portion of the first or second single-stranded nucleic acid molecule, where the binding of the first invader species exposes a segment of the first single-stranded nucleic acid molecule that is complementary to the second primer. The second primer can be coupled to the segment of the first single-stranded nucleic acid molecule a first primer extension reaction can be performed using the second primer that generates a second double-stranded nucleic acid molecule comprising the first single-stranded nucleic acid molecule and a third single-stranded nucleic acid molecule that is complementary to at least a portion of the first single-stranded nucleic acid molecule. Additionally, the first primer extension reaction can separate the second single-stranded nucleic acid molecule from the first single-stranded nucleic acid molecule. The first primer can be coupled to the separated second-single stranded molecule and a second primer extension reaction can be performed using the first primer that generates a third double-stranded nucleic acid molecule comprising the second single-stranded nucleic acid molecule and a fourth single-stranded nucleic acid molecule. In some embodiments, the binding of the first invader species, the denaturing of the first double-stranded nucleic acid molecule, and the first primer extension reaction via the second primer occur in solution. In some embodiments, the first double-stranded nucleic acid molecule is provided by subjecting a parent double-stranded nucleic acid molecule that is derived from the nucleic acid sample to one or more cycles of a nucleic acid amplification reaction, such that the first double-stranded nucleic acid molecule is an amplicon of the parent double-stranded nucleic acid molecule generated during the one or more cycles of the nucleic acid amplification reaction.

In some embodiments, the third double-stranded nucleic acid molecule may be at least partially denatured by binding a second invader species free from the support to at least a portion of the second or fourth single-stranded nucleic acid molecule, where the binding of the second invader species exposes a segment of the second single-stranded nucleic acid molecule that is complementary to a third primer. In some embodiments, the third primer can be provided and coupled to the segment of the second single-stranded nucleic acid molecule and performing a second primer extension reaction using the third primer to generate a fourth double-stranded nucleic acid molecule comprising the second single-stranded nucleic acid molecule and a fifth single-stranded nucleic acid molecule that is complementary to at least a portion of the second single-stranded nucleic acid molecule, wherein the second primer extension reaction separates the fourth single-stranded nucleic acid molecule from the second single-stranded nucleic acid molecule. In some embodiments, one or more steps of the method may be repeated to generate additional double-stranded nucleic acid molecules coupled to the support.

An additional aspect of the disclosure provides a method for amplifying a nucleic acid sample. A support comprising a first primer may be provided in addition to a second primer. The first primer can be coupled to a first single-stranded nucleic acid molecule that is derived from the nucleic acid sample. A first primer extension reaction can be performed using the first primer to generate a first double-stranded nucleic acid molecule comprising the first single-stranded nucleic acid molecule and a second single-stranded nucleic acid molecule that is complementary to at least a portion of the first single-stranded nucleic acid molecule. The first double-stranded nucleic acid molecule can be at least partially denatured by binding an invader species free from said support to at least a portion of the first or second single-stranded nucleic acid molecule, where the binding of the invader species exposes a segment of the first or second single-stranded nucleic acid molecule that is complementary to the second primer. The second primer can be coupled to the segment of the first or second single-stranded nucleic acid molecule and a second primer extension reaction can be performed using the second primer to generate a second double-stranded nucleic acid molecule comprising the first or second single-stranded nucleic acid molecule and a third single-stranded nucleic acid molecule that is complementary to at least a portion of the first or second single-stranded nucleic acid molecule. Additionally, the second primer extension reaction can separate the first single-stranded nucleic acid molecule from the second single-stranded nucleic acid molecule. In some embodiments, the second primer may be free from the support. In some embodiments, the second primer may be coupled to the support.

In some embodiments, the binding of the invader species to the at least a portion of the first or second single-stranded nucleic acid molecule may expose a segment of the first single-stranded nucleic acid molecule that is complementary to the second primer. In some embodiments, the second primer can be coupled to the segment of the first single-stranded nucleic acid molecule and the second primer extension reaction can be performed such that the second double-stranded nucleic acid molecule comprises the first single-stranded nucleic acid molecule and the third single-stranded nucleic acid molecule, where the third single-stranded nucleic acid molecule is complementary to at least a portion of the first single-stranded nucleic acid molecule. In addition, the second primer extension reaction can separate the second single-stranded nucleic acid molecule from the first single-stranded nucleic acid molecule. In some embodiments, a third primer may be coupled to the separated second single-stranded nucleic acid molecule and a third primer extension reaction can be performed to generate a third double-stranded nucleic acid molecule that comprises the second single-stranded nucleic acid molecule and a fourth single-stranded nucleic acid molecule that is complementary to at least a portion of the second single-stranded nucleic acid molecule. In some embodiments, the third primer may be free from the support. In some embodiments, the third primer may be coupled to the support.

In some embodiments, the binding of the invader species to the at least a portion of the first or second single-stranded nucleic acid molecule may expose a segment of the second single-stranded nucleic acid molecule that is complementary to the second primer. In some embodiments, the second primer can be coupled to the segment of the second single-stranded nucleic acid molecule and the second primer extension reaction can be performed such that the second double-stranded nucleic acid molecule comprises the second single-stranded nucleic acid molecule and the third single-stranded nucleic acid molecule, where the third single-stranded nucleic acid molecule is complementary to at least a portion of the second single-stranded nucleic acid molecule. In addition, the second primer extension reaction can separate the first single-stranded nucleic acid molecule from the second single-stranded nucleic acid molecule. In some embodiments, a third primer may be coupled to the separated first single-stranded nucleic acid molecule and a third primer extension reaction can be performed to generate a third double-stranded nucleic acid molecule that comprises the first single-stranded nucleic acid molecule and a fourth single-stranded nucleic acid molecule that is complementary to at least a portion of the first single-stranded nucleic acid molecule. In some embodiments, the third primer may be free from the support. In some embodiments, the third primer may be coupled to the support.

An example method for amplifying a nucleic acid sample is schematically depicted in FIG. 1. As shown in FIG. 1, a support (e.g., a bead) 101 comprises a first primer 102 that is immobilized to the surface of the support 101. First primer 102 can couple (e.g., prime, anneal to) a single-stranded template nucleic acid (e.g., a template oligonucleotide) molecule 103 that is derived from the nucleic acid sample in a primer coupling phase 100. In some cases, the single-stranded template nucleic acid molecule 103 is derived from a double-stranded nucleic acid molecule that is derived from the nucleic acid sample.

Following coupling of the single-stranded template nucleic acid molecule 103 to the first primer 102, the first primer 102 can be extended 107 in a primer extension reaction (e.g., via the action of a polymerase (e.g., a strand-displacing polymerase)) 110, to generate a first molecule 105a of a double-stranded nucleic acid that comprises the single-stranded template nucleic acid molecule 103 and a single-stranded complementary nucleic acid molecule 104a.

A second primer 111 also immobilized to support 101, which can be the same sequence as the first primer 102 or may be a different sequence from the first primer 102 (second primer 111 is of the same sequence as first primer 102 in FIG. 1), may be capable of strand invasion. In a strand invasion phase 120, the second primer 111 can at least partially denature the double-stranded nucleic acid molecule 105a by binding to its complementary sequence on single-stranded template nucleic acid molecule 103. Strand-invasion of the double-stranded nucleic acid molecule 105a may be achieved, for example, using chemical energy. For example, the binding of a recombinase enzyme (e.g., a recombinase capable of utilizing a chemical energy source for function, such as, for example, adenosine triphosphate (ATP)) to the second primer 111 may permit sequence specific coupling of the second primer 111 to its complementary sequence on single-stranded template nucleic acid molecule 103.

Upon coupling of single-stranded template nucleic acid molecule 103 to the second primer 111, second primer 111 can be extended 106 in a second primer extension reaction 130 (e.g., via the action of a polymerase (e.g., a strand-displacing polymerase)) to generate a second molecule 105b of the double-stranded nucleic acid. The second molecule 105b of the double-stranded nucleic acid comprises the single-stranded template nucleic acid molecule 103 and a second single-stranded complementary nucleic acid molecule 104b. During the second primer extension reaction 130, the action of a polymerase (e.g., a strand-displacing polymerase) displaces the single-stranded complementary nucleic acid molecule 104a from single-stranded template nucleic acid molecule 103, such that single-stranded complementary nucleic acid molecule 104a is no longer a component of a double-stranded nucleic acid molecule.

The single-stranded complementary nucleic acid molecule 104a can be coupled with (e.g., annealed to) a third primer 108 (e.g., the third primer 108 may be in solution and not immobilized to the support 101, as shown in FIG. 1) that may or may not be capable of strand-invasion in a second primer coupling phase 140. The third primer 108 can be extended 109 in a third primer extension reaction 150 (e.g., via the action of a polymerase (e.g., a strand-displacing polymerase)) to generate a third molecule 105c of the double-stranded nucleic acid. After one cycle of amplification, the product 160 comprises support 101 coupled to two molecules 105b and 105c of the double-stranded nucleic acid.

One or more of phases 120, 130, 140, and 150 can repeat over a desired or otherwise predetermined number of cycles, such as at least 1, 2, 3, 4, 5, 6, 7, 8, 9, 10, 20, 30, 40, 50, 60, 70, 80, 90, 100, 200, 300, 400, or 500 cycles. Each double-stranded nucleic acid molecule generated in a previous cycle can be subject to phases 120, 130, 140, and 150, resulting in exponential amplification. Additional molecules of the second primer 111 that are immobilized to the support 101 and additional molecules of the third primer 108 (e.g., third primer 108 in solution) can permit repeated cycling. Amplification can proceed for as long as additional molecules of the second primer 111 and the third primer 108 are available for primer coupling and subsequent extension. In some cases, the third primer 108 may be present in an amount greater than the second primer 111 or the second primer 111 may be present in an amount greater than the third primer 108, resulting in asymmetric amplification.

In some cases, the first primer 102 may have the same nucleic acid sequence of any of the second primer 111 and the third primer 108. In some cases, the second primer 111 may have the same nucleic acid sequence of any of the first primer 102 and the third primer 412. In some cases, the third primer 108 may have the same nucleic acid sequence of any of the first primer 102 and the second primer 111. In some cases, the first primer 102 may have a different nucleic acid sequence from any of the second primer 111 and the third primer 108. In some cases, the second primer 111 may have a different nucleic acid sequence from any of the first primer 102 and the third primer 108. In some cases, the third primer 108 may have a different nucleic acid sequence from any of the first primer 102 and the second primer 111.

Moreover, in some cases, amplification, as shown in FIG. 1, may be completed isothermally at an appropriate temperature, including an amplification temperature described elsewhere herein. In some examples, a given temperature is selected for amplification and maintained constant or substantially constant during isothermal amplification. Where the support is initially associated with only one single-stranded template nucleic acid molecule 103, clonal amplification of the single-stranded template nucleic acid molecule 103 can be achieved. As shown, nucleic acid is not released from the support 101 during each phase of amplification, resulting in confinement of the amplification reaction to the support 101.

Figure 2:
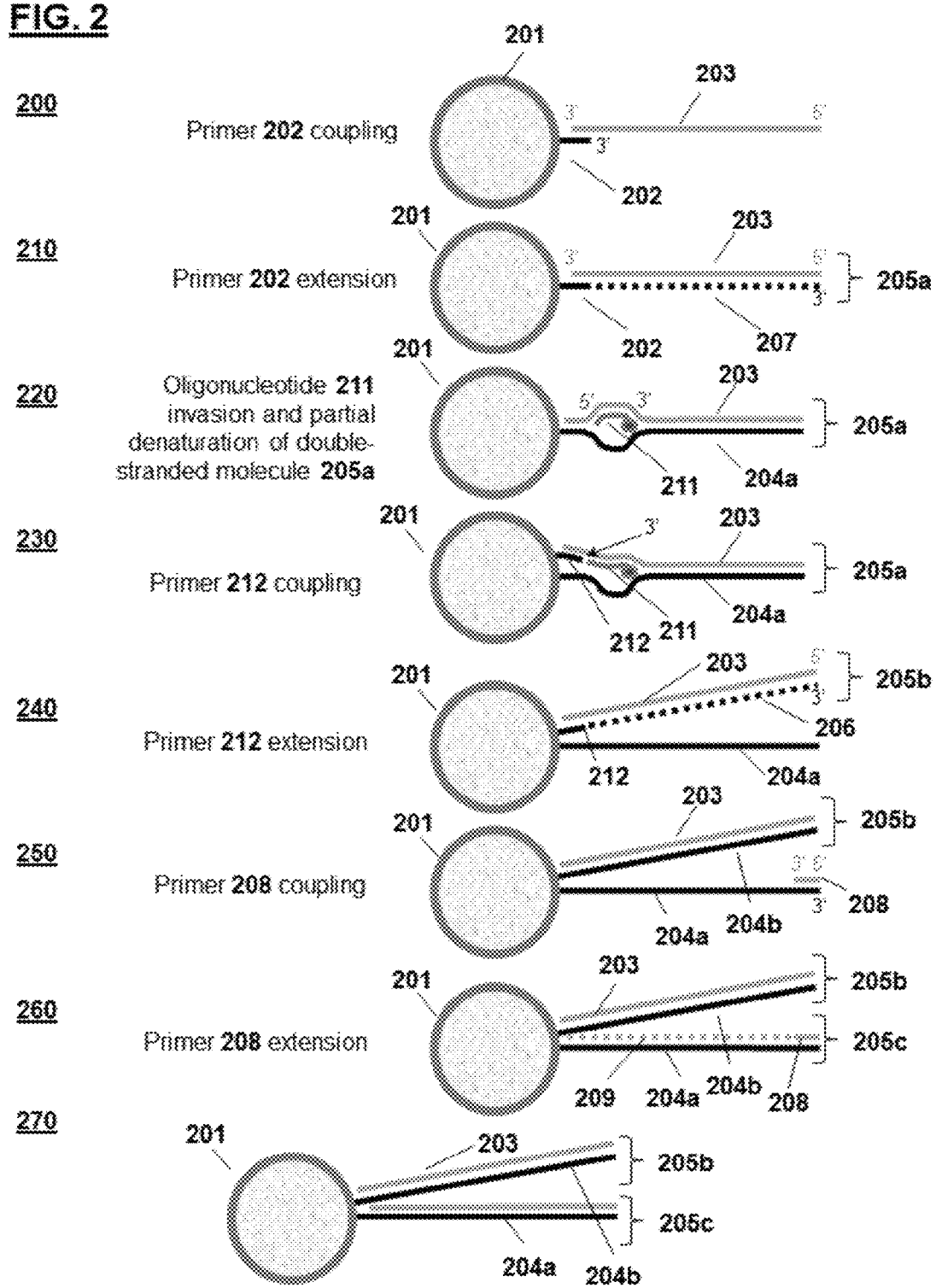
FIG. 2 is a schematic that illustrates an example method for nucleic acid amplification.

An additional example method for amplifying a nucleic acid sample is schematically depicted in FIG. 2. As shown in FIG. 2, a support (e.g., a bead) 201 comprises a first primer 202 that is immobilized to the surface of the support 201. The first primer 202 can couple to (e.g., anneal to, prime) a single-stranded template nucleic acid (e.g., a template oligonucleotide) molecule 203 that is derived from the nucleic acid sample in a primer coupling phase 200. In some cases, the single-stranded template nucleic acid molecule 203 is derived from a double-stranded nucleic acid molecule that is derived from the nucleic acid sample.

Following coupling of the single-stranded template nucleic acid molecule 203 to the first primer 202, the first primer 202 can be extended 207 in a primer extension reaction (e.g., via the action of a polymerase (e.g., a strand-displacing polymerase)) 210, to generate a first molecule 205a of a double-stranded nucleic acid, that comprises the single-stranded template nucleic acid molecule 203 and a single-stranded complementary nucleic acid molecule 204a.

An invader species (e.g., invader oligonucleotide 211) may be capable of strand invasion and may be provided free from the support 201 (e.g., in solution). In a strand invasion phase 220, the invader oligonucleotide 211 can at least partially denature the double-stranded nucleic acid molecule 205a by binding to its complementary sequence on single-stranded template nucleic acid molecule 203. In some cases, the invader oligonucleotide may bind a complementary sequence on the single-stranded complementary nucleic acid molecule 204a instead. Strand-invasion of the double-stranded nucleic acid molecule 205a may be achieved, for example, using chemical energy. For example, the binding of a recombinase enzyme (e.g., a recombinase capable of utilizing a chemical energy source for function, such as, for example, adenosine triphosphate (ATP)) to the invader oligonucleotide 211 may permit sequence specific coupling of the invader oligonucleotide 211 to its complementary sequence on single-stranded template nucleic acid molecule 203. The binding of invader oligonucleotide 211 to single-stranded template nucleic acid molecule 203 can expose a segment of the single-stranded template nucleic acid molecule 203 that is complementary to a second primer 212. In some cases, the invader oligonucleotide is of the same sequence as the second primer 212 or is of a different sequence from the second primer 212. In some cases, the second primer 212 may be free from the support 201 or may be immobilized to the support 201.

The second primer 212 can couple (e.g., anneal to) with its complementary, exposed segment of single-stranded template nucleic acid molecule 203 in a second primer coupling phase 230. Upon coupling of single-stranded template nucleic acid molecule 203 with the second primer 212, the second primer 212 can be extended 206 in a second primer extension reaction 240 (e.g., via the action of a polymerase (e.g., a strand-displacing polymerase)) to generate a second molecule 205b of the double-stranded nucleic acid. The second molecule 205b of the double-stranded nucleic acid comprises the single-stranded template nucleic acid molecule 203 and a second single-stranded complementary nucleic acid molecule 204b. During the second primer extension reaction 240, the action of a polymerase (e.g., a strand-displacing polymerase) displaces the single-stranded complementary nucleic acid molecule 204a from single-stranded template nucleic acid molecule 203, such that single-stranded complementary nucleic acid molecule 204a is no longer a component of a double-stranded nucleic acid molecule. Moreover, at the conclusion of extension 206, invader oligonucleotide 211 can also be displaced from single-stranded template nucleic acid molecule 203 and, in some cases, recycled in a subsequent amplification cycle. Furthermore, invader oligonucleotide 211 may be configured such that invader oligonucleotide 211 cannot be extended in a primer extension reaction. For example, invader oligonucleotide 211 may comprise a dideoxynucleotide (ddNTP) such that the presence of the ddNTP blocks extension of the invader oligonucleotide 211.

Additionally, the single-stranded complementary nucleic acid molecule 204a can be coupled with (e.g., annealed to) a third primer 208 (e.g., the third primer 208 may be in solution and not immobilized to the support 201, as shown in FIG. 2 or in some cases may also be immobilized to the support 201) that is not capable of strand-invasion in a third primer coupling phase 250. The third primer 208 can be extended 209 in a third primer extension reaction 260 (e.g., via the action of a polymerase (e.g., a strand-displacing polymerase)) to generate a third molecule 205c of the double-stranded nucleic acid. After one cycle of amplification, the product 270 comprises support 201 coupled to two molecules 205b and 205c of the double-stranded nucleic acid.

One or more of phases 220, 230, 240, 250, and 260 can repeat over a desired or otherwise predetermined number of cycles, such as at least 1, 2, 3, 4, 5, 6, 7, 8, 9, 10, 20, 30, 40, 50, 60, 70, 80, 90, 100, 200, 300, 400, or 500 cycles. Each double-stranded nucleic acid molecule generated in a previous cycle can be subject to phases 220, 230, 240, 250, and 260, resulting in exponential amplification. Additional molecules of the second primer 212 that are immobilized to the support 201, recycled or additional molecules of invader oligonucleotide 211, and additional molecules of the third primer 208 (e.g., third primer 208 in solution) can permit repeated cycling. Amplification can proceed for as long as additional molecules of the second primer 212, the third primer 208, and the invader oligonucleotide 211 are available, in addition to any other species (e.g., dNTPs, ATP, polymerase(s), cofactors, etc.) that may be useful for the amplification reaction. In some cases, the third primer 208 may be present in an amount greater than the second primer 212 or the second primer 212 may be present in an amount greater than the third primer 208, resulting in asymmetric amplification. In some cases, the first primer 202 may have the same nucleic acid sequence of either or both of the second primer 212 and the third primer 208. In some cases, the second primer 212 may have the same nucleic acid sequence of either or both of the first primer 202 and the third primer 208. In some cases, the third primer 208 may have the same sequence as either or both of the first primer 202 or the second primer 212. In some cases, the first primer 202 may have a different nucleic acid sequence from either or both of the second primer 212 and the third primer 208. In some cases, the second primer 212 may have a different nucleic acid sequence from either or both of the first primer 202 and the third primer 208. In some cases, the third primer 208 may have a different nucleic acid sequence from either or both of the first primer 202 or the second primer 212.

Moreover, in some cases, amplification, as shown in FIG. 2, may be completed isothermally at an appropriate temperature, including an amplification temperature described elsewhere herein. Where the support is initially associated with only one single-stranded template nucleic acid molecule 203, clonal amplification of the single-stranded template nucleic acid molecule 203 can be achieved. As shown, nucleic acid is not released from the support 201 during each phase of amplification, resulting in confinement of the amplification reaction to the support 201.

Figure 3:
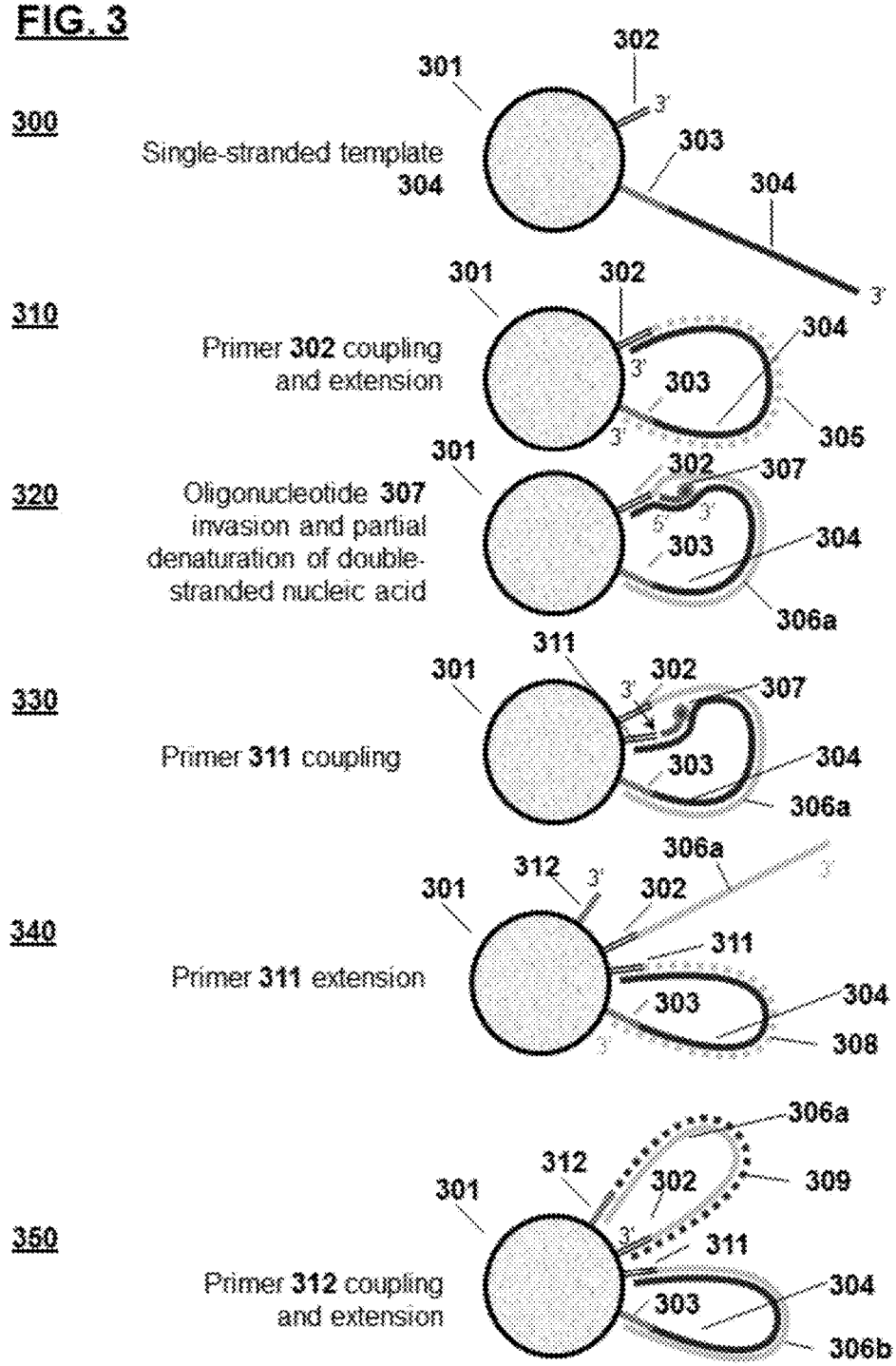
FIG. 3 is a schematic that illustrates an example method for nucleic acid amplification.

An additional example method for amplifying a nucleic acid sample is schematically depicted in FIG. 3. As shown in FIG. 3, a support (e.g., a bead) 301 comprises a first primer 302 and a second primer 303 that are both immobilized to the surface of the support 301. The second primer 303 is coupled to one end of a single-stranded template nucleic acid molecule 304 that is derived from the nucleic acid sample and also comprises a sequence complementary to the first primer 302 at its opposite end. The single-stranded template nucleic acid molecule 304 can be attached to the second primer 303 non-covalently (e.g., as hybridization (e.g., annealing) or covalently (e.g., ligation, via a primer extension reaction). In some cases, the single-stranded template nucleic acid molecule 304 is derived from a double-stranded nucleic acid molecule that is derived from the nucleic acid sample.

Via its sequence complementary to the first primer 302, single-stranded template nucleic acid molecule 304 can be coupled (e.g., annealed to) with the first primer 302 and extended 305 (e.g., via the action of a polymerase (e.g., a strand-displacing polymerase) in a primer extension reaction) in a primer coupling and extension phase 310. Following extension 305 of the first primer 302, a molecule of a double-stranded nucleic acid is generated that comprises the single-stranded template nucleic acid molecule 304 and a single-stranded complementary nucleic acid molecule 306a. As shown in FIG. 3, the double-stranded nucleic acid molecule is generated in a loop (e.g., bridge) configuration, with the first primer 302 and the second primer 303 as anchor points.

An invader species (e.g., invader oligonucleotide 307) may be capable of strand invasion and may be provided free from the support 301 (e.g., in solution). In a strand invasion phase 320, the invader oligonucleotide 307 can at least partially denature the double-stranded nucleic acid molecule by binding to its complementary sequence on single-stranded template nucleic acid molecule 304. In some cases, invader oligonucleotide may bind to a complementary sequence on single-stranded complementary strand 306a instead. Strand-invasion of the double-stranded nucleic acid molecule may be achieved, for example, using chemical energy. For example, the binding of a recombinase enzyme (e.g., a recombinase capable of utilizing a chemical energy source for function, such as, for example, adenosine triphosphate (ATP)) to the invader oligonucleotide 307 may permit sequence specific coupling of the invader oligonucleotide 307 to its complementary sequence on single-stranded template nucleic acid molecule 304. The binding of invader oligonucleotide 307 to single-stranded template nucleic acid molecule 304 can expose a segment of the single-stranded template nucleic acid molecule 304 that is complementary to a third primer 311. In some cases, the invader oligonucleotide 307 is of a different sequence from the third primer 311. In some cases, the invader oligonucleotide 307 may be the third primer 311. In some cases, the first primer 302 and the third primer 311 have the same sequence. In some cases, the first primer 302 and the third primer 311 may have different sequences.

The third primer 311 can couple (e.g., anneal to) with its complementary, exposed segment of single-stranded template nucleic acid molecule 304. Upon coupling of single-stranded template nucleic acid molecule 304 with the third primer 311, the third primer 311 can be extended 308 in a second primer extension reaction 340 (e.g., via the action of a polymerase (e.g., a strand-displacing polymerase)) to generate a second molecule of the double-stranded nucleic acid. The second molecule of the double-stranded nucleic acid comprises the single-stranded template nucleic acid molecule 304 and a second single-stranded complementary nucleic acid molecule 306b. During the second primer extension reaction 340, the action of a polymerase (e.g., a strand-displacing polymerase) displaces the single-stranded complementary nucleic acid molecule 306a from single-stranded template nucleic acid molecule 304, such that single-stranded complementary nucleic acid molecule 306a is no longer a component of a double-stranded nucleic acid molecule. Moreover, at the conclusion of extension 308, invader oligonucleotide 307 can also be displaced from single-stranded template nucleic acid molecule 304 and, in some cases, recycled in a subsequent amplification cycle. Furthermore, invader oligonucleotide 307 may be configured such that invader oligonucleotide cannot be extended in a primer extension reaction. For example, invader oligonucleotide 307 may comprise a dideoxynucleotide (ddNTP) such that the presence of the ddNTP blocks extension of the invader oligonucleotide 307.

The single-stranded complementary nucleic acid molecule 306a can be coupled with (e.g., annealed to) a fourth primer 312 that is also immobilized to the support 303 in a second primer coupling and extension phase 350. The fourth primer 312 can have the same sequence or a different sequence from the second primer 303 and may or may not be capable of strand-invasion in the primer coupling and extension phase 350. The fourth primer 312 can be extended 309 in a third primer extension reaction (e.g., via the action of a polymerase (e.g., a strand-displacing polymerase)) to generate a third molecule of the double-stranded nucleic acid. After one cycle of amplification, the support 301 is coupled to the second and third molecules of the double-stranded, each oriented in a loop (e.g., bridge) configuration.

One or more of phases 320, 330, 340, and 350 can repeat over a desired or otherwise predetermined number of cycles, such as at least 1, 2, 3, 4, 5, 6, 7, 8, 9, 10, 20, 30, 40, 50, 60, 70, 80, 90, 100, 200, 300, 400, or 500 cycles. Each double-stranded nucleic acid molecule generated in a previous cycle can be subject to phases 320, 330, 340, and 350, resulting in exponential amplification. Additional molecules of the third primer 311 that are immobilized to the support 301, recycled or additional molecules of invader oligonucleotide 307, and additional molecules of the fourth primer 312 that are immobilized to the support 301 can permit repeated cycling. Amplification can proceed for as long as additional molecules of the third primer 311, the fourth primer 312, the invader oligonucleotide 307 are available, in addition to any other species (e.g., dNTPs, ATP, polymerase(s), cofactors, etc.) that may be useful for the amplification reaction. In some cases, the fourth primer 312 may be present in an amount greater than the third primer 311 or the third primer 311 may be present in an amount greater than the third primer 311, resulting in asymmetric amplification.

In some cases, the first primer 302 may have the same nucleic acid sequence of any of the second primer 303, the third primer 311, and the fourth primer 312. In some cases, the second primer 312 may have the same nucleic acid sequence of any of the first primer 302, the third primer 311, and the fourth primer 312. In some cases, the third primer 311 may have the same nucleic acid sequence of any of the first primer 302, second primer 303, and the fourth primer 312. In some cases, the fourth primer 312 may have the same nucleic acid sequence of any of the first primer 302, second primer 303, and the third primer 311. In some cases, the first primer 302 may have a different nucleic acid sequence from any of the second primer 303, the third primer 311, and the fourth primer 312. In some cases, the second primer 303 may have a different nucleic acid sequence from any of the first primer 302, the third primer 311, and the fourth primer 312. In some cases, the third primer 311 may have a different nucleic acid sequence from any of the first primer 302, the second primer 303, and the fourth primer 312. In some cases, the fourth primer 312 may have a different nucleic acid sequence from any of the first primer 302, the second primer 303, and the third primer 311.

Moreover, in some cases, amplification, as shown in FIG. 3, may be completed isothermally at an appropriate temperature, including an amplification temperature described elsewhere herein. Where the support is initially associated with only one single-stranded template nucleic acid molecule 304, clonal amplification of the single-stranded template nucleic acid molecule 304 can be achieved. As shown, nucleic acid is not released from the support 301 during each phase of amplification, resulting in confinement of the amplification reaction to the support 301.

Additionally, in some embodiments, a method may comprise binding the invader species to at least a portion of the first single-stranded nucleic acid molecule and binding another invader species to at least a portion of the second single-stranded nucleic acid molecule. The binding of the other invader species can expose a segment of the second single-stranded nucleic acid that is complementary to the third primer. The coupling of the third primer to the second single-stranded nucleic acid molecule can comprise coupling the third primer to the segment of the second single-stranded nucleic acid.

Figure 4:
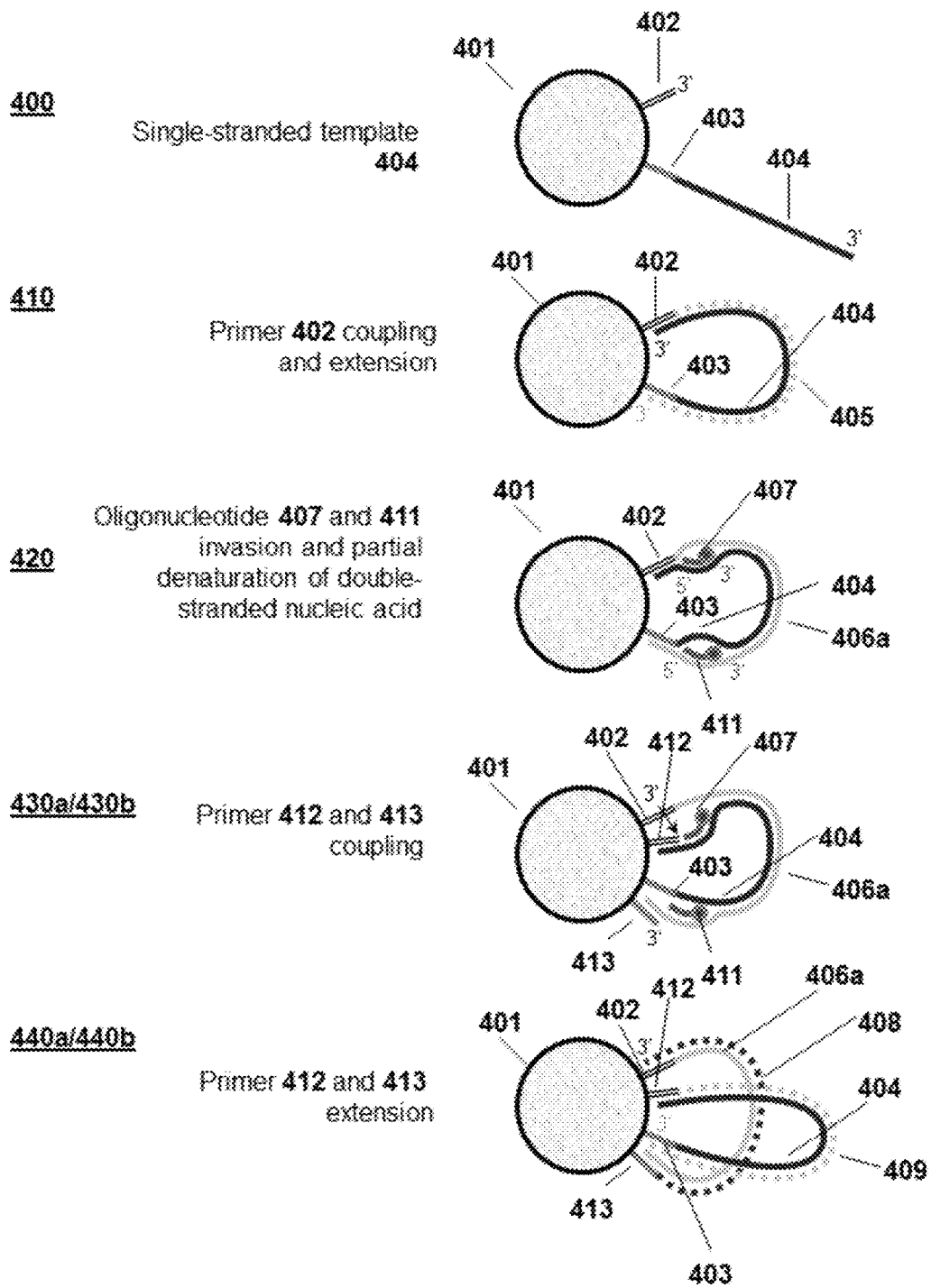
FIG. 4 is a schematic that illustrates an example method for nucleic acid amplification.

An additional example method for amplifying a nucleic acid sample is schematically depicted in FIG. 4. As shown in FIG. 4, a support (e.g., a bead) 401 comprises a first primer 402 and a second primer 403 that are both immobilized to the surface of the support 401. The second primer 403 is coupled to one end of a single-stranded template nucleic acid molecule 404 that is derived from the nucleic acid sample and also comprises a sequence complementary to the first primer 402 at its opposite end. The single-stranded template nucleic acid molecule 404 can be attached to the second primer 403 non-covalently (e.g., as hybridization (e.g., annealing) or covalently (e.g., ligation, via a primer extension reaction). In some cases, the single-stranded template nucleic acid molecule 404 is derived from a double-stranded nucleic acid molecule that is derived from the nucleic acid sample.

Via its sequence complementary to the first primer 402, single-stranded template nucleic acid molecule 404 can be coupled (e.g., annealed to) to the first primer 402 and extended 405 (e.g., via the action of a polymerase (e.g., a strand-displacing polymerase) in a primer extension reaction) in a primer coupling and extension phase 410. Following extension 405 of the first primer 402, a molecule of a double-stranded nucleic acid is generated that comprises the single-stranded template nucleic acid molecule 404 and a single-stranded complementary nucleic acid molecule 406a. As shown in FIG. 4, the double-stranded nucleic acid molecule is generated in a loop (e.g., bridge) configuration, with the first primer 402 and the second primer 403 as anchor points.

A plurality of invader species (e.g., invader oligonucleotides 407 and 411 which may or may not be the same invader oligonucleotides) may be capable of strand invasion and may be provided free from the support 401 (e.g., in solution). In a strand invasion phase 420, invader oligonucleotide 407 can at least partially denature the double-stranded nucleic acid molecule by binding to its complementary sequence on single-stranded template nucleic acid molecule 404 and invader oligonucleotide 411 can at least partially denature the double-stranded nucleic acid molecule by binding to its complementary sequence on single-stranded complementary nucleic acid 406a. Strand-invasion of the double-stranded nucleic acid molecule may be achieved, for example, using chemical energy. For example, the binding of a recombinase enzyme (e.g., a recombinase capable of utilizing a chemical energy source for function, such as, for example, adenosine triphosphate (ATP)) to invader oligonucleotide 407 may permit sequence specific coupling of the invader oligonucleotide 407 to its complementary sequence on single-stranded template nucleic acid molecule 404. Similarly, the binding of a recombinase enzyme (which may or may not be the same recombinase used to bind invader oligonucleotide 407) to invader oligonucleotide 411 may permit sequence specific coupling of the invader oligonucleotide 411 to its complementary sequence on single-stranded complementary nucleic acid molecule 406a. Moreover, the binding of invader oligonucleotide 407 to single-stranded template nucleic acid molecule 404 and the binding of invader oligonucleotide 411 to single-stranded complementary nucleic acid molecule 406a may occur simultaneously or may occur where one of the two invader oligonucleotides binds after the other binds. In addition, invader oligonucleotide 407 and invader oligonucleotide 411 may have the same sequence or may have different sequences.

The binding of invader oligonucleotide 407 to single-stranded template nucleic acid molecule 404 can expose a segment of single-stranded template nucleic acid molecule 404 that is complementary to a third primer 412. In some cases, the invader oligonucleotide 407 is of a different sequence from the third primer 412. In some cases, the invader oligonucleotide 407 may be the third primer 412. In some cases, the third primer 412 may have the same sequence as the first primer 402 or may have a different sequence than the first primer 402.

Similarly, the binding of invader oligonucleotide 411 to single-stranded complementary nucleic acid molecule 406a can expose a segment of single-stranded complementary nucleic acid molecule 406a that is complementary to a fourth primer 413. In some cases, the invader oligonucleotide 411 is of a different sequence from the fourth primer 413. In some cases, the invader oligonucleotide 411 may be the fourth primer 413. In some cases, the fourth primer 413 may have the same sequence as the second primer 403.

The third primer 412 can couple (e.g., anneal to) with its complementary, exposed segment of single-stranded template nucleic acid molecule 404 in a primer coupling phase 430a. Upon coupling of single-stranded template nucleic acid molecule 404 with the third primer 412, the third primer 412 can be extended 409 in a second primer extension reaction 440a (e.g., via the action of a polymerase (e.g., a strand-displacing polymerase)) to generate a second molecule of the double-stranded nucleic acid. The second molecule of the double-stranded nucleic acid comprises the single-stranded template nucleic acid molecule 404 and a second single-stranded complementary nucleic acid molecule. During the second primer extension reaction 440a, the action of a polymerase (e.g., a strand-displacing polymerase) displaces the single-stranded complementary nucleic acid molecule 406a from single-stranded template nucleic acid molecule 404. Moreover, at the conclusion of extension 409, invader oligonucleotide 407 can also be displaced from single-stranded template nucleic acid molecule 404 and, in some cases, recycled in a subsequent amplification cycle. Furthermore, invader oligonucleotide 407 may be configured such that invader oligonucleotide cannot be extended in a primer extension reaction. For example, invader oligonucleotide 407 may comprise a dideoxynucleotide (ddNTP) such that the presence of the ddNTP blocks extension of the invader oligonucleotide 407.

Similarly, the fourth primer 413 can couple (e.g., anneal to) with its complementary, exposed segment of single-stranded complementary nucleic acid molecule 406a in a primer coupling phase 430b. Upon coupling of single-stranded complementary nucleic acid molecule 406a with the fourth primer 413, the fourth primer 413 can be extended 408 in a third primer extension reaction 440b (e.g., via the action of a polymerase (e.g., a strand-displacing polymerase)) to generate a third molecule of the double-stranded nucleic acid. The third molecule of the double-stranded nucleic acid comprises the single-stranded complementary nucleic acid molecule 406a and its single-stranded complement. During the third primer extension reaction 440b, the action of a polymerase (e.g., a strand-displacing polymerase) displaces the single-stranded template nucleic acid molecule 404 from single-stranded complementary nucleic acid molecule 406a. Moreover, at the conclusion of extension 408, invader oligonucleotide 411 can also be displaced from single-stranded complementary nucleic acid molecule 406a and, in some cases, recycled in a subsequent amplification cycle. Furthermore, invader oligonucleotide 411 may be configured such that invader oligonucleotide cannot be extended in a primer extension reaction. For example, invader oligonucleotide 411 may comprise a dideoxynucleotide (ddNTP) such that the presence of the ddNTP blocks extension of the invader oligonucleotide 411. At the conclusion of the second and third primer extension reactions, the support 401 comprises the second and third double-stranded nucleic acid molecules, each configured in a loop (e.g., bridge) orientation.

One or more of phases 420, 430a/b, and 440a/b can repeat over a desired number or otherwise predetermined of cycles, such as at least 1, 2, 3, 4, 5, 6, 7, 8, 9, 10, 20, 30, 40, 50, 60, 70, 80, 90, 100, 200, 300, 400, or 500 cycles. Each double-stranded nucleic acid molecule generated in a previous cycle can be subject to phases 420, 430a/b, 440a/b resulting in exponential amplification. Additional molecules of the third primer 412 that are immobilized to the support 401, additional molecules of the fourth primer 413 that are immobilized to the support 401, recycled or additional molecules of invader oligonucleotide 407, and recycled or additional molecules of invader oligonucleotide 411 can permit repeated cycling. Amplification can proceed for as long as additional molecules of the third primer 412, the fourth primer 413, invader oligonucleotide 407, and invader oligonucleotide 411 are available, in addition to any other species (e.g., dNTPs, ATP, polymerase(s), cofactors, etc.) that may be useful for the amplification reaction. In some cases, the fourth primer 413 may be present in an amount greater than the third primer 412 or the third primer 412 may be present in an amount greater than the fourth primer 413, resulting in asymmetric amplification.

In some cases, the first primer 402 may have the same nucleic acid sequence of any of the second primer 403, the third primer 412, and the fourth primer 413. In some cases, the second primer 403 may have the same nucleic acid sequence of any of the first primer 402, the third primer 412, and the fourth primer 413. In some cases, the third primer 412 may have the same nucleic acid sequence of any of the first primer 402, second primer 403, and the fourth primer 413. In some cases, the fourth primer 413 may have the same nucleic acid sequence of any of the first primer 402, second primer 403, and the third primer 412. In some cases, the first primer 402 may have a different nucleic acid sequence from any of the second primer 403, the third primer 412, and the fourth primer 413. In some cases, the second primer 403 may have a different nucleic acid sequence from any of the first primer 402, the third primer 412, and the fourth primer 413. In some cases, the third primer 412 may have a different nucleic acid sequence from any of the first primer 402, the second primer 403, and the fourth primer 413. In some cases, the fourth primer 413 may have a different nucleic acid sequence from any of the first primer 402, the second primer 403, and the third primer 412.

Moreover, in some cases, amplification, as shown in FIG. 4, may be completed isothermally at an appropriate temperature, including an amplification temperature described elsewhere herein. Where the support is initially associated with only one single-stranded template nucleic acid molecule 404, clonal amplification of the single-stranded template nucleic acid molecule 404 can be achieved. As shown, nucleic acid is not released from the support 401 during each phase of amplification, resulting in confinement of the amplification reaction to the support 401.

Figure 9:
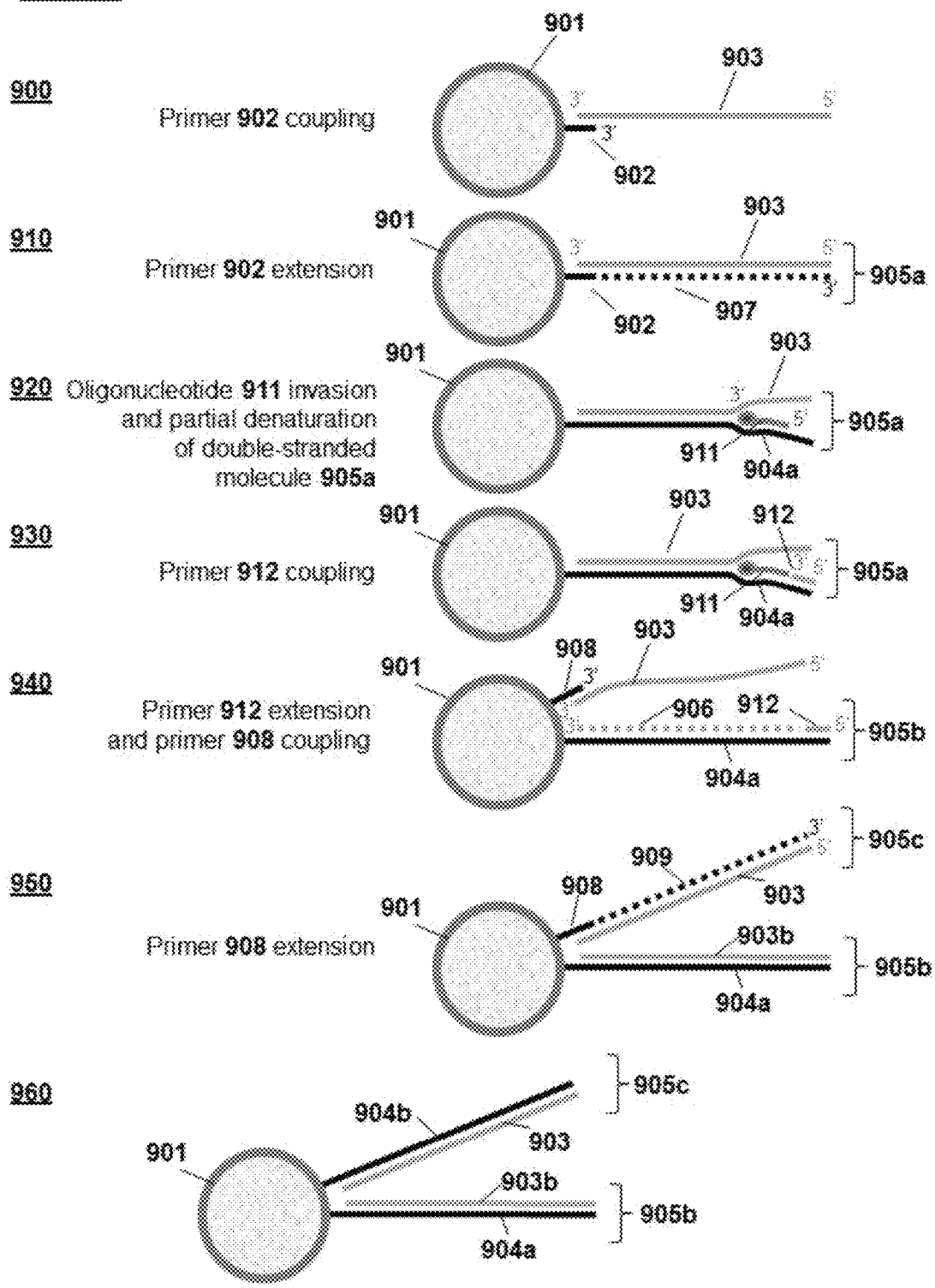
FIG. 9 is a schematic that illustrates an example method for nucleic acid amplification.

An additional example method for amplifying a nucleic acid sample is schematically depicted in FIG. 9. As shown in FIG. 9, a support (e.g., a bead or any other type of support described herein) 901 may comprise a first primer 902 that is immobilized to the surface of the support 901. The first primer 902 can couple to (e.g., anneal to, prime) a single-stranded template nucleic acid (e.g., a template oligonucleotide) molecule 903 that is derived from a nucleic acid sample in a primer coupling phase 900. In some cases, the first primer 902 is not capable of functioning as an invader species. In some cases, the single-stranded template nucleic acid molecule 903 is derived from a double-stranded nucleic acid molecule that is derived from the nucleic acid sample.

Following coupling of the single-stranded template nucleic acid molecule 903 to the first primer 902, the first primer 902 can be extended 907 in a primer extension reaction (e.g., via the action of a polymerase (e.g., a strand-displacing polymerase)) 910, to generate a first molecule 905a of a double-stranded nucleic acid, that comprises the single-stranded template nucleic acid molecule 903 and a single-stranded complementary nucleic acid molecule 904a.

An invader species (e.g., invader oligonucleotide 911 or a different type of invader species) may be capable of strand invasion and may be provided free from the support 901. In a strand invasion phase 920, the invader oligonucleotide 911 can at least partially denature the double-stranded nucleic acid molecule 905a by binding to its complementary sequence on single-stranded template nucleic acid molecule 904a. In some cases, the invader oligonucleotide may bind a complementary sequence on the single-stranded complementary nucleic acid molecule 903 instead. Strand-invasion of the double-stranded nucleic acid molecule 905a may be achieved, for example, via the transfer of thermal energy and/or the transfer of chemical energy. For example, the binding of a recombinase enzyme (e.g., a recombinase capable of utilizing a chemical energy source for function, such as, for example, adenosine triphosphate (ATP)) to the invader oligonucleotide 911 may permit sequence specific coupling of the invader oligonucleotide 911 to its complementary sequence on single-stranded template nucleic acid molecule 904a. The binding of invader oligonucleotide 911 to single-stranded template nucleic acid molecule 904a can expose a segment of the single-stranded template nucleic acid molecule 904a that is complementary to a second primer 912 provided in solution and free from the support 901. In some cases, the invader oligonucleotide is of the same sequence as the second primer 912 or is of a different sequence from the second primer 912. In some cases, the invader oligonucleotide is of the same sequence as the first primer 902 or is of a different sequence from the first primer 902. In some cases, the first primer 902 and the second primer 912 have the same nucleic acid sequence. In some cases, the first primer 902 and the second primer 912 have different nucleic acid sequences.

The second primer 912 can couple (e.g., anneal to) with its complementary, exposed segment of single-stranded template nucleic acid molecule 904a in a second primer coupling phase 930. Upon coupling of single-stranded template nucleic acid molecule 904a with the second primer 912, the second primer 912 can be extended 906 in a second primer extension reaction 940 (e.g., via the action of a polymerase (e.g., a strand-displacing polymerase)) to generate a second molecule 905b of the double-stranded nucleic acid. The second molecule 905b of the double-stranded nucleic acid comprises the single-stranded nucleic acid molecule 904a and a second single-stranded complementary nucleic acid molecule 903b. During the second primer extension reaction 940, the action of a polymerase (e.g., a strand-displacing polymerase) displaces the single-stranded template nucleic acid molecule 903 from single-stranded complementary nucleic acid molecule 904a, such that single-stranded template nucleic acid molecule 903 is released from single-stranded complementary nucleic acid molecule 904a.

Moreover, at the conclusion of extension 906, invader oligonucleotide 911 can also be displaced from single-stranded complementary nucleic acid molecule 904a and, in some cases, recycled in a subsequent amplification cycle. Furthermore, invader oligonucleotide 911 may be configured such that invader oligonucleotide 911 cannot be extended in a primer extension reaction. For example, invader oligonucleotide 911 may comprise a dideoxynucleotide (ddNTP) such that the presence of the ddNTP blocks extension of the invader oligonucleotide 911. Displacement of single-stranded template nucleic acid molecule 903 from the single-stranded complementary nucleic acid molecule 904a, may allow coupling (e.g., annealing) of the released single-stranded template nucleic acid molecule 903 to a third primer 908 that can be immobilized to the support 901. In some cases, the third primer 908 is not capable of strand-invasion. In some cases, the first primer and the third primer may have the same nucleic acid sequence. In some cases, the first primer and the third primer may have different nucleic acid sequences. In some cases, the second primer and the third primer may have the same nucleic acid sequence. In some cases, the second primer and the third primer may have different nucleic acid sequences.

The third primer 908 can be extended 909 in a third primer extension reaction 950 (e.g., via the action of a polymerase (e.g., a strand-displacing polymerase)) to generate a third molecule 905c of the double-stranded nucleic acid. After one cycle of amplification, the product 960 comprises support 901 coupled to two molecules 905b and 905c of the double-stranded nucleic acid.

One or more of phases 920, 930, 940, and 950 can repeat over a desired or otherwise predetermined number of cycles, such as at least 1, 2, 3, 4, 5, 6, 7, 8, 9, 10, 20, 30, 40, 50, 60, 70, 80, 90, 100, 200, 300, 400, or 500 cycles. Each double-stranded nucleic acid molecule generated in a previous cycle can be subject to phases 920, 930, 940, and 950, resulting in exponential amplification. Additional molecules of the second primer 912 in solution, recycled or additional molecules of invader oligonucleotide 911, and additional molecules of the third primer 908 (e.g., third primer 908 in solution) immobilized to the support 901 can permit repeated cycling. Amplification can proceed for as long as additional molecules of the second primer 912, the third primer 908, and the invader oligonucleotide 911 are available, in addition to any other species (e.g., dNTPs, ATP, polymerase(s), cofactors, etc.) that may be useful for the amplification reaction. In some cases, the third primer 908 may be present in an amount greater than the second primer 912 or the second primer 912 may be present in an amount greater than the third primer 908, resulting in asymmetric amplification.

Moreover, in some cases, amplification, as shown in FIG. 9, may be completed isothermally at an appropriate temperature, including an amplification temperature described elsewhere herein. Where the support is associated with only one single-stranded template nucleic acid molecule 903, clonal amplification of the single-stranded template nucleic acid molecule 903 can be achieved using, for example, a virtual well or confinement cell as described elsewhere herein. Furthermore, in some cases, the example methods of FIG. 2 and FIG. 9 may be combined by providing appropriate primers in both solution and immobilized to the support.

Methods described herein may be used to amplify a nucleic acid that can be derived, for example, from a nucleic acid sample. The nucleic acid may be any suitable form of nucleic acid, with non-limiting examples that include oligonucleotides, primers, nucleotides, deoxyribonucleic acid (DNA), ribonucleic acid (RNA), peptide polynucleotides, peptide nucleic acid (PNA), in whole or part, peptide nucleic acid (PNA) nucleotides, complementary DNA (cDNA), double-stranded DNA (dsDNA), single-stranded DNA (ss-DNA), plasmid DNA, cosmid DNA, chromosomal DNA, genomic DNA, viral DNA, bacterial DNA, mtDNA (mitochondrial DNA), messenger RNA (mRNA), ribosomal RNA (rRNA), transfer RNA (tRNA), nucleolar RNA (nRNA), small interfering RNA (siRNA), small nuclear RNA (snRNA), small nucleolar RNA (snoRNA), small cajal body-specific RNA (scaRNA), microRNA, double-stranded RNA (dsRNA), ribozymes, riboswitch and viral RNA, a locked nucleic acid (LNA) in whole or part, locked nucleic acid nucleotides, and any other type of nucleic acid analogue. In some cases a nucleic acid that is amplified may be pre-processed such that additional sequences (e.g., primer binding sequences, invader species binding sequences, etc.) are added to the nucleic acid prior to amplification. Such additional sequences may be added, for example, via ligation and/or one or more primer extension reactions.

In general, amplification methods described herein make use of one or more primers. Primers may be any suitable form of nucleic acid, including example types of nucleic acid described herein. Moreover, the length of a primer may vary depending upon the particular function of the primer in an amplification method. For example, a primer may have a length of 5-80 nucleotides, 10-60 nucleotides, 10-40 nucleotides, 10-20 nucleotides, or 12-15 nucleotides. In some examples, the length of a primer may be at least 5 nucleotides, at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, at least 55 nucleotides, at least 60 nucleotides, at least 70 nucleotides, at least 75 nucleotides, at least 80 nucleotides, or more. In some examples the length of a primer may be at most 80 nucleotides, at most 75 nucleotides, at most 70 nucleotides, at most 65 nucleotides, at most 60 nucleotides, at most 55 nucleotides, at most 50 nucleotides, at most 45 nucleotides, at most 40 nucleotides, at most 35 nucleotides, at most 30 nucleotides, at most 25 nucleotides, at most 20 nucleotides, at most 15 nucleotides, at most 10 nucleotides, or at most 5 nucleotides. In some examples, the length of a primer may be greater than or equal to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or more nucleotides.

Nucleic acid amplification methods described herein generally rely on the execution of one or more primer extension reactions. A primer used in a nucleic acid amplification reaction can be extended in a primer extension reaction. Prior to a primer extension reaction, a primer coupling phase can be completed in which a primer is coupled (e.g., anneals, hybridizes) to a template nucleic acid (e.g., a single-stranded template nucleic acid) molecule. Following the primer coupling phase, a primer extension reaction can commence in which additional nucleotides are added to the primer (e.g., via the action of a polymerase) in a template bound fashion to generate a double-stranded nucleic acid molecule that comprises a strand of nucleic acid that comprises the template nucleic acid and a strand of nucleic acid at least partially complementary to the template nucleic acid.

Following extension of the primer during the primer extension reaction, a denaturation phase can be completed in which the two strands of the double-stranded nucleic acid that are generated from extension of the primer are at least partially separated to generate single-stranded segments in each strand that are complementary to each other. The separated strands or segments of the strands that are separated can each be at least partially coupled with additional primers in a subsequent primer coupling phase and the coupled primers subject to subsequent primer extension reactions (e.g., via the action of a polymerase, such as a strand-displacing polymerase) to generate additional molecules of double-stranded nucleic acid.

The cycle of denaturation of a double-stranded nucleic acid molecule, primer coupling to at least a portion of the single-stranded segment(s) generated in one or both of the two strands of the double-stranded nucleic acid molecule, and extension of the primer(s) in a primer extension reaction can be repeated for a desired number of cycles for each double-stranded nucleic acid molecule generated in the previous cycle. Repetition can generally continue for as long as primers used in an amplification reaction are available for primer coupling and subsequent extension in a primer extension reaction in addition to any other species (e.g., an invader species, dNTPs, ATP, polymerase(s), co-factors, etc.) useful for amplification.

Moreover, primer coupling phases, primer extension reactions, and denaturation phases that are included in an amplification reaction may be performed in series or simultaneously. For example, one cycle of an amplification reaction may comprise generating a plurality of double-stranded nucleic acid molecules in series or simultaneously via one or more primer extension reactions. In cases where a plurality of double-stranded nucleic acid molecules are generated in series in an amplification cycle, for example, double-stranded nucleic acid molecules that are generated earlier in the cycle can be subject to the next cycle's primer coupling phases and primer extension reactions prior to the generation of the remaining double-stranded nucleic acid molecules produced in the cycle.

A primer coupling phase may be initiated in any suitable fashion. In general, a primer coupling phase can include the coupling of a template nucleic acid molecule (e.g., a single-stranded nucleic acid molecule) to a primer. For example, the template nucleic acid may anneal to the primer via at least partial hybridization of the template nucleic acid with the primer. In some cases, the template nucleic acid may be single-stranded and not coupled to a complementary strand of nucleic acid.

In other cases, the template nucleic acid may be a strand of a double-stranded nucleic acid such that the primer hybridizes with the nucleic acid strand and disrupts the nucleic acid strand's hybridization with its complementary strand. In such cases, the primer may function as an invader oligonucleotide (as described elsewhere herein) with, for example, the aid of a recombinase (as described elsewhere herein). Extension (e.g., via the action of a polymerase, such as a strand-displacing polymerase) of the primer in a primer extension reaction can displace the complementary strand and generate another complementary strand, thus, generating a new double-stranded nucleic acid molecule. In some cases, the complementary strand may be blocked (e.g., with a ddNTP or other type of nucleic acid blocking species/strategy described herein) such that it cannot be extended in a primer extension reaction and/or does not contain a primer binding sequence. Such a configuration of the complementary strand may be desired where confinement of a nucleic acid to a particular region (e.g., to a support, as described elsewhere herein) is desired. In other cases, an invader species (e.g., an invader oligonucleotide) may disrupt the nucleic acid strand's hybridization with its complementary strand, such that the primer can bind to the disrupted portion of either strand. In some cases, a single-stranded nucleic acid molecule coupled to a primer (including a primer coupled to a support) may be derived from a double-stranded nucleic acid molecule that is derived from a nucleic acid sample.

An example of a primer coupling phase as part of an example method of amplifying a nucleic acid sample is shown in FIG. 5. As shown in FIG. 5, a support 501 (e.g., a bead or any other type of support described herein) comprising a first primer 502 immobilized to the surface of the support 501 is provided 500. A double-stranded nucleic acid molecule 503 that comprises a single-stranded template nucleic acid molecule 504 and a single-stranded complementary nucleic acid molecule 505 and is derived from a nucleic acid sample is also provided 500 in solution. The single-stranded template nucleic acid molecule 504 comprises a sequence 506 at least partially identical to the sequence of a second primer. The single-stranded complementary nucleic acid molecule 505 comprises a sequence 511 identical to the sequence of the first primer 502 at its 5' end and is blocked at its 3' end with a blocker 507 that renders single-stranded complementary nucleic acid molecule 505 unable to be extended in a primer extension reaction. The blocker may be, for example, a dideoxynucleotide (ddNTP) or any other type of blocker described herein. Single-stranded complementary nucleic acid molecule 505 also does not comprise a primer binding.

In a primer invasion phase 510, first primer 502 can invade double-stranded nucleic acid molecule 503, with, for example, the aid of a recombinase (as described elsewhere herein), chemical energy transfer, or thermal energy transfer by binding to its complementary sequence on single-stranded template nucleic acid molecule 504. Following binding, the first primer 502 can be extended 508 (e.g., via the action of a polymerase, such as a strand-displacing polymerase) in a primer extension reaction 520 such that a new double-stranded nucleic acid molecule 509 is generated and immobilized to the support 501. The double-stranded nucleic acid molecule 509 can then be denatured (e.g., thermally, chemically—such as via treatment with sodium hydroxide (NaOH)) and subject to additional primer coupling phases (e.g., via the second primer complementary to sequence 506), and subsequent primer extension reactions. Extension 508 of the first primer 502 can also displace complementary nucleic acid strand 505 such that it becomes single-stranded and is released from the support 501. Because complementary nucleic acid strand 505 is blocked 507 and does not comprise an additional primer binding site it cannot participate in an additional primer extension reaction, resulting in confinement of amplification to the support 501.

The product 520 can participate in an additional nucleic acid amplification reaction, such as via invasion of double-stranded nucleic acid molecule 509 with an invader species (such as another copy of primer 502 or a different invader species such as an invader oligonucleotide free from the support 501) as described elsewhere herein (e.g., as in the example methods shown in FIG. 2 or FIG. 9). For example, double-stranded nucleic acid molecule 509 may be at least partially denatured by binding an invader species (e.g., an invader species free from the support 501) to at least a portion of single-stranded nucleic acid molecule 504 or single-stranded nucleic acid molecule 508, where binding of the invader species exposes a segment of single-stranded nucleic acid molecule 504 that is complementary to an additional primer (e.g., a primer similar to or identical in sequence to primer 502 or a primer of a different sequence than primer 702). The additional primer can couple to the segment of single-stranded nucleic acid molecule 504 and can be extended in a primer extension reaction to generate an additional double-stranded nucleic acid molecule that comprises single-stranded nucleic acid molecule 504 and a newly synthesized single-stranded nucleic acid molecule that is complementary to at least a portion of single-stranded nucleic acid molecule 504. The primer extension reaction also can separate single-stranded nucleic acid molecule 504 from single-stranded nucleic acid molecule 508.

Each additional double-stranded nucleic acid molecule that is generated may be subject to additional rounds of strand-invasion and primer extension reactions as above to generate additional double-stranded nucleic acid molecules on the support 501. In some cases, the invader species used to denature double-stranded nucleic acid molecule 509 and may a primer identical to primer 502 or may be a different invader species that may or may not be capable of extension during a primer extension reaction. In some cases, in addition or as an alternative, product 520 may also be subject to coupling with an additional solution phase double-stranded nucleic acid molecule (similar or identical to double-stranded nucleic acid molecule 503) derived from the nucleic acid sample and the process of strand-invasion of the double-stranded nucleic acid molecule followed by coupling to the support 501 via a primer similar to or identical to primer 502 may be completed.

An additional example of a primer coupling phase as part of an example method of amplifying a nucleic acid sample via strand-invasion is shown in FIG. 7. As shown in FIG. 7, a support 701 (e.g., a bead or any other type of support described herein) comprising a primer 702 immobilized to the surface of the support 701 is provided 700. A double-stranded nucleic acid molecule 703, derived from a nucleic acid sample, that comprises a single-stranded template nucleic acid molecule 704 and a single-stranded complementary nucleic acid molecule 705 is also provided 700 in solution along with an invader species (e.g., invader oligonucleotide 712 shown in FIG. 7 or any other type of invader species described herein) in solution and free from the support 701. Primer 702, coupled to the support 701, may or may not be capable of functioning as an invader species in a strand-invasion reaction. The single-stranded complementary nucleic acid molecule 705 may comprise a sequence 711 at least partially identical to the sequence of the primer 702 at its 5' end and may be blocked at its 3' end with a blocker 707 that renders single-stranded complementary nucleic acid molecule 705 unable to be extended in a primer extension reaction. The blocker may be, for example, a dideoxynucleotide (ddNTP) or any other type of blocker described herein. In the example shown in FIG. 7, single-stranded complementary nucleic acid molecule 705 also does not comprise a primer binding site.

In a strand invasion phase 710 and in solution, the invader oligonucleotide 712 can at least partially denature the double-stranded nucleic acid molecule 703 by binding to its complementary sequence on single-stranded template nucleic acid molecule 704. In some cases, the invader oligonucleotide may bind a complementary sequence on the single-stranded complementary nucleic acid molecule 705 instead. Strand-invasion of the double-stranded nucleic acid molecule 703 may be achieved, for example, via thermal energy transfer or chemical energy transfer. For example, the binding of a recombinase enzyme (e.g., a recombinase capable of utilizing a chemical energy source for function, such as, for example, adenosine triphosphate (ATP)) to the invader oligonucleotide 712 may permit sequence specific coupling of the invader oligonucleotide 712 to its complementary sequence on single-stranded template nucleic acid molecule 704. The binding of invader oligonucleotide 712 to single-stranded template nucleic acid molecule 704 can expose a segment of the single-stranded template nucleic acid molecule 704 that is complementary or at least partially complementary to primer 702. In some cases, the invader oligonucleotide is of the same sequence as the primer 702 or is of a different sequence from the primer 702.

Primer 702 can couple (e.g., anneal to) with its complementary, exposed segment of single-stranded template nucleic acid molecule 704 in a primer coupling phase 720. Upon coupling of single-stranded template nucleic acid molecule 704 with primer 702, the primer 702 can be extended 708 in a primer extension reaction 730 (e.g., via the action of a polymerase (e.g., a strand-displacing polymerase)) to generate a second molecule 709 of the double-stranded nucleic acid, which is coupled to the surface 701.

The second molecule 709 of the double-stranded nucleic acid comprises the single-stranded nucleic acid molecule 704 and a second single-stranded complementary nucleic acid molecule 715. During the primer extension reaction 730, the action of a polymerase (e.g., a strand-displacing polymerase) releases 730 the single-stranded template nucleic acid molecule 705 from single-stranded nucleic acid molecule 704, such that single-stranded nucleic acid molecule 705 is no longer a component of a double-stranded nucleic acid molecule. Moreover, at the conclusion of extension 708, invader oligonucleotide 712 can also be displaced from single-stranded complementary nucleic acid molecule 704. Furthermore, invader oligonucleotide 712 may be configured such that invader oligonucleotide 712 cannot be extended in a primer extension reaction. For example, invader oligonucleotide 712 may comprise a dideoxynucleotide (ddNTP) such that the presence of the ddNTP blocks extension of the invader oligonucleotide 712. Also, because single-stranded complementary nucleic acid molecule 705 is blocked 707 and does not comprise an additional primer binding site it cannot participate in an additional primer extension reaction.

The product 740 can participate in an additional nucleic acid amplification reaction, such as via invasion of double-stranded nucleic acid molecule 709 with an invader species (such as invader oligonucleotide 712 or a different invader species) as described elsewhere herein (e.g., as in the example methods shown in FIG. 2 or FIG. 9). For example, double-stranded nucleic acid molecule 709 may be at least partially denatured by binding an invader species (e.g., an invader species free from the support 701) to at least a portion of single-stranded nucleic acid molecule 704 or single-stranded nucleic acid molecule 715, where binding of the invader species exposes a segment of single-stranded nucleic acid molecule 704 that is complementary to an additional primer (e.g., a primer similar to or identical in sequence to primer 702 or a primer of a different sequence than primer 702). The additional primer can couple to the segment of single-stranded nucleic acid molecule 704 and can be extended in a primer extension reaction to generate an additional double-stranded nucleic acid molecule that comprises single-stranded nucleic acid molecule 704 and a newly synthesized single-stranded nucleic acid molecule that is complementary to at least a portion of single-stranded nucleic acid molecule 704. When a strand-displacing polymerase is utilized during the primer extension reaction, the primer extension reaction also can separate single-stranded nucleic acid molecule 704 from single-stranded nucleic acid molecule 715.

Each additional double-stranded nucleic acid molecule that is generated may be subject to additional rounds of strand-invasion and primer extension reactions as above to generate additional double-stranded nucleic acid molecules on the support 701. In some cases, the invader species used to denature double-stranded nucleic acid molecule 709 and may be identical to invader oligonucleotide 712 or may be a different invader species that may or may not be capable of extension during a primer extension reaction. In some cases, in addition or as an alternative, product 740 may also be subject to coupling with an additional solution phase double-stranded nucleic acid molecule (similar or identical to double-stranded nucleic acid molecule 703) derived from the nucleic acid sample and the process of strand-invasion of the additional double-stranded nucleic acid molecule followed by coupling to the support 701 via a primer similar to or identical to primer 702 may be completed.

Solution phase amplification of the double-stranded nucleic acid molecule 703 (e.g., a parent double-stranded nucleic acid molecule) via an invader species (e.g., an invader oligonucleotide, such as, for example, invader oligonucleotide 712), followed by coupling of the amplicons to the support 701, via the same invader species or a different invader species, as shown in FIG. 7, is also envisioned. For example, one or more cycles of nucleic acid amplification via strand-invasion (e.g., via invader oligonucleotide 712 or via a different invader species) of double-stranded nucleic acid molecule 703 may be performed in solution such that amplicons of double-stranded nucleic acid molecule 703 are produced in solution. Amplification in solution may proceed by providing solution-phase primers at least partially complementary to regions of strands 704 and 705 of double-stranded nucleic acid molecule 703 (e.g., a pair of primers, one primer at least partially complementary to sequence 711 (and, thus, at least partially identical in sequence to primer 702) and one primer partially complementary to sequence 706 of the double-stranded nucleic acid molecule 703).

Following the generation of double-stranded amplicons, a support 701 comprising a plurality of primers 702 can be provided to the double-stranded amplicons, such that one or more of the double-stranded amplicons undergoes a further round of amplification via strand-invasion with invader oligonucleotide 712 (or a different invader species), with primers 702 binding to invaded amplicons as described above. The bound primers 702 can be extended, as in FIG. 7, to generate additional double-stranded amplicons coupled to the support 701. In some cases, the additional amplicons coupled to the support may participate in one or more further rounds of strand invasion-based amplification (or any other suitable type of amplification reaction), such as for example, the example strand-invasion based amplification method depicted in FIG. 2 or FIG. 9 or any other suitable amplification method described herein. Alternatively or in addition, the method may be repeated entirely for one or more cycles to generate additional double-stranded amplicons coupled to the support 701. Moreover, amplification may be completed isothermally or non-isothermally.

Figure 8:
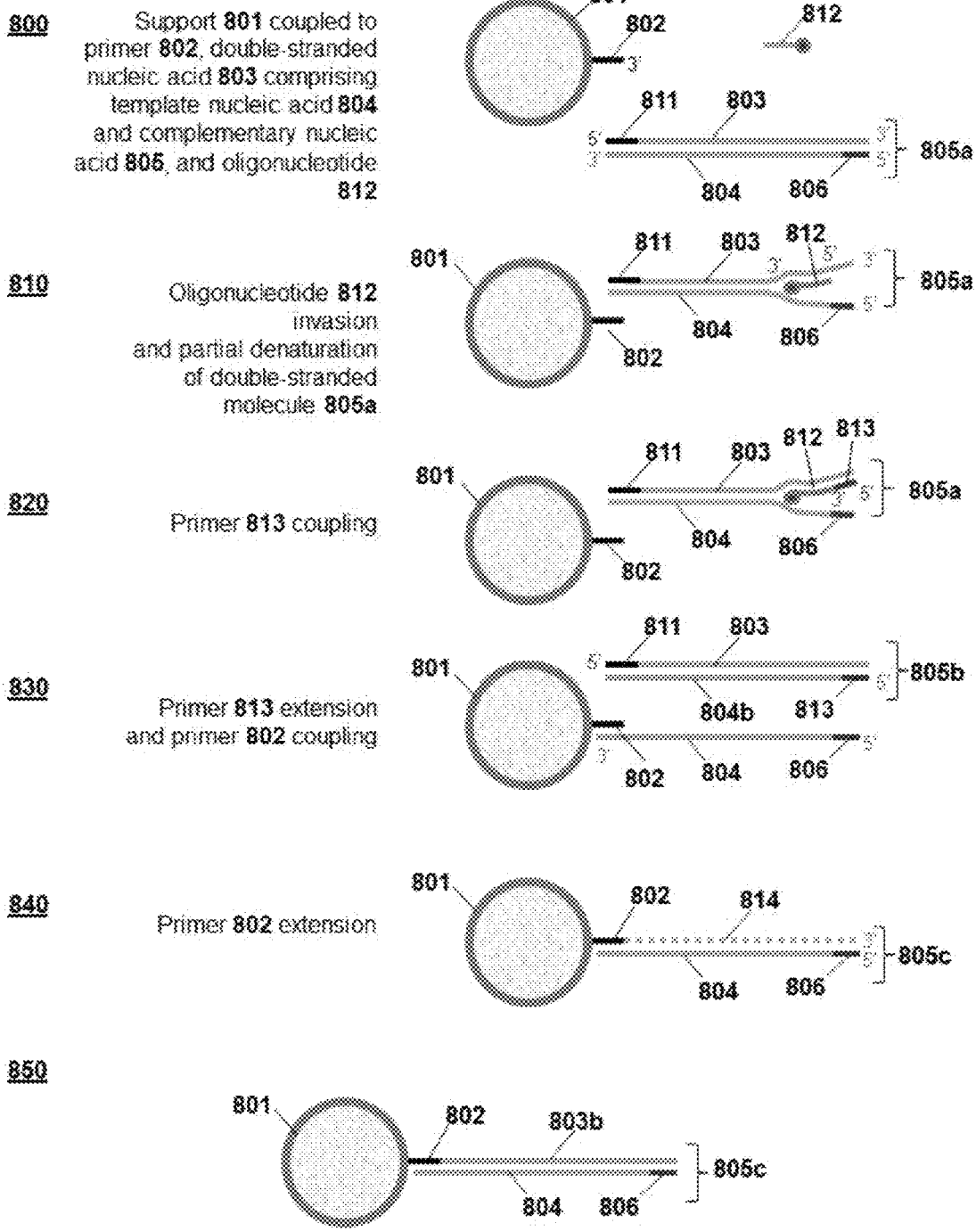
FIG. 8 is a schematic that illustrates an example primer coupling phase and method of nucleic acid amplification.

An additional example of a primer coupling phase as part of an example method of amplifying a nucleic acid sample is shown in FIG. 8. As shown in FIG. 8, a support 801 (e.g., a bead or any other type of support described herein) comprising a first primer 802 immobilized to the surface of the support 801 is provided 800. A double-stranded nucleic acid molecule 805a, derived from a nucleic acid sample, that comprises a single-stranded nucleic acid molecule 804 and a single-stranded complementary nucleic acid molecule 803 may also be provided 800 in solution, along with an invader species (e.g., invader oligonucleotide 812 or any other type of invader species described herein) in solution and free from the support 801. A second primer 813 may also be provided in solution separate from the first primer 802. The single-stranded template nucleic acid molecule 804 comprises a sequence 806 at least partially identical to the sequence of the second primer 813. In some cases, the first primer 802 and the second primer 813 have the same nucleic acid sequence or have different nucleic acid sequences. The single-stranded complementary nucleic acid molecule 803 comprises a sequence 811 at least partially identical to the sequence of the first primer 802 at its 5' end. The invader oligonucleotide 812 may be blocked (e.g., at its 3' end) with a blocker rendering it unable to be extended in a primer extension reaction.

In a strand invasion phase 810 and in solution, the invader oligonucleotide 812 can at least partially denature the double-stranded nucleic acid molecule 805*a* by binding to its complementary sequence on single-stranded nucleic acid molecule 803. In some cases, the invader oligonucleotide may bind a complementary sequence on the single-stranded nucleic acid molecule 804 instead. Strand-invasion of the double-stranded nucleic acid molecule 805*a* may be achieved, for example, via thermal energy transfer or chemical energy transfer. For example, the binding of a recombinase enzyme (e.g., a recombinase capable of utilizing a chemical energy source for function, such as, for example, adenosine triphosphate (ATP)) to the invader oligonucleotide 812 may permit sequence specific coupling of the invader oligonucleotide 812 to its complementary sequence on single-stranded nucleic acid molecule 803. The binding of invader oligonucleotide 812 to single-stranded nucleic acid molecule 803 can expose a segment of the single-stranded nucleic acid molecule 803 that is complementary to 806. In some cases, the invader oligonucleotide is of the same sequence as the first primer 802 or is of a different sequence from the first primer 802. In some cases, the first primer 802 may not be capable of functioning as an invader species.

The second primer 813, provided in solution, can couple (e.g., anneal to) with its complementary, exposed segment of single-stranded nucleic acid molecule 803 in a first primer coupling phase 820. In some cases, the invader oligonucleotide 812 is of the same sequence as the second primer 813 or is of a different sequence from the second primer 813. In some cases, the first primer 802 and/or the second primer 813 are not capable of functioning as an invader species. Upon coupling of single-stranded template nucleic acid molecule 803 with the second primer 813, the second primer 813 can be extended in a first primer extension reaction 830 (e.g., via the action of a polymerase (e.g., a strand-displacing polymerase)) to generate a second molecule 805*b* of the double-stranded nucleic acid in solution.

Double-stranded nucleic acid molecule 805*b* comprises single-stranded nucleic acid molecule 803 and a new single-stranded molecule 804*b* that is at least partially complementary to single-stranded nucleic acid molecule 803. Moreover, in cases where a strand-displacing polymerase is used, the first primer extension reaction 830 can release single-stranded nucleic acid molecule 804 from single-stranded nucleic acid molecule 803. The released single-stranded nucleic acid molecule 804 may couple (e.g., anneal to) with primer 802 in a primer coupling phase 830. The second molecule 805*b* of the double-stranded nucleic molecule that is generated in solution can undergo an additional round of strand-invasion to generate an additional double-stranded nucleic acid molecule as described above for the first molecule 805*a* of the double-stranded nucleic acid.

In a second primer extension phase 840 the first primer 802 may be extended 814 (e.g., via the action of a polymerase (e.g., a strand-displacing polymerase)) to generate a third molecule, 805*c*, of the double-stranded nucleic acid molecule. The third molecule, 805*c*, of the double-stranded nucleic acid comprises the single-stranded nucleic acid molecule 804 and a second single-stranded complementary nucleic acid molecule 803*b*.

The product 850 can then participate in an additional nucleic acid amplification reaction, such as via invasion of double-stranded nucleic acid molecule 805*c* with an invader species (e.g., invader oligonucleotide 812 or a different invader species) as described elsewhere herein (e.g., as in the example methods shown in FIG. 2 or FIG. 9). For example, double-stranded nucleic acid molecule 805*c* may be at least partially denatured by binding an invader species (e.g., an invader species free from the support 801) to at least a portion of single-stranded nucleic acid molecule 804 or single-stranded nucleic acid molecule 803*b*, where binding of the invader species exposes a segment of single-stranded nucleic acid molecule 804 that is complementary to an additional primer (e.g., a primer similar to or identical in sequence to primer 802 or a primer of a different sequence than primer 802). The additional primer can couple to the segment of single-stranded nucleic acid molecule 804 and can be extended in a primer extension reaction to generate an additional double-stranded nucleic acid molecule that comprises single-stranded nucleic acid molecule 804 and a newly synthesized single-stranded nucleic acid molecule that is complementary to at least a portion of single-stranded nucleic acid molecule 804. When a strand-displacing polymerase is utilized during the primer extension reaction, the primer extension reaction also can separate single-stranded nucleic acid molecule 804 from single-stranded nucleic acid molecule 803*b*.

Each additional double-stranded nucleic acid molecule that is generated may be subject to additional rounds of strand-invasion and primer extension reactions as above to generate additional double-stranded nucleic acid molecules on the support 801. In some cases, the invader species used to denature double-stranded nucleic acid molecule 805*c* and may be identical to invader oligonucleotide 812 or may be a different invader species that may or may not be capable of extension during a primer extension reaction. In some cases, in addition or as an alternative, product 850 may also be subject to coupling with an additional solution phase double-stranded nucleic acid molecule (similar or identical to double-stranded nucleic acid molecule 805*a*) derived from the nucleic acid sample and the process of strand-invasion of the additional double-stranded nucleic acid molecule followed by coupling to the support 801 via a primer similar to or identical to primer 802 may be completed. Moreover, in some cases, the example methods depicted in FIG. 7 and FIG. 8 may be combined by providing the appropriate components where desired. Moreover, amplification may be completed isothermally or non-isothermally.

Solution phase amplification of the double-stranded nucleic acid molecule 805*a* via an invader species (e.g., an invader oligonucleotide such as, for example, invader oligonucleotide 812) to generate amplicons of the double-stranded nucleic acid molecule 805*a* (e.g., a parent double-stranded nucleic acid molecule), followed by subjecting the amplicons to the example process shown in FIG. 8 is also envisioned. For example, one or more cycles of nucleic acid amplification via strand-invasion (e.g., via invader oligonucleotide 812 or via a different invader species) of double-stranded nucleic acid molecule 805*a* may be performed in solution such that a number of amplicons of the double-stranded nucleic acid molecule 805*a* are generated in solution. Amplification in solution may proceed by providing solution-phase primers at least partially complementary to regions of strands 803 and 804 of double-stranded nucleic acid molecule 805a (e.g., a pair of primers, one primer at least partially complementary to sequence 811 (and, thus, at least partially identical in sequence to primer 802) and one primer partially complementary to sequence 806 of the double-stranded nucleic acid molecule 805a).

The amplicons can then be subject to an additional round of strand-invasion based amplification such that single-stranded nucleic acid molecules comprising a sequence at least partially complementary to primer 802 are released into solution. Following the generation of released single-stranded nucleic acid molecules, a support 801 comprising a plurality of primers 802 can be provided to the released single-stranded molecules, such that one or more of the released single-stranded molecules binds with a primer 802 immobilized to the support 801. The bound primers 802 can be extended, as in FIG. 8, to generate additional double-stranded amplicons coupled to the support 801. In some cases, the additional amplicons coupled to the support may participate in one or more further rounds of strand invasion-based amplification (or any other suitable type of amplification reaction) such as for example, the example strand-invasion based amplification method depicted in FIG. 2 or FIG. 9 (e.g., via invader oligonucleotide 812 or a different invader species). Alternatively or in addition, the method may be repeated entirely for one or more cycles to generate additional double-stranded amplicons coupled to the support 801.

A primer extension reaction generally makes use of a polymerase that is capable of extending a primer via the addition of nucleotides to the primer in a template bound fashion. In some cases, the polymerase may be a strand-displacing polymerase capable of displacing one strand of a double-stranded nucleic acid via the incorporation of nucleotides to a primer hybridized with the other strand of the double-stranded nucleic acid. Non-limiting examples of polymerases that may be suitable in an amplification reaction described herein include Taq polymerase, Pfu polymerase, Tth polymerase, VENT polymerase, DEEPVENT polymerase, EX-Taq polymerase, Expand polymerases, LA-Taq polymerase, Sso polymerase, Poc polymerase, Mth polymerase, Pho polymerase, ES4 polymerase, Tru polymerase, Tac polymerase, Tne polymerase, Tma polymerase, Tli polymerase, Pab polymerase, Tih polymerase, Tfi polymerase, Platinum Taq polymerases, Hi-Fi polymerase, Tbr polymerase, Pfutubo polymerase, Pyrobest polymerase, Pwo polymerase, Tfl polymerase, KOD polymerase, Bst polymerase, Sac polymerase, and variants, modified products, homologues, and derivatives thereof. Non-limiting examples of strand-displacing polymerases include Bsu polymerase I (e.g., Bsu DNA polymerase I), Large Fragment (*Bacillus subtilits*), Bst polymerase (e.g., Bst DNA polymerase), *Staphylococcus aureus* polymerase, PolI polymerase, phi 29 polymerase, Large Fragment (*Bacillus stearothermophilus*), Klenow Fragment (3'→5' exo-), and variants, modified products, homologues, derivatives, and combinations thereof. Other reagents may be used in an amplification reaction described herein with non-limiting examples that include deoxyribonucleotides (dNTPs), other enzymes (e.g., reverse transcriptase), co-factors (e.g., cationic co-factors such as, for example, magnesium), and suitable buffers for amplification.

A denaturation phase may be initiated in any suitable fashion. In some examples, an elevation in temperature may be used to at least partially separate two strands of a double-stranded nucleic acid. In other examples, chemical strategies, such a treatment of a double-stranded nucleic acid with a denaturation agent (e.g., sodium hydroxide (NaOH)) may be used to at least partially separate two strands of a double-stranded nucleic acid. In other examples, an invader species may be used to at least partially separate or denature two strands of a double-stranded nucleic acid. In general, an invader species generally refers to a species that may bind to a portion of a nucleic acid strand of a double-stranded nucleic acid such that one or more single-stranded segments are generated in the one or both of the two strands of the double-stranded nucleic acid. The invader species may be designed to be sequence specific such that the invader species binds to a specific sequence of a nucleic acid strand or may be designed such that it binds a nucleic acid strand randomly. Any suitable invader species may be used to at least partially denature a double-stranded nucleic acid with non-limiting examples of an invader species that include an oligonucleotide (e.g., an invader oligonucleotide), a nucleic acid that comprises a peptide nucleic acid (PNA), a nucleic acid that comprises a locked nucleic acid (LNA), and a sequence-specific single-stranded nucleic acid binding protein, and combinations thereof. Moreover, in some cases, an invader species may be coupled to a support used in an amplification reaction. In some cases, an invader species may be free from a support (e.g., in solution) used in an amplification reaction.

An invader species may be a nucleic acid that comprises a peptide nucleic acid (PNA) or a locked nucleic acid (LNA). In some examples, the binding of a nucleic acid comprising a PNA or an LNA may depend upon thermal energy fluctuations in an amplification reaction. Thermal energy fluctuations can give rise to, for example, nucleic acid breathing (e.g., DNA breathing), in which the component strands of a double-stranded nucleic acid can transiently adopt varied conformations resulting in the transient denaturation of the component strands (e.g., during an unbinding phase) followed by re-binding (e.g., during a re-binding phase, such as, for example, a re-hybridization phase) of the component strands with each other. During an unbinding phase of nucleic acid breathing, a nucleic acid comprising an LNA or PNA can bind to one or both of the component strands of a double-stranded nucleic acid such that re-binding of the component strands can be at least partially blocked, resulting in at least partial denaturation of the double-stranded nucleic acid. An LNA or PNA invader species can be designed to be sequence-specific such that it binds a specific sequence on a strand of nucleic acid or may be designed to bind randomly. In some embodiments, only a portion of the sequence of an LNA or PNA may be designed to bind to a strand of nucleic acid.

An invader species may be a sequence-specific, single-stranded nucleic acid binding protein (e.g., a sequence-specific, single-stranded DNA binding protein). A sequence-specific, single-stranded nucleic acid binding protein generally refers to a protein capable of binding a particular sequence of a nucleic acid strand. In some cases, a sequence-specific, single-stranded nucleic acid binding protein may be capable of both specific and non-specific binding. A sequence-specific, single-stranded nucleic acid binding protein can also make use of nucleic acid breathing (e.g., DNA breathing) such that during an unbinding phase of nucleic acid breathing, the sequence-specific single-stranded nucleic acid binding protein can bind to one or both of the component strands of a double-stranded nucleic acid such that re-binding of the component strands can be at least partially blocked, resulting in at least partial denaturation of the double-stranded nucleic acid. Non-limiting examples of sequence-specific single-stranded nucleic acid binding proteins include Y-box binding proteins (e.g., a Y-box binding protein comprising a cold shock domain), YB-1, Pur α, Pur β, CspB, variants thereof, modified products thereof, homologues thereof, and derivatives thereof. In some cases, a sequence-specific single-stranded nucleic acid binding protein may be a protein engineered to recognize one or more specific sequences of a nucleic acid.

An invader species may be an invader oligonucleotide. An invader oligonucleotide generally refers to an oligonucleotide that can bind to a strand of a double-stranded nucleic acid such that the double-stranded nucleic acid is at least partially denatured. In some cases, an invader oligonucleotide may be a primer used as part of an amplification reaction as depicted in the example shown in FIG. 1 and described above. In other cases, an invader oligonucleotide may be an oligonucleotide different from a primer used as part of an amplification reaction as depicted, for example, in the examples shown in FIG. 2, FIG. 3, FIG. 4, and FIG. 9 described above. In such cases, an invader oligonucleotide may be configured to bind a nucleic acid strand at a site at least partially different from a primer binding site of the nucleic acid strand. Such a design may be useful in cases where a primer cannot function as an invader oligonucleotide. Moreover, in some cases, an invader oligonucleotide may be present in solution or may be immobilized to a support, including supports described herein. In some cases, an invader oligonucleotide may comprise a peptide nucleic acid (PNA) or a locked nucleic acid (LNA). An invader oligonucleotide can be designed to be sequence-specific such that it binds a specific sequence on a strand of nucleic acid or may be designed to bind randomly. In some embodiments, only a portion of the sequence of an invader oligonucleotide may be designed to bind to a strand of nucleic acid.

Furthermore, in some cases, an invader oligonucleotide may be designed such that it cannot be extended with the incorporation of additional nucleotides such, as, for example, via the action of a polymerase. For example, an invader oligonucleotide may comprise a dideoxynucleotide (ddNTP) that blocks extension of the invader oligonucleotide. In some cases, a ddNTP may be a 3' ddNTP, with the last 1, 2, 3, 4, or 5 nucleotides at the 3' end having a phosphorothioate linkage, which can prevent degradation. Other modifications can be made to a ddNTP that imparts a blocking function with non-limiting examples of such modifications that include 3' biotin, 3' amino modifier, 3' phosphate, 3' dithiol, 3' dark quencher, 3' fluorophores, and 3' spacers. An invader oligonucleotide that cannot be extended may be desirable in cases where an invader oligonucleotide binds downstream from a primer that is desired for extension and/or in cases where extension of the invader oligonucleotide is not desirable.

The suitability of an oligonucleotide (including a primer) to function as an invader oligonucleotide may depend, at least in part, on the length of the oligonucleotide. The length of an oligonucleotide that is suitable for the oligonucleotide to function as an invader oligonucleotide may depend on, for example, the sequence of the oligonucleotide, the nucleotide composition of the oligonucleotide, any source of energy used, the binding sequence on a target strand of nucleic acid, any enzyme(s) (e.g., recombinase(s)) or other species used to facilitate invasion, etc. In some cases, the length of an oligonucleotide suitable for functioning as an invader oligonucleotide may be 10-80 nucleotides in length, 20-80 nucleotides in length, 20-60 nucleotides in length, 20-50 nucleotides in length, or 20-40 nucleotides in length. In some examples, the length of a nucleic acid suitable for functioning as an invader oligonucleotide may be at least 10 nucleotides, at least 20 nucleotides, at least 25 nucleotides, at least 30 nucleotides, at least 35 nucleotides, at least 40 nucleotides, at least 45 nucleotides, at least 50 nucleotides, at least 55 nucleotides, at least 60 nucleotides, at least 65 nucleotides, at least 70 nucleotides, at least 75 nucleotides, at least 80 nucleotides, or more. In some examples, the length of an oligonucleotide suitable for functioning as an invader oligonucleotide may be greater than or equal to about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or more nucleotides. The nucleotide lengths described above for invader oligonucleotides may also be applicable to invader species that are a nucleic acid comprising LNAs or PNAs.

Depending upon, for example, the particular amplification reaction and the particular primer(s) used in an amplification reaction, an oligonucleotide (including a primer) used in an amplification reaction may not be capable of functioning as an invader oligonucleotide. The use of an oligonucleotide not capable of functioning as an invader oligonucleotide may be desirable, for example, where primer invasion is not desirable, primer invasion results in the release of amplification products from a support associated with an amplification reaction, and/or in some situations where a different invader species is used. In some examples, a primer of insufficient length may not be capable of functioning as an invader oligonucleotide. For example, the length of an oligonucleotide not capable of functioning as an invader oligonucleotide may be about 2-25 nucleotides in length, may be 10-25 nucleotides in length, 10-20 nucleotides in length, or 12-15 nucleotides in length. In some examples, the length of an oligonucleotide not capable of functioning as an invader oligonucleotide may be at most 25 nucleotides, at most 20 nucleotides, at most 15 nucleotides, at most 10 nucleotides, at most 5 nucleotides, or less. In some cases, an oligonucleotide not capable of functioning as an invader oligonucleotide may be great than or equal to about 2, 3, 4, 5, 6, 7, 8, 9, 10, 11, 12, 13, 14, 15, 16, 17, 18, 19, 20, 21, 22, 23, 24, or 25 nucleotides in length.

The capability of a nucleic acid to function as an invader oligonucleotide may depend on the transfer of energy. For example, the binding of an invader oligonucleotide to a strand of nucleic acid may be achieved with the aid of thermal energy transfer, such as, for example the addition of heat to a reaction. In other cases, the binding of an invader oligonucleotide to a strand of nucleic acid may be achieved through the transfer of chemical energy, such as for example, the expenditure of chemical energy by an enzyme whose function aids in the binding of the invader oligonucleotide. For example, the source or form of chemical energy may be adenosine triphosphate (ATP) and an enzyme whose function aids in the binding of an invader oligonucleotide to a strand of nucleic acid may hydrolyze the ATP for function.

An example type of enzyme that can expend chemical energy for function and can aid in the binding of an invader oligonucleotide to a strand of nucleic acid is a recombinase. A recombinase generally refers to an enzyme that facilitates nucleic acid strand exchange reactions that can occur during a nucleic acid recombination reaction. In some examples, a recombinase can expend chemical energy (e.g., in the form of ATP) for function. For example, ATP hydrolysis by a recombinase can permit binding (and unbinding) of a nucleic acid and can also deliver energy useful for nucleic acid strand exchange. In some cases, though, a recombinase may function in the absence of chemical energy expenditure (e.g., such as the expenditure of ATP) or any other type of energy expenditure.

A recombinase may be capable of both a sequence homology search and nucleic acid strand exchange, which both can facilitate sequence-specific nucleic acid single strand (e.g., single-stranded DNA) invasion of a nucleic acid duplex (e.g., double-stranded DNA). For example, a recombinase can first bind along a single-stranded nucleic acid molecule such as, for example, a single-stranded DNA molecule, to form a protein (e.g., nucleoprotein) filament. In a homology search, the protein filament can scan along a duplex nucleic acid molecule, such as, for example, a double-stranded DNA molecule, for a sequence match with the single-stranded nucleic acid molecule of the protein filament. If a matching sequence is found during the homology search, nucleic acid strand exchange can proceed whereby the single-stranded nucleic acid molecule of the protein replaces its sequence match in the nucleic acid duplex. In some cases, the single-stranded nucleic acid molecule can serve as a primer and may be extended (e.g., via the action of a polymerase, such as a strand-displacing polymerase) in a primer extension reaction. In other cases, the single-stranded nucleic acid molecule may be blocked (e.g., via blocking species/strategies described elsewhere herein) such that it cannot be extended in a primer extension reaction.

Non-limiting examples of recombinases include Cre recombinase, Hin recombinase, RecA recombinase (e.g., RecA found in *E. coli* bacteria), RAD51 recombinase, Tre recombinase, FLP recombinase, UvsX recombinase (e.g., from bacteriophage T4), DMC1 recombinase, variants thereof, modified products thereof, homologues thereof, derivatives thereof, and combinations thereof. In some cases, binding of a recombinase to a nucleic acid may be achieved with the aid of one or more auxiliary proteins. Non-limiting examples of such auxiliary proteins include SSB protein (e.g., bacterial SSB protein), gp32 protein (e.g., from bacteriophage T4), recombinase loaders such UvsY (e.g., from T4 bacteriophages), RecR (e.g., from bacteria), and RecO (e.g., from bacteria), variants thereof, modified products thereof, homologues thereof, derivatives thereof, and combinations thereof.

A recombinase can bind a nucleic acid such that the nucleic acid can function as an invader oligonucleotide. Upon binding of the oligonucleotide, the oligonucleotide-recombinase complex can then interact with the target nucleic acid strand in sequence-specific fashion, such that the oligonucleotide binds (e.g., invades) to the strand of nucleic acid and at least partially denatures the double-stranded nucleic acid comprising the target nucleic acid strand.

In some cases, the function of an oligonucleotide as an invader oligonucleotide with the aid of a recombinase may be controlled at least partially by the oligonucleotide size. The length of an oligonucleotide that is suitable for the oligonucleotide to function as an invader oligonucleotide may depend on, for example, the sequence of the oligonucleotide, the nucleotide composition of the oligonucleotide, the particular recombinase used, the binding sequence on a target strand of nucleic acid, the particular recombinase(s) used, etc. For example, the length of an oligonucleotide (including a primer) that can function as an invader oligonucleotide with the aid of a recombinase may be 10-80 nucleotides in length, 20-80 nucleotides in length, 20-60 nucleotides in length, 20-50 nucleotides in length, 20-40 nucleotides in length, 30-40 nucleotides in length, or 30-34 nucleotides in length. In some examples, the length of an oligonucleotide suitable for functioning as an invader oligonucleotide with the aid of a recombinase may be at least 10 nucleotides, may be at least 20 nucleotides, at least 25 nucleotides, at least 30 nucleotides, at least 35 nucleotides, at least 40 nucleotides, at least 45 nucleotides, at least 50 nucleotides, at least 55 nucleotides, at least 60 nucleotides, at least 65 nucleotides, at least 70 nucleotides, at least 75 nucleotides, at least 80 nucleotides, or more. In some examples, the length of an oligonucleotide suitable for functioning as an invader oligonucleotide with the aid of a recombinase may be greater than or equal to about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or more nucleotides.

For example, the length of an oligonucleotide (including a primer) that cannot function as an invader oligonucleotide with the aid of a recombinase may be 2-25 nucleotides in length, 10-25 nucleotides in length, 10-20 nucleotides in length, or 12-15 nucleotides in length. In some examples, the length of an oligonucleotide that cannot function as an invader oligonucleotide with the aid of a recombinase may be at most 25, at most 20, at most 15, at most 10, at most 5 nucleotides, or less. In some examples, the length of an oligonucleotide that cannot function as an invader oligonucleotide with the aid of a recombinase may be greater than or equal to about 2, 3, 4, 5, 6, 7, 8, 9, 10, 11, 12, 13, 14, 15, 16, 17, 18, 19, 20, 21, 22, 23, 24, or 25 nucleotides.

Upon at least partial denaturation of a double-stranded nucleic acid by an invader species, single-stranded segments of the two strands of the double-stranded nucleic acid may be generated. In cases where an invader species is a primer, the primer may bind to its target nucleic acid strand of the double-stranded nucleic acid and the primer can then be extended (e.g., via the action of a strand-displacing polymerase) in a primer extension reaction such that the original two strands of the double-stranded nucleic acid are separated and a new molecule of double-stranded nucleic acid is generated using the target nucleic acid strand as a template. The non-target strand of the double-stranded nucleic acid can be displaced and rendered single-stranded as shown, for example, in the examples depicted in FIG. 1 described above. The single-stranded non-target strand can then be coupled with an appropriate primer and the primer extended to generate another new molecule of the double-stranded nucleic acid as shown, for example, in the example depicted in FIG. 1 described above.

In cases where an invader species is not a primer used in an amplification reaction, the invader species may bind to its target nucleic acid strand of the double-stranded nucleic acid to generate one or more single-stranded segments in the component strands of the double-stranded nucleic acid. A primer can bind to a single-stranded segment of the target strand and the primer can be extended (e.g., via the action of a strand-displacing polymerase) in a primer extension reaction such that the original two strands of the double-stranded nucleic acid are separated and a new molecule of double-stranded nucleic acid is generated (e.g., as shown in the example depicted in FIGS. 2-3 and FIG. 9 described above). The invader species can also be displaced from the target strand via the completion of the primer extension reaction. The displaced invader species can be recycled for subsequent rounds of strand-invasion. The non-target strand of the double-stranded nucleic acid can be displaced and rendered single-stranded as shown in the examples depicted in FIGS.

2-3 and FIG. 9 described above. The non-target strand can then be primed with an appropriate primer and the primer extended to generate another new molecule of the double-stranded nucleic acid as shown, for example, in the examples depicted in FIG. 2-3 and FIG. 9 described above.

In some cases, two or more invader species may be used to denature a double-stranded nucleic acid. The same type of invader species may be used (e.g., a plurality of invader oligonucleotides, the same invader oligonucleotides) or different types of invader species may be used (e.g., an invader oligonucleotide used in combination with a sequence-specific single-stranded nucleic acid binding protein). Where two or more invader species are used to denature a double-stranded nucleic acid, the two or more invader species may bind the same strand of nucleic acid of a double-stranded nucleic acid or some invader species may bind one strand and other invader species may bind the other strand.

As shown in the example depicted in FIG. 4 and explained above, an invader species (e.g., an invader oligonucleotide) can bind to both strands of a double-stranded nucleic acid to generate single-stranded segments of both strands of the double-stranded nucleic acid. Appropriate primers can be coupled to each single-stranded region and the primers can each be extended (e.g., via the action of a strand-displacing polymerase) to generate additional molecules of double-stranded nucleic acid. Displaced invader species that result from the completion of the primer extension reactions can be recycled for subsequent rounds of denaturation. In some cases, two or more invader oligonucleotides are used to denature a double-stranded nucleic acid. The two or more invader oligonucleotides may be the same invader oligonucleotide or may be different invader oligonucleotides. Moreover, each invader oligonucleotide of the two or more invader oligonucleotides may bind its respective strand of nucleic acid with the aid of a recombinase, including recombinases described elsewhere herein. In some cases, the same recombinase may be used to bind each invader oligonucleotide. In some cases, different recombinases may be used to bind each invader oligonucleotide.

Amplification may be associated with one or more supports. For example, one or more primers and/or other nucleic acids used in or generated in an amplification reaction may be immobilized to the surface of a support, such that at least a portion of the amplification products generated in a nucleic acid amplification reaction are also immobilized to a support. Any suitable support may be used and the support may comprise any suitable surface for amplification. Nucleic acids (e.g., primers, invader species, etc.) and other species may be immobilized to a support in any suitable fashion including both non-covalently (e.g., hybridization, annealing, ionic interactions, van der Waals forces, protein-ligand interactions (e.g., biotin-streptavidin) etc.) and covalently (e.g., linkers, carbon covalent bonds, ligation, primer extension reactions, etc.). Non-limiting examples of supports include a bead, a particle, a microparticle, a nanoparticle, a metal surface, a plastic surface, a polymeric surface, a glass surface, a slide surface, a pixel of an array, a sensor, an electrode (e.g., an electrode of a sensor), a well surface, a spot surface, a planar surface, and combinations thereof. In some cases, a nucleic acid (e.g., a primer) or other species may be directly coupled (e.g., via covalent or non-covalent attachment) to a support. In some cases, a nucleic acid (e.g., a primer) may be coupled indirectly to a support, such as, for example, via a linker.

In some cases, a single nucleic acid template (e.g., a single-stranded nucleic acid template or a template nucleic acid included as part of a double-stranded nucleic acid molecule) may be associated with a support such that amplification of the nucleic acid template with a primer immobilized to the surface of the support results in clonal amplification of the nucleic acid template. Moreover, in some cases, the association of amplification with a support may result in confinement of an amplification reaction to the support, such that nucleic acids (e.g., amplification products, primers, templates, etc.) are not released from the support during each cycle of an amplification reaction. Such functionality may be desirable in cases where multiple amplification reactions are conducted simultaneously for different nucleic acid templates. In some cases, confinement of an amplification reaction to a support may be achieved with the aid of a virtual well or confinement cell that generates, for example, an electric field. Virtual wells and confinement cells are described in more detail in PCT Patent Application No. PCT/US2011/054769, which is entirely incorporated herein by reference.

For example, an integrated system that is capable of amplifying a nucleic acid may comprise an array. Examples of such systems are described for example, in PCT Patent Application No. PCT/US2011/054769, PCT Patent Application No. PCT/US2012/039880, PCT Patent Application No. PCT/US2012/067645, and U.S. patent application Ser. No. 13/481,858, each of which is entirely incorporated herein by reference. At each pixel or position of at least a subset of the pixels of the array, a separate nucleic acid amplification reaction may occur where a different nucleic acid template is amplified. Moreover, each pixel may comprise a support that comprises one or more immobilized primers (such as in amplification methods described herein) that participate in an amplification reaction. The support may be, for example, a bead positioned at each pixel, a sensor surface (e.g., the surface of an electrode of a sensor), or the surface of the array. Amplification methods described herein, in which nucleic acid is not released from a support during each amplification cycle, may be useful in minimizing the diffusion of nucleic acids from one pixel of an array to the other. Such diffusion can, for example, contaminate other amplification reactions where clonal amplification of the pixel's associated template is desired.

In some cases, one or more primers used in an amplification reaction may be immobilized to a support while other primers used in the amplification reaction may be present in solution. In some cases, all primers used in an amplification reaction may be immobilized to a support or all primers used in an amplification reaction may be in solution. Any desirable combination of primers immobilized to a support and primers in solution may be used for amplification. For example, an amplification reaction may make use of one or more primers (e.g., forward primers) immobilized to a support and one or more primers (e.g., reverse primers) present in solution as shown, for example, in the examples depicted in FIG. 1, FIG. 2, and FIG. 9 described above. In some cases, the number of primers in solution may be greater than the number of primers immobilized to a support, resulting in asymmetric amplification. In some cases, the number of primers immobilized to a support may be greater than the number of primers in solution, resulting in asymmetric amplification. In some cases, the number of one type of primer used in an amplification reaction may be greater than the number of another type of primer used in an amplification reaction, resulting in asymmetric amplification. In some cases, the primers immobilized on a support may be the same primers in solution or the primers immobilized on a support may be different than the primers in solution.

In some cases, a plurality of primers used in an amplification reaction may be immobilized to a support. In some cases, a plurality of primers used in an amplification reaction may be in solution. The plurality of primers may be the same type of primers or the plurality of primers may comprise two or more types of primers. In some cases, a plurality of types of primers used in an amplification reaction may be immobilized to a support and another plurality of primers used in the amplification reaction may be in solution. For example, an amplification reaction may make use of one or more primers of one sequence (e.g., forward primers) and one or more second primers of another sequence (e.g., reverse primers), where both types of primers are immobilized to the surface of a support or one of the two primers is in solution. In some cases, one type of primer may be immobilized to the support in a greater amount than the other type(s) of primers immobilized to the support. In cases where a plurality of types of primers are immobilized to a support, looped (e.g., bridged) amplification products may be generated as shown in the examples depicted in FIG. 3 and FIG. 4 and described above. In some cases, a primer immobilized to a support may function as an invader oligonucleotide during a denaturation phase with, in some cases, the aid of a recombinase. In some cases, a primer immobilized to a support may not be capable of functioning as an invader oligonucleotide during a denaturation phase.

Furthermore, a template nucleic acid (e.g., a single-stranded template nucleic acid) may be coupled to a support via the coupling of the template nucleic acid to a primer immobilized to the support. Any suitable strategy for coupling a template nucleic acid to a primer may be used, with non-limiting examples that include non-covalent coupling (e.g., without the formation of a covalent bond) such as hybridization (e.g., annealing) or covalent coupling (e.g., with the formation of a covalent bond) such as ligation and a primer extension reaction.

Amplification methods described herein may be completed non-isothermally or may be completed isothermally. A non-isothermal amplification reaction generally refers to an amplification reaction that occurs with the cyclic addition and removal of thermal energy (e.g., heat), resulting in temperature changes to drive different phases of the amplification reaction. An isothermal amplification reaction generally refers to an amplification reaction that occurs without the addition and/or removal (e.g., including cyclic addition and/or removal) of thermal energy (e.g., heat) during different phases of the amplification reaction. In general, the phases of an isothermal amplification reaction generally occur at the same temperature, or at substantially the same temperature. In some examples, a given temperature is selected for amplification and maintained constant or substantially constant during isothermal amplification.

In cases where an amplification reaction is completed isothermally, the temperature at which the amplification reaction occurs may vary depending upon, for example, the particular template being amplified, the particular polymerase employed, the particular primers utilized, etc. For example, the temperature at which an isothermal amplification reaction occurs may be from 5 degrees Celsius (° C.) to 80° C., from 20° C. to 80° C., from 20° C. to 60° C., from 20° C. to 40° C., from 30° C. to 45° C., from 30° C. to 40° C., or from 32° C. to 42° C. In some examples, the temperature at which an isothermal amplification reaction occurs may be at most 80° C., at most 70° C., at most 60° C., at most 50° C., at most 40° C., at most 30° C., at most 20° C., at most 15° C., at most 10° C., at most 5° C., or less. In some examples, the temperature at which an isothermal amplification reaction occurs may be at least 5° C., at least 10° C., at least 15° C., at least 20° C., at least 30° C., at least 40° C., at least 50° C., at least 60° C., at least 70° C., at least 80° C., or more. In some examples, the temperature at which an isothermal amplification reaction occurs may be 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or more.

Amplification reactions described herein generally rely on the completion of one or more reaction cycles, such as for example, in which each cycle may include one or more primer coupling phases, one or more primer extension reactions, and/or one or more denaturation phases. The time it takes for an individual cycle of an amplification reaction to occur may vary depending upon, for example, the particular template being amplified, the particular polymerase employed, the particular primers utilized, concentration of one or more reagent(s), the reaction temperature, etc. For example, the time it takes for an individual cycle of an amplification reaction to occur may be from 0.001 seconds ("s") to 5 minutes ("min"), 0.01 s to 5 min, 0.5 s to 1 min, 0.5 s to 1 min, 0.5 s to 30 s, 0.5 s to 10 s, or 0.5 s to 1 s. In some examples, the time it takes for an individual cycle of an amplification reaction to occur may be at most 15 min, at most 14 min, at most 13 min, at most 12 min, at most 11, at most 10 min, at most 9 min, at most 8 min, at most 7 min, at most 6 min, 5 min, at most 4 min, at most 3 min, at most 2 min, at most 1 min, at most 55 s, at most 50 s, at most 45 s, at most 40 s, at most 35 s, at most 30 s, at most 25 s, at most 20 s, at most 15 s, at most 10 s, at most 5 s, at most at most 4 s, at most 3 s, at most 2 s, at most 1 s, at most 0.5 s, at most 0.1 s, at most 0.01 s, at most 0.001 s, or less. In some examples, the time it takes for an individual cycle of an amplification reaction to occur may be at least 0.001 s, at least 0.01 s, at least 0.1 s, at least 0.5 s, at least 1 s, at least 2 s, at least 3 s, at least 4 s, at least 5 s, at least 10 s, at 15 s, at least 20 s, at least 25 s, at least 30 s, at least 35 s, at least 40 s, at least 45 s, at least 50 s, at least 55 s, at least 1 min, at least 2 min, at least 3 min, at least 4 min, at least 5 min, at least 6 min, at least 7 min, at least 8 min, at least 9 min, at least 10 min, at least 11 min, at least 12 min, at least 13 min, at least 14 min, at least 15 min, or longer. In some examples, the time it takes for an individual cycle of an amplification reaction to occur may be greater than or equal to about 0.001 s, 0.05 s, 0.01 s, 0.05 s, 0.1 s, 0.2 s, 0.3 s, 0.4 s, 0.5 s, 0.6 s, 0.7 s, 0.8 s, 0.9 s, 1.0 s, 1.5 s, 2.0 s, 2.5 s, 3.0 s, 3.5 s, 4.0 s, 4.5 s, 5.0 s, 5.5 s, 6.0 s, 6.5 s, 7.0 s, 7.5 s, 8.0 s, 8.5 s, 9.0 s, 9.5 s, 10.0 s, 15.0 s, 20.0 s, 30.0 s, 40.0 s, 50.0 s, 60.0 s, 2 min, 3 min, 4 min, 5 min, 6 min, 7 min, 8 min, 9 min, 10 min, 11 min, 12 min, 13 min, 14 min, 15 min, or longer.

Control Systems

Figure 6:
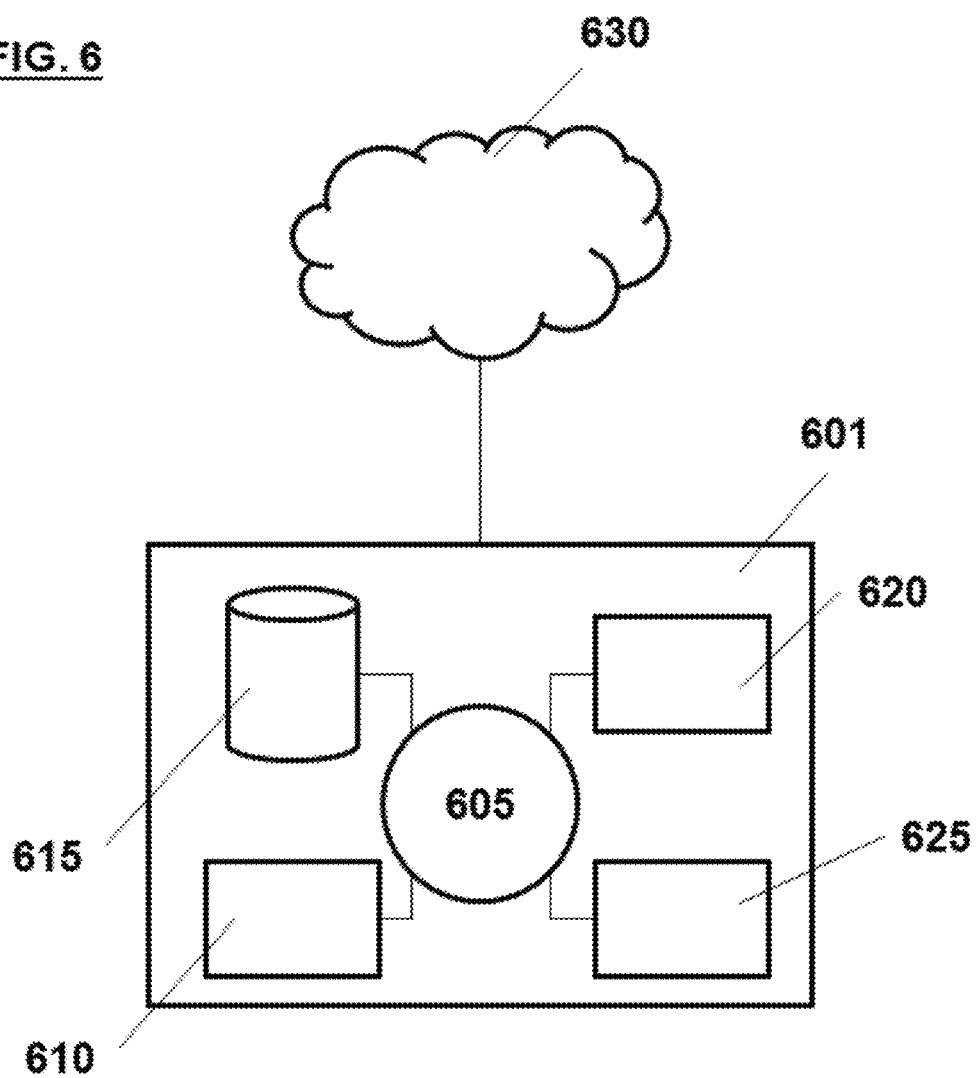
FIG. 6 shows an example computer system that is programmed or otherwise configured to conduct nucleic acid amplification.

The present disclosure provides computer control systems that are programmed to implement methods of the disclosure. FIG. 6 shows a computer system 601 that is programmed or otherwise configured to conduct nucleic acid amplification. The computer system 601 can regulate various aspects of sample processing, such as, for example, heat flow (e.g., heating or cooling), fluid flow, fluid mixing, fluid separation and reaction (e.g., nucleic acid amplification).

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. Examples of operations performed by the CPU 605 can include fetch, decode, execute, and writeback.

The storage unit 615 can store files, such as drivers, libraries and saved programs. The storage unit 615 can store programs generated by users and recorded sessions, as well as output(s) associated with the programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

EXAMPLES

Example 1: Invader-Based, Asymmetric Amplification in Solution

A series of solution amplification reactions were performed in reaction mixtures having 50 μL total volume. FIG. 10 (panel A) schematically depicts various components in the reaction mixture. Commercially available solid-phase reagent pellets (TwistDx) were used in reaction mixtures along with template nucleic acid (e.g., represented schematically as template nucleic acid 1001 in FIG. 10 (panel A)), appropriate primers (e.g., represented schematically as primers 1002 and 1003 in FIG. 10 (panel A)), invader oligonucleotide (e.g., represented schematically as invader oligonucleotide 1004 in FIG. 10 (panel A)) and other liquid reagents. Each solid-phase reagent pellet included a recombinase, a polymerase, a single-strand binding protein, ATP, dNTPs, an ATP regeneration system and other components. Each reaction mixture included 1 solid-phase reaction pellet, 29.5 μL rehydration buffer, 2.5 μL magnesium acetate (MgOAc) for reaction activation and 1 pg of double-stranded Template 1 (sequence shown in Table 1) as amplification starting material. The reaction mixtures were distinguished by the presence, type and/or concentration of primer 1002 (e.g., A12, A13, A14 or A15 in Table 1), primer 1003 (e.g., B12, B15 or B30 in Table 1) and invader oligonucleotide 1004 (e.g., InvB1 in Table 1) used in a given reaction mixture. Table 2 summarizes the components of each reaction mixture (items 2-9 and 13-20 in Table 2) with respect to primer 1002, primer 1003 and invader oligonucleotide 1004 and the concentration of each species used.

The amplification reactions were executed as follows: all components in a given reaction mixture, except for reagent pellet and MgOAc, were well-mixed together to generate an initial mixture. The reagent pellet was then added to the initial mixture and the reagent pellet dissolved into the initial mixture by pipetting forming a reaction mixture. To initiate amplification reactions, MgOAc was added to the reaction mixtures. Following initiation of reactions, reaction mixtures were incubated at 36° C. for 30 min. After incubation, reactions were quenched by the addition of EDTA (final concentration: 50 mM) to each reaction mixture. Amplified nucleic acid in each reaction mixture was purified using AMPure XP beads (Beckman Coulter). Purified nucleic acid was analyzed on 4% pre-cast Agarose E-Gel® (Thermo Scientific) gels.

FIG. 10 (panel B) shows photographs of the gels. Each of the lane numbers shown in FIG. 10 (panel B) corresponds with its respective entry in Table 1. Items 1-11 shown in Table 2 are depicted in panel I of FIG. 10 (panel B), whereas items 12-20 shown in Table 2 are depicted in panel II of FIG. 10 (panel B). Results indicate that invader-based, asymmetric amplification was achieved in solution.

TABLE 1

| | | |
|---|---|---|
| A12 | 5'-CCATCTCATCCC-3' | (SEQ ID NO: 1) |
| A13 | 5'-CCATCTCATCCCT-3' | (SEQ ID NO: 2) |
| A14 | 5'-CCATCTCATCCCTG-3' | (SEQ ID NO: 3) |
| A15 | 5'-CCATCTCATCCCTGC-3' | (SEQ ID NO: 4) |
| B12 | 5'-CCTATCCCCTGT-3' | (SEQ ID NO: 5) |
| B15 | 5'-CCTATCCCCTGTGTG-3' | (SEQ ID NO: 6) |
| B30 | 5'-CCTATCCCCTGTGTGCCT-3' | (SEQ ID NO: 7) |
| InvB1 | 5'-CCTAATCTTAGCGCCTTGGCAGTCTCAGAGACC ACTAACTGCGTATC*A*A*C*/3ddC/-3' | (SEQ ID NO: 8) |
| InvB2 | 5'-CCTAATCTTACTTGGCAGTCTCAGAGACCACTA ACTGCGTATC*A*A*C*/3ddC/-3' | (SEQ ID NO: 9) |
| InvB3 | 5'-CTCATTGGATCGCCTTGGCAGTCTCAGAGACCA CTAACTGCGTAT*C*A*A*/3ddC/-3' | (SEQ ID NO: 10) |
| InvB4 | 5'-CATTGGATCGTGCCTTGGCAGTCTCAGAGACCA CTAACTGCGTATC*A*A*/3ddC/-3' | (SEQ ID NO: 11) |
| InvA1 | 5'-CACTATTGTCTCGTGTCTCCGACTCAGTGACCT GCCTCAACCTCC*T*G*T*/3ddC/-3' | (SEQ ID NO: 12) |
| Template 1 | 5'-CCTATCCCCTGTGTGCCTTGGCAGTCTCAGAGACCACTAACTGCGT ATCAACCCAACCAACCCCTTTTAAAATTTTTTCCCCCCAAAAAACTGAG TCGGAGACACGCAGGGATGAGATGG-3' | (SEQ ID NO: 13) |
| Template 2 | 5'-CCATCTCATCCCTGCGTGTCTCCGACTCAGTGACCTGCCTCAACCT CCTGTCAATGCTGGCGGCGGCTCTGGTGGTGGTTCTGGTGGCGGCTCTG AGGGTTGATACGCAGTTAGTGGTCTCTGAGACTGCCAAGGCACACAGGG GATAGG-3' | (SEQ ID NO: 14) |

TABLE 2

| | | | |
|---|---|---|---|
| 1 | ladder | | |
| 2 | A12 (500 nM) | InvB1 (400 nM) | |
| 3 | A15 (500 nM) | InvB1 (400 nM) | |
| 4 | B12 (500 nM) | InvB1 (400 nM) | |
| 5 | B15 (500 nM) | InvB1 (400 nM) | |
| 6 | A12 (500 nM) | B12 (500 nM) | InvB1 (200 nM) |
| 7 | A12 (500 nM) | B12 (500 nM) | InvB1 (800 nM) |
| 8 | A12 (1 μM) | B12 (1 μM) | InvB1 (800 nM) |
| 9 | A15 (500 nM) | B12 (500 nM) | InvB1 (800 nM) |

TABLE 2-continued

| | | |
|---|---|---|
| 10 | empty lane | |
| 11 | template only control | |
| 12 | ladder | |
| 13 | A12 (500 nM) | B12 (500 nM) |
| 14 | A13 (500 nM) | B12 (500 nM) |
| 15 | A14 (500 nM) | B12 (500 nM) |
| 16 | A15 (500 nM) | B12 (500 nM) |
| 17 | A12 (500 nM) | B30 (500 nM) |
| 18 | A13 (500 nM) | B30 (500 nM) |
| 19 | A14 (500 nM) | B30 (500 nM) |
| 20 | A15 (500 nM) | B30 (500 nM) |

Example 2: Invader-Based Amplification on a Surface

A series of surface-tethered amplification reactions were performed in reaction mixtures having 50 µL total volume. Commercially available solid-phase reagent pellets (TwistDx) were used in reaction mixtures along with template nucleic acid (Template 2—see Table 2 for sequence), primer A15 (see Table 1 for sequence) in solution, primer B15 (see Table 1 for sequence) covalently coupled to 1 µm diameter beads (MyOne, Thermo Scientific), invader oligonucleotide (e.g., InvB1, InvB2, InvB3, InvB4—see Table 1 for sequences) and other liquid reagents. Each solid-phase reagent pellet included a recombinase, a polymerase, a single-strand binding protein, ATP, dNTPs, an ATP regeneration system and other components. Each reaction mixture included 1 solid-phase reaction pellet, 29.5 µL rehydration buffer, 2.5 µL magnesium acetate (MgOAc) for reaction activation, 60 pg of double-stranded Template 2 as amplification starting material and approximately 20 million beads covalently coupled to B15 primers. The reaction mixtures were distinguished by the presence and/or concentration of primer A15 and the presence, type and/or concentration of invader oligonucleotide (e.g., InvB1, InvB2, InvB3 or InvB4 in Table 1) used in a given reaction mixture. Table 3 summarizes the components of each reaction mixture (items 2-9 in Table 3) with respect to primer A15 and invader oligonucleotide (e.g., InvB1, InvB2, InvB3 or InvB4 in Table 1) and the concentration of each species used.

Prior to initiation of amplification reactions, double-stranded Template 2 was hybridized to bead-bound B15 primers using a temperature ramp. After hybridization, beads were washed to remove remaining non-hybridized Template 2. The amplification reactions were executed as follows: all components in a given reaction mixture, except for reagent pellet and MgOAc, were well-mixed together to generate an initial mixture. The reagent pellet was then added to the initial mixture and the reagent pellet dissolved into the initial mixture by pipetting forming a reaction mixture. To initiate amplification reactions, MgOAc was added to the reaction mixtures. Following initiation of reactions, reaction mixtures were incubated at 40° C. for 55 min. After incubation, reactions were quenched by the addition of EDTA (final concentration: 50 mM) to each reaction mixture. Complement nucleic acid strands generated during amplification were denatured from the beads using 100 mM NaOH and analyzed on a 10% Criterion™ TBE-Urea Gel (Biorad) (FIG. 2) via PAGE.

Figure 11:
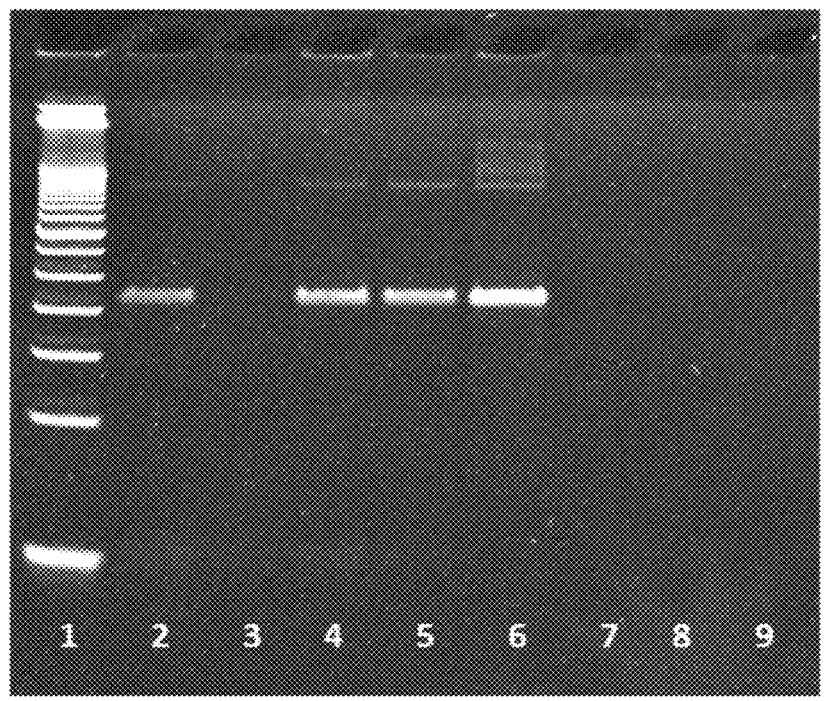
FIG. 11 depicts a photograph of a gel as described in Example 2.

FIG. 11 shows photographs of the resulting gel. Each of the lane numbers shown in FIG. 11 corresponds with its respective entry in Table 3. Results indicate that invader-based amplification was achieved on a surface.

TABLE 3

| | | |
|---|---|---|
| 1 | ladder | |
| 2 | A15 (500 nM) | InvB1 (400 nM) |
| 3 | A15 (500 nM) | InvB2 (400 nM) |
| 4 | A15 (500 nM) | InvB3 (400 nM) |
| 5 | A15 (500 nM) | InvB4 (400 nM) |
| 6 | A15 (500 nM) | InvA1 (400 nM) |
| 7 | InvB2 (400 nM) | |
| 8 | InvB3 (400 nM) | |
| 9 | InvB4 (400 nM) | |

Example 3: Asymmetric Amplification on a Surface

A series of surface-tethered amplification reactions were performed in reaction mixtures having 50 µL total volume. Commercially available solid-phase reagent pellets (TwistDx) were used in reaction mixtures along with template nucleic acid (Template 1—see Table 2 for sequence), primer A15 (see Table 1 for sequence) in solution, primer B30 (see Table 1 for sequence) covalently coupled to 1 µm diameter beads (MyOne, Thermo Scientific) and other liquid reagents. Each solid-phase reagent pellet included a recombinase, a polymerase, a single-strand binding protein, ATP, dNTPs, an ATP regeneration system and other components. Each reaction mixture included 1 solid-phase reaction pellet, 29.5 µL rehydration buffer, 2.5 µL magnesium acetate (MgOAc) for reaction activation, 20 pg of double-stranded Template 1 as amplification starting material and approximately 20 million beads covalently coupled to B30 primers. A15 (see Table 1 for sequence) was used as second amplification primer, present at a final concentration of 500 µM in solution.

For each reaction mixture and prior to initiation of amplification reactions, double-stranded Template 1 was hybridized to bead-bound B30 primers using a temperature ramp in an initial reaction mixture. After hybridization, beads were washed to remove remaining non-hybridized Template 1. All components in the initial reaction mixture, except for reagent pellet and MgOAc, were well-mixed together. A reagent pellet was then added to the initial mixture and the reagent pellet dissolved into the initial mixture by pipetting to generate a reaction mixture. To initiate an amplification reaction, MgOAc was added to the reaction mixture. Following initiation of the amplification reaction, the reaction mixture was split into two aliquots. The first aliquot of the reaction mixture, comprising 10 µL of the reaction mixture, was mixed with SYBR Green dye (Thermo Scientific) for real time detection of amplification in an RT-PCR instrument and incubated at 40° C. for 55 min. The second aliquot of the reaction mixture, comprising the remaining reaction mixture, was incubated on a heat block at 40° C. for 55 min. Amplification reactions in the second aliquot were quenched with the addition of EDTA (final concentration: 50 mM). Complement nucleic acid strands generated during amplification were denatured from the beads using 100 mM NaOH and analyzed on a 10% Criterion™ TBE-Urea Gel (Biorad) via PAGE.

Figure 12:
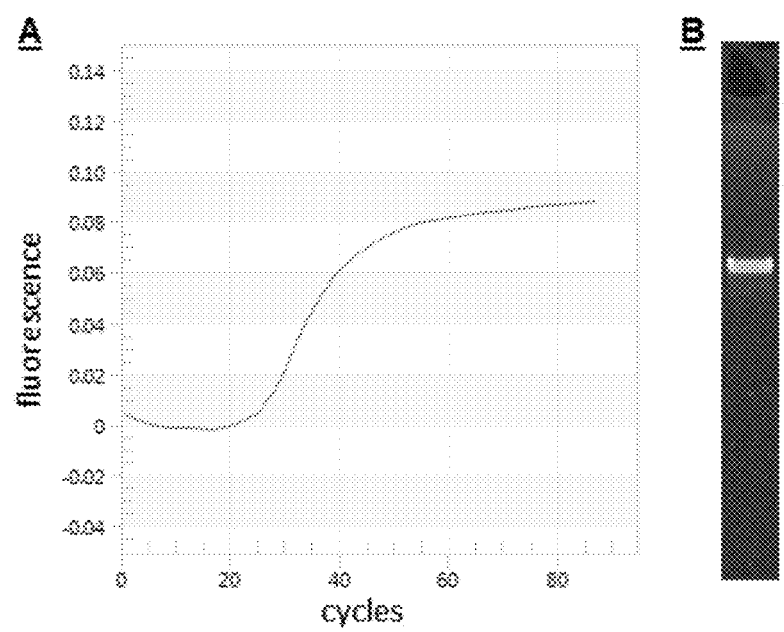
FIG. 12 (panel A) shows a plot depicting time-dependent fluorescence measurements obtained from RT-PCR analysis as described in Example 3.

FIG. 12 (panel A) shows plot depicting time-dependent fluorescence measurements obtained from RT-PCR analysis of the first aliquot of reaction mixture. Cycle time was approximately 35 seconds. FIG. 12 (panel B) depicts a photograph of the resulting gel obtained from the second aliquot of reaction mixture after 20 min incubation. Results indicate that asymmetric amplification on a surface was achieved.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for amplifying a nucleic acid sample, comprising:
   a) providing a support comprising a first primer and a second primer;
   b) coupling the first primer to a first single-stranded nucleic acid molecule that is derived from the nucleic acid sample;
   c) performing a first primer extension reaction using the first primer to generate a first double-stranded nucleic acid molecule comprising the first single-stranded nucleic acid molecule and a second single-stranded nucleic acid molecule that is complementary to at least a portion of the first single-stranded nucleic acid molecule;
   d) at least partially denaturing the first double-stranded nucleic acid molecule by binding an invader species to at least a portion of the first or second single-stranded nucleic acid molecule, wherein the invader species is different from the second primer, which binding exposes a segment of the first single-stranded nucleic acid molecule that is complementary to the second primer; and
   e) coupling the second primer to the segment of the first single-stranded nucleic acid molecule and performing a second primer extension reaction using the second primer to generate a second double-stranded nucleic acid molecule comprising the first single-stranded nucleic acid molecule and a third single-stranded nucleic acid molecule that is complementary to at least a portion of the first single-stranded nucleic acid molecule, wherein the second primer extension reaction separates the second single-stranded nucleic acid molecule from the first single-stranded nucleic acid molecule.

2. The method of claim 1, further comprising:
   (f) coupling a third primer to the second single-stranded nucleic acid molecule and performing a third primer extension reaction using the third primer to generate a third double-stranded nucleic acid molecule comprising the second single-stranded nucleic acid molecule and a fourth single-stranded nucleic acid molecule that is complementary to at least a portion of the second single-stranded nucleic acid molecule.

3. The method of claim 2, wherein in (d), the method further comprises binding the invader species to at least a portion of the first single-stranded nucleic acid molecule and binding another invader species to at least a portion of the second single-stranded nucleic acid molecule, wherein the binding of the another invader species exposes a segment of the second single-stranded nucleic acid that is complementary to the third primer, and wherein coupling the third primer to the second single-stranded nucleic acid molecule comprises coupling the third primer to the segment of the second single-stranded nucleic acid.

4. The method of claim 1, wherein the invader species is an oligonucleotide that has a length of at least 30 nucleotides.

5. The method of claim 1, wherein the invader species is an oligonucleotide that is bound to at least a portion of the first or second single-stranded nucleic acid molecule with the aid of a recombinase.

6. The method of claim 2, wherein a number of molecules of the third primer is greater than a number of molecules of the first primer and a number of molecules of the second primer.

7. The method of claim 1, wherein the support is a bead, an array pixel, a sensor, a particle, or an electrode.

8. The method of claim 1, wherein the second primer extension reaction is completed with the aid of a strand-displacing polymerase.

9. The method of claim 2, wherein the third primer is in solution.

10. The method of claim 2, wherein the support comprises the third primer.

11. The method of claim 1, wherein the invader species is an oligonucleotide that cannot be extended via the incorporation of additional nucleotides.

12. The method of claim 1, wherein the nucleic acid sample is amplified isothermally.

13. The method of claim 1, wherein the first single-stranded nucleic acid molecule, the second single-stranded nucleic acid molecule, or the third single-stranded nucleic acid molecule is not released from the support during any of a)-e).

14. A method for amplifying a nucleic acid sample, comprising:
  a) providing a support comprising a first primer;
  b) providing a first double-stranded nucleic acid molecule comprising a first single-stranded nucleic acid molecule and a second single-stranded nucleic acid molecule that is at least partially complementary to said first single-stranded nucleic acid molecule, wherein the double-stranded nucleic acid molecule is derived from the nucleic acid sample, and wherein the second-single-stranded nucleic acid molecule comprises a nucleic acid sequence at least partially complementary to said first primer;
  c) at least partially denaturing the first double-stranded nucleic acid molecule by binding a first invader species free from said support to at least a portion of the first or second single-stranded nucleic acid molecule, which binding exposes a segment of the first single-stranded nucleic acid molecule that is complementary to a second primer separate from said first primer;
  d) coupling the second primer to the segment of the first single-stranded nucleic acid molecule and performing a first primer extension reaction using the second primer to generate a second double-stranded nucleic acid molecule comprising the first single-stranded nucleic acid molecule and a third single-stranded nucleic acid molecule that is complementary to at least a portion of the first single-stranded nucleic acid molecule, wherein the first primer extension reaction separates the second single-stranded nucleic acid molecule from the first single-stranded nucleic acid molecule; and
  e) coupling the first primer to the separated second-single stranded molecule and performing a second primer extension reaction using the first primer to generate a third double-stranded nucleic acid molecule comprising the second single-stranded nucleic acid molecule and a fourth single-stranded nucleic acid molecule.

15. A method for amplifying a nucleic acid sample, comprising:
  a) providing a support comprising a first primer;
  b) coupling the first primer to a first single-stranded nucleic acid molecule that is derived from the nucleic acid sample;
  c) performing a first primer extension reaction using the first primer to generate a first double-stranded nucleic acid molecule comprising the first single-stranded nucleic acid molecule and a second single-stranded nucleic acid molecule that is complementary to at least a portion of the first single-stranded nucleic acid molecule;
  d) at least partially denaturing the first double-stranded nucleic acid molecule by binding an invader species free from said support to at least a portion of the first or second single-stranded nucleic acid molecule, which binding exposes a segment of the first or second single-stranded nucleic acid molecule that is complementary to a second primer; and
  e) coupling the second primer to the segment of the first or second single-stranded nucleic acid molecule and performing a second primer extension reaction using the second primer to generate a second double-stranded nucleic acid molecule comprising the first or second single-stranded nucleic acid molecule and a third single-stranded nucleic acid molecule that is complementary to at least a portion of the first or second single-stranded nucleic acid molecule, wherein the second primer extension reaction separates the first single-stranded nucleic acid molecule from the second single-stranded nucleic acid molecule.

16. The method of claim 15, wherein, in d), the binding of the invader species to the at least a portion of the first or second single-stranded nucleic acid molecule exposes a segment of the first single-stranded nucleic acid molecule that is complementary to the second primer.

17. The method of claim 16, wherein, in e), the method comprises coupling the second primer to the segment of the first single-stranded nucleic acid molecule and performing the second primer extension reaction using the second primer to generate the second double-stranded nucleic acid molecule comprising the first single-stranded nucleic acid molecule and the third single-stranded nucleic acid molecule that is complementary to at least a portion of the first single-stranded nucleic acid molecule.

18. The method of claim 17, further comprising
  f) coupling a third primer to the second single-stranded nucleic acid molecule and performing a third primer extension reaction using the third primer to generate a third double-stranded nucleic acid molecule comprising the second single-stranded nucleic acid molecule and a fourth single-stranded nucleic acid molecule that is complementary to at least a portion of the second single-stranded nucleic acid molecule.

19. The method of claim 18, wherein the third primer is free from the support.

20. The method of claim 18, wherein the third primer is coupled to the support.

21. The method of claim 15, wherein, in d), the binding of the invader species to the at least a portion of the first or second single-stranded nucleic acid molecule exposes a segment of the second single-stranded nucleic acid molecule that is complementary to the second primer.

22. The method of claim 21, wherein, in e), the method comprises coupling the second primer to the segment of the second single-stranded nucleic acid molecule and performing the second primer extension reaction using the second primer to generate the second double-stranded nucleic acid molecule comprising the second single-stranded nucleic acid molecule and the third single-stranded nucleic acid molecule that is complementary to at least a portion of the second single-stranded nucleic acid molecule.

23. The method of claim 22, further comprising
f) coupling a third primer to the first single-stranded nucleic acid molecule and performing a third primer extension reaction using the third primer to generate a third double-stranded nucleic acid molecule comprising the first single-stranded nucleic acid molecule and a fourth single-stranded nucleic acid molecule that is complementary to at least a portion of the first single-stranded nucleic acid molecule.

24. The method of claim 23, wherein the third primer is free from the support.

25. The method of claim 23, wherein the third primer is coupled to the support.

26. The method of claim 15, wherein the second primer is provided free from the support.

27. The method of claim 15, wherein the second primer is provided coupled to the support.

28. The method of claim 15, wherein the support is a bead, an array pixel, a sensor, a particle, or an electrode.

29. The method of claim 15, wherein the first primer extension reaction is completed with the aid of a strand-displacing polymerase.

30. The method of claim 15, wherein the invader species is an oligonucleotide that is bound to at least a portion of the first or second single-stranded nucleic acid molecule with the aid of a recombinase.

31. The method of claim 15, wherein the nucleic acid sample is amplified isothermally.

32. The method of claim 14, further comprising:
at least partially denaturing the third double-stranded nucleic acid molecule by binding a second invader species free from the support to at least a portion of the second or fourth single-stranded nucleic acid molecule, which binding exposes a segment of the second single-stranded nucleic acid molecule that is complementary to a third primer.

33. The method of claim 32, further comprising:
providing the third primer; and
coupling the third primer to the segment of the second single-stranded nucleic acid molecule and performing a third primer extension reaction using the third primer to generate a fourth double-stranded nucleic acid molecule comprising the second single-stranded nucleic acid molecule and a fifth single-stranded nucleic acid molecule that is complementary to at least a portion of the second single-stranded nucleic acid molecule, wherein the third primer extension reaction separates the fourth single-stranded nucleic acid molecule from the second single-stranded nucleic acid molecule.

34. The method of claim 14, wherein the first invader species is selected from the group consisting of an oligonucleotide, a nucleic acid comprising a locked nucleic acid (LNA), a nucleic acid comprising a peptide nucleic acid (PNA), and a sequence-specific single-stranded nucleic acid binding protein.

35. The method of claim 34, wherein the first invader species is an oligonucleotide that cannot be extended by a primer extension reaction.

36. The method of claim 14, wherein the support is a bead, an array pixel, a sensor, a particle, or an electrode.

37. The method of claim 14, wherein the first double-stranded nucleic acid molecule is provided by subjecting a parent double-stranded nucleic acid molecule that is derived from the nucleic acid sample to one or more cycles of a nucleic acid amplification reaction, and wherein the first double-stranded nucleic acid molecule is an amplicon of the parent double-stranded nucleic acid molecule generated during the one or more cycles of the nucleic acid amplification reaction.

38. The method of claim 14, wherein the first primer extension reaction is completed with the aid of a strand-displacing polymerase.

39. The method of claim 14, wherein the first invader species is an oligonucleotide that is bound to at least a portion of the first or second single-stranded nucleic acid molecule with the aid of a recombinase.

40. The method of claim 14, wherein the first primer and the second primer are not invader species.

41. The method of claim 14, wherein the nucleic acid sample is amplified isothermally.

* * * * *